US011571475B1

(12) United States Patent
Riether et al.

(10) Patent No.: US 11,571,475 B1
(45) Date of Patent: Feb. 7, 2023

(54) ANTI-CD70 AND BCR-ABL INHIBITOR COMBINATION THERAPY

(71) Applicant: University of Bern, Bern (CH)

(72) Inventors: Carsten Riether, Bern (CH); Christian Schürch, Spiegel bei Bern (CH); Adrian Ochsenbein, Hinterkappelen (CH); Karen Silence, Overijse (BE)

(73) Assignee: University of Bern, Bern (CH)

( * ) Notice: Subject to any disclaimer, the term of this patent is extended or adjusted under 35 U.S.C. 154(b) by 670 days.

(21) Appl. No.: 16/506,546

(22) Filed: Jul. 9, 2019

Related U.S. Application Data

(62) Division of application No. 14/832,333, filed on Aug. 21, 2015, now Pat. No. 10,391,168.

(60) Provisional application No. 62/040,822, filed on Aug. 22, 2014.

(51) Int. Cl.
| | |
|---|---|
| *A61P 35/00* | (2006.01) |
| *A61K 31/5025* | (2006.01) |
| *A61K 39/00* | (2006.01) |
| *C07K 16/28* | (2006.01) |
| *A61K 39/395* | (2006.01) |
| *A61K 31/506* | (2006.01) |
| *A61K 9/00* | (2006.01) |

(52) U.S. Cl.
CPC ........ *A61K 39/3955* (2013.01); *A61K 9/0019* (2013.01); *A61K 9/0053* (2013.01); *A61K 31/506* (2013.01); *A61K 31/5025* (2013.01); *A61P 35/00* (2018.01); *C07K 16/2875* (2013.01); *C07K 16/2878* (2013.01); *A61K 2039/505* (2013.01); *C07K 2317/20* (2013.01); *C07K 2317/24* (2013.01); *C07K 2317/565* (2013.01); *C07K 2317/73* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,573,924 A | 11/1996 | Beckmann et al. | |
| 5,859,205 A | 1/1999 | Adair et al. | |
| 6,500,633 B1 | 12/2002 | Compton | |
| 6,844,422 B1 | 1/2005 | Niehrs et al. | |
| 7,261,892 B2 | 8/2007 | Terrett | |
| 7,491,390 B2 | 2/2009 | Law et al. | |
| 7,641,903 B2 | 1/2010 | Law et al. | |
| 7,662,387 B2 | 2/2010 | Law et al. | |
| 7,723,477 B2 | 5/2010 | Gurney et al. | |
| 7,728,114 B2 | 6/2010 | Mach et al. | |
| 7,745,156 B2 | 6/2010 | Terrett | |
| 7,745,419 B2 | 6/2010 | Oh et al. | |
| 7,982,013 B2 | 7/2011 | Gurney et al. | |
| 8,124,738 B2 | 2/2012 | Terret et al. | |
| 8,324,361 B2 | 12/2012 | Gurney et al. | |
| 8,455,622 B2 | 6/2013 | McDonagh et al. | |
| 8,507,442 B2 | 8/2013 | Gurney et al. | |
| 8,535,678 B2 | 9/2013 | Law et al. | |
| 8,552,156 B2 | 10/2013 | Takayanagi et al. | |
| 8,604,052 B2 | 12/2013 | Hood et al. | |
| 8,647,623 B2 | 2/2014 | Takayanagi et al. | |
| 8,663,642 B2 | 3/2014 | Law et al. | |
| 8,765,913 B2 | 7/2014 | Gurney et al. | |
| 8,834,882 B2 * | 9/2014 | Silence | A61P 35/00 424/156.1 |
| 8,841,418 B2 | 9/2014 | Karsunky et al. | |
| 9,556,270 B2 | 1/2017 | Takayanagi et al. | |
| 9,605,070 B2 | 3/2017 | Sabatos-Peyton et al. | |
| 9,631,026 B2 | 4/2017 | Karsunky et al. | |
| 9,765,148 B2 * | 9/2017 | Silence | A61P 17/06 |
| 9,765,149 B2 * | 9/2017 | Silence | C07K 16/2875 |
| 11,072,665 B2 * | 7/2021 | Silence | A61P 37/00 |
| 2003/0148321 A1 | 8/2003 | Pecker | |
| 2005/0118656 A1 | 6/2005 | Terrett | |
| 2006/0115832 A1 | 6/2006 | Hoon | |
| 2006/0275844 A1 | 12/2006 | Linke | |
| 2007/0072178 A1 | 3/2007 | Haferlach | |
| 2008/0025989 A1 | 1/2008 | Law et al. | |
| 2008/0138341 A1 | 6/2008 | Law et al. | |
| 2008/0280297 A1 | 11/2008 | Dalla-Favera | |
| 2009/0028872 A1 | 1/2009 | Terret et al. | |
| 2009/0074772 A1 | 3/2009 | Law et al. | |
| 2009/0148942 A1 | 6/2009 | McDonagh et al. | |
| 2009/0232806 A1 | 9/2009 | Law et al. | |
| 2010/0129362 A1 | 5/2010 | Law et al. | |
| 2010/0150925 A1 | 6/2010 | Law et al. | |
| 2010/0150950 A1 | 6/2010 | Coccia et al. | |

(Continued)

FOREIGN PATENT DOCUMENTS

| | | |
|---|---|---|
| WO | WO 1994/005691 A1 | 3/1994 |
| WO | WO 2003/046581 A2 | 6/2003 |

(Continued)

OTHER PUBLICATIONS

Ho et al 2006 (Journal of Clinical Oncology, 2006, 24, No. 18_suppl:2509-2509).*
Ho et al 2008 (Blood, 2008, 112:4683-4689).*
Soumerai et al (Blood, 2007, 110:2575).*
Arroyo Hornero et al., "CD70 expression determines the therapeutic efficacy of expanded human regulatory T cells", Communications Biology, 2020, vol. 3, No. 375, pp. 1-17.

(Continued)

*Primary Examiner* — Laura B Goddard
(74) *Attorney, Agent, or Firm* — Dechert LLP; Andrew T. Wilkins; Victoria E. Pedanou

(57) ABSTRACT

Provided are methods and compositions for the treatment of a BCR-ABL1 related disorder (e.g., chronic myelogenous leukemia) using a therapeutic combination of a WNT signaling pathway inhibitor and a BCR-ABL1 tyrosine kinase inhibitor.

10 Claims, 24 Drawing Sheets

Specification includes a Sequence Listing.

(56) References Cited

U.S. PATENT DOCUMENTS

| | | | |
|---|---|---|---|
| 2010/0158910 A1 | 6/2010 | Law et al. | |
| 2010/0183636 A1 | 7/2010 | Law et al. | |
| 2010/0267626 A1 | 10/2010 | Cheung et al. | |
| 2010/0278779 A1 | 11/2010 | Zeldis | |
| 2011/0190157 A1 | 8/2011 | Kipps | |
| 2012/0093805 A1 | 4/2012 | Kubota | |
| 2012/0178111 A1 | 7/2012 | Diamandis | |
| 2013/0078237 A1 | 3/2013 | Delaney et al. | |
| 2013/0243795 A1 | 9/2013 | Chen et al. | |
| 2014/0141016 A1 | 5/2014 | Silence et al. | |
| 2014/0147450 A1 | 5/2014 | Silence et al. | |
| 2014/0235843 A1 | 8/2014 | Silence et al. | |
| 2015/0086521 A1 | 3/2015 | Godfrin | |
| 2015/0132324 A1 | 5/2015 | Cong et al. | |
| 2015/0141624 A1* | 5/2015 | Barnett | A61K 47/6817 548/204 |

FOREIGN PATENT DOCUMENTS

| | | | | |
|---|---|---|---|---|
| WO | WO 2004/073656 A2 | 9/2004 | | |
| WO | WO 2004/085476 A2 | 10/2004 | | |
| WO | WO 2006/044643 A2 | 4/2006 | | |
| WO | WO 2006/047249 A1 | 5/2006 | | |
| WO | WO 2006/113909 A2 | 10/2006 | | |
| WO | WO 2007/038637 A2 | 4/2007 | | |
| WO | WO 2007/146968 A2 | 12/2007 | | |
| WO | WO 2008/074004 A2 | 6/2008 | | |
| WO | WO 2010/001251 A1 | 1/2010 | | |
| WO | WO 2010/001251 A2 | 1/2010 | | |
| WO | WO 2010/014948 A1 | 2/2010 | | |
| WO | WO 2011/061119 A1 | 5/2011 | | |
| WO | WO 2011/080350 A1 | 7/2011 | | |
| WO | WO 2012/098407 A2 | 7/2012 | | |
| WO | WO 2012/123586 A1 | 9/2012 | | |
| WO | WO-2012123586 A1 * | 9/2012 | | A61P 13/12 |
| WO | WO 2013/093508 A2 | 6/2013 | | |
| WO | WO 2013/177420 A2 | 11/2013 | | |
| WO | WO 2013/185353 A1 | 12/2013 | | |
| WO | WO 2014/033252 A1 | 3/2014 | | |
| WO | WO 2014/045101 A1 | 3/2014 | | |
| WO | WO 2014/100772 A2 | 6/2014 | | |
| WO | WO 2015/138600 A2 | 9/2015 | | |
| WO | WO 2016/111947 A2 | 7/2016 | | |
| WO | WO 2017/079116 A1 | 5/2017 | | |
| WO | WO 2017/134140 A1 | 8/2017 | | |
| WO | WO 2017/021354 A1 | 9/2017 | | |
| WO | WO 2017/160954 A1 | 9/2017 | | |
| WO | WO 2018/229303 A1 | 12/2018 | | |
| WO | WO 2019/141732 A1 | 7/2019 | | |

OTHER PUBLICATIONS

Baba et al., "Highly Enhanced Expression of CD70 on Human T-Lymphotropic Virus Type 1-Carrying T-Cell Lines and Adult T-Cell Leukemia Cells", Journal of Virology, Apr. 2008, pp. 3843-3852.
Baxevanis, "Antibody-based cancer therapy", Expert Opinion: Drug Discovery, 2008, vol. 3, No. 4, pp. 441-452.
Brugnoni et al., "CD70 expression on T-cell subpopulations: study of normal individuals and patients with chronic immune activation", Immunology Letters, 1997, vol. 55, pp. 99-104.
Colman, "Effects of amino acid sequence changes on antibody-antigen interactions", Research in Immunology, 1994, vol. 145, pp. 33-36.
Denoeud et al., "Role of CD27/CD70 pathway of activation in immunity and tolerance", Journal of Leukocyte Biology, Feb. 2011, vol. 89, pp. 195-203.
Harris et al., "Assessing Genetic Heterogeneity in Production Cell Lines: Detection by Peptide Mapping of a Low Level Tyr to Gin Sequence Variant in a Recombinant Antibody", Biotechnology, 1993, vol. 11, pp. 1293-1297.
Manocha et al., "Blocking CD27-CD70 Costimulatory Pathway Suppresses Experimental Colitis", The Journal of Immunology, 2009, vol. 183, pp. 270-276.

Oflazoglu et al., "Blocking of CD27-CD70 Pathway by Anti-CD70 Antibody Ameliorates Joint Disease in Murine Collagen-Induced Arthritis", The Journal of Immunology, 2009, vol. 183, pp. 3770-3777.
Paul, Fundamental Immunology, 3$^{rd}$ Edition, 1993, Chapter 9, pp. 292-295.
Riether et al., "CD27 Signaling Promotes the Proliferation of Human Acute Myeloid Leukemia Cells", Respiration, 2013, vol. 85, No. 6, p. 571, Abstract P192.
Sandberg et al., "Assessment of tumor characteristic gene expression in cell lines using a tissue similarity index (TSI)", Proc Natl Acad Sci USA, Feb. 8, 2005, vol. 102, No. 6, pp. 2052-2057.
Sawalha et al., "Defective DNA methylation and CD70 overexpression in CD4+ T cells in MRL/lpr lupus-prone mice", European Journal of Immunology, 2007, vol. 37, pp. 1407-1413.
Weinberg, "Tumors resemble wound-healing sites", The Biology of Cancer, 2007, Chapter 13.2-13.3, pp. 536-539.
Yanagisawa et al., "Effects of anti-CD70 mAb on Thieler's murine encephalomyelitis virus-induced demyelinating disease", Brain Research, 2010, vol. 1317, pp. 236-245.
U.S. Appl. No. 14/005,113, filed Jan. 24, 2014, 2014/0141016, May 22, 2014, now U.S. Pat. No. 9,765,148, Sep. 19, 2017, Karen Silence.
U.S. Appl. No. 14/073,462, filed Nov. 6, 2016, 2014/0147450, May 29, 2014, now U.S. Pat. No. 8,834,882, Sep. 16, 2014, Karen Silence.
U.S. Appl. No. 14/163,752, filed Jan. 24, 2014, 2014/0235843, Aug. 21, 2014, now U.S. Pat. No. 9,765,149, Sep. 19, 2017, Karen Silence.
U.S. Appl. No. 14/626,038, filed Feb. 19, 2015, 2015/0266963, Sep. 24, 2015, Karen Silence.
U.S. Appl. No. 16/278,522, filed Feb. 18, 2019, 2019/0270823, Sep. 5, 2019, Karen Silence.
U.S. Appl. No. 14/832,333, filed Aug. 21, 2015, U.S. Pat. No. 10/391,168, Aug. 27, 2019, Carsten Riether.
U.S. Appl. No. 16/249,480, filed Jan. 16, 2019, 2019/0241668, Aug. 8, 2019, Luc Van Rompaey.
U.S. Appl. No. 16/719,220, filed Dec. 18, 2019, Johannes De Haard.
U.S. Appl. No. 14/626,038, filed Feb. 19, 2015, 2015/0266963, Sep. 24, 2015, now U.S. Pat. No. 11,072,665, Karen Silence.
U.S. Appl. No. 16/011,342, filed Jun. 18, 2018, 2019/0106498, Apr. 11, 2019, Hans de Haard.
U.S. Appl. No. 16/719,220, filed Dec. 18, 2019, 2020/0222532, Jul. 16, 2020, Johannes De Haard.
Achour et al. (2008) "Tetrameric and homodimeric camelid IgGs originate from the same IgH locus," J. Immunol. 181:2001-2009.
Adam et al. 'CD70 (TNFSF7) is Expressed at High Prevalence in Renal Cell Carcinomas and is Rapidly Internalised on Antibody Binding'British J of Cancer; Aug. 7, 2006, vol. 95, No. 3, pp. 298-306.
Appel et al., Molecular Diversity, 1996, 2:29-34.
Askmyr et al. (2013) "Selective killing of candidate AML stem cells by antibody targeting of IL1RAP," Blood, 121(18):3709-3713.
Baccarani et al. (2006) "Evolving concepts in the management of chronic myeloid leukemia: recommendations from an expert panel on behalf of the European LeukemiaNet," Blood 108:1809-1820.
Belloc et al. (2007) "Imatinib and nilotinib induce apoptosis of chronic myeloid leukemia cells through a Bim-dependant pathway modulated by cytokines," Cancer Biol. Ther. 6:912-919.
Bertrand et al. (2013) "The Costimulatory Molecule CD70 is Regulated by Distinct Molecular Mechanisms and is Associated with Overall Survival in Diffuse Large B-cell Lymphoma," Genes, Chromosomes and Cancer, 52:764-774.
Bosman et al. (2016) "Constitutive NF-KB activation in AML: Causes and treatment strategies," Critical Reviews in Oncology/Hematology, 98:35-44.
Boursalian et al. (2009) "Targeting CD70 for human therapeutic use," Advances in Experimental Medicine and Biology. 647:108-119.
Brown et al. (1996) "Tolerance of single, but not multiple, amino acid replacements in antibody VH CDR 2: a means of minimizing B cell wastage from somatic hypermutation?" J Immunol. 156(9):3285-3291.

(56) References Cited

OTHER PUBLICATIONS

Caron et al. (1992) "Engineered Humanized Dimeric Forms of IgG Are More Effective Antibodies," J. Exp. Med., 176:1191-1195.
Chahlavi et al. (2005) "Glioblastomas Induce T-Lymphocyte Death by Two Distinct Pathways Involving Gangliosides and CD70," Cancer Res., 65(12):5428-5438.
Chan et al. (2010) "Therapeutic antibodies for autoimmunity and inflammation," Nature Reviews: Immunology, 10:301-316.
Claus et al. (2012) "CD27 Signaling Increases the Frequency of Regulatory T Cells and Promotes Tumor Growth," Cancer Res., 72(14):3664-3676.
Clevers et al. (2012) "WNT/β-catenin signaling and disease," Cell. 149:1192-1205.
clinicaltrials.gov (First received Dec. 16, 2011) "AMG 172 First in Human Study in Patients With Kidney Cancer," U.S. National Institutes of Health. ClinicalTrials.gov Identifier: NCT01497821.
clinicaltrials.gov (First received Dec. 3, 2013) "A Study of Vantictumab (OMP-18R5) in Combination With Nab-Paclitaxel and Gemcitabine in Previously Untreated Stage IV Pancreatic Cancer," U.S. National Institutes of Health. ClinicalTrials.gov Identifier: NCT02005315.
clinicaltrials.gov (First received Jul. 17, 2011) "Phase I Clinical Study of CWP232291 in Acute Myeloid Leukemia Patients," U.S. National Institutes of Health. ClinicalTrials.gov Identifier: NCT01398462.
clinicaltrials.gov (First received May 4, 2011) "A Study of LGK974 in Patients With Malignancies Dependent on Wnt Ligands," U.S. National Institutes of Health. ClinicalTrials.gov Identifier: NCT01351103. Accessible on the Internet at URL: http://www.ebi.ac.uk/arrayexpress/experiments/E-MEXP-480. [Last Accessed Dec. 15, 2016].
clinicaltrials.gov (First received Oct. 25, 2013) "A Study of Vantictumab (OMP-18R5) in Combination With Paclitaxel in Locally Recurrent or Metastatic Breast Cancer," U.S. National Institutes of Health. ClinicalTrials.gov Identifier: NCT01973309.
clinicaltrials.gov (First received Sep. 27, 2013) "A Study of Vantictumab (OMP-18R5) in Combination With Docetaxel in Patients With Previously Treated NSCLC," U.S. National Institutes of Health. ClinicalTrials.gov Identifier: NCT01957007.
Colovai et al. (2007) "Expression of Inhibitory Receptor ILT3 on Neoplastic B Cells is Associated with Lymphoid Tissue Involvement Leukemia," Cytometry Part B (Clinical Cytometry) 72B:354-362.
Coluccia et al. (2007) "Bcr-Abl stabilizes β-catenin in chronic myeloid leukemia through its tyrosine phosphorylation," EMBO J. 26:1456-1466.
Corbin et al. (2011) "Human chronic myeloid leukemia stem cells are insensitive to imatinib despite inhibition of BCR-ABL activity," J. Clin. Invest. 121:396-409.
Cortes et al. (Nov. 29, 2012) "Ponatinib in refractory Philadelphia chromosome-positive leukemias," N. Engl. J. Med. 367:2075-2088.
Damschroder et al. (2004) "Analysis of human and primate CD2 molecules by protein sequence and epitope mapping with anti-human CD2 antibodies," Mol. Immunol. 41(10):985-1000.
Deininger (2007) "Optimizing therapy of chronic myeloid leukemia," Exp. Hematol. 35:144-154.
Dempke et al. (2017) "Second- and third-generation drugs for immune-oncology treatment—The more the better?," European Journal of Cancer 74(10):55-72.
Deveraux et al. (1984) "A comprehensive set of sequence analysis programs for the VAX," Nucleic Acids Research, 12(1):387-395.
Diegemann et al. (2006) "Immune Escape for Renal Cell Carcinoma: CD70 Mediates Apoptosis in Lymphocytes," Neoplasia, 8(11):933-938.
Dohner et al. (2017) "Diagnosis and management of AML in adults: 2017 ELN recommendations from an international expert panel," Blood, 129(4):66 pages.
Druker et al. (2001) "Activity of a Specific Inhibitor of the BCR-ABL Tyrosine Kinase in the Blast Crisis of Chronic Myeloid Leukemia and Acute Lymphoblastic Leukemia with the Philadelphia Chromosome," N. Engl. J. Med. 344:1038-1042.
Druker et al. (2001) "Efficacy and Safety of a Specific Inhibitor of the BCR-ABL Tyrosine Kinase in Chronic Myeloid Leukemia," N. Engl. J. Med. 344:1031-1037.
Edwards et al., J. Mol. Biol. (2003) 334, 103-118.
EMBL-EBI Database [Online] (Last updated May 3, 2014) "E-MEXP-480—Transcription profiling of D34+ BCR-ABL+ cells of CML patients in chronic phase or blast crisis to identify differentially expressed stage-specific genes," Accession No. E-MEXP-480. Accessible on the Internet at URL: http://www.ebi.ac.uk/arrayexpress/experiments/E-MEXP-480. [Last Accessed Dec. 15, 2016].
Faderl et al. (1999) "The Biology of Chronic Myeloid Leukemia," N. Engl. J. Med. 341:164-172.
Frank, Immunology and Evolution of Infectious Disease, Chapter 4 "Specificity and Cross-Reactivity," Princeton University Press, 2002.
French et al.: 'Eradication of Lymphoma by CD8 T Cells Following Anti-CD40 Monoclonal Antibody Therapy is Critically Dependent on CD27 Costimulation'. Blood; Jun. 1, 2007, vol. 109, No. 11, pp. 4810-4815.
Genbank Database [Online] (Nov. 2, 2016) "RecName: Full=Proto-oncogene Wnt-1; AltName: Full=Proto-oncogene Int-1 homolog; Flags: Precursor," Accession No. P04628. Accessible on the Internet at URL: https://www.ncbi.nlm.nih.gov/protein/P04628. [Last Accessed Dec. 16, 2016].
Glouchkova et al. (2009) J Immunol 182:718-725.
Goncalves-Silva et al. (2015) "Differential expression and biochemical activity of the immune receptor Tim-3 in healthy and malignant human myeloid cells," Oncotarget, 6(32):33823-33833.
Goto et al. (2012) "Serum soluble CD27 level is associated with outcome in patients with diffuse large B-cell lymphoma treated with rituximab, cyclophosphamide, doxorubicin, vincristine and prednisolone," Leukemia and Lymphoma, 53(8):1494-1500.
Gregory et al., Cancer Cell, 2010, 18:74-87.
Groves et al. (2006) "Affinity maturation of phage display antibody populations using ribosome display," Journal of Immunological Methods. 313:129-139.
Hamad et al. (Hindawi Publishing Corporation, Stem Cells International, 2013, 12 pages).
Han et al. (2005) "Increased prevalence of activated CD70+ CD4+ T cells in the periphery of patients with systematic lupus erythematosus," Lupus 14:598-606.
Hanekamp et al. (2017) "Leukemic stem cells: identification and clinical application," Int. J. Hematol., 105:549-557.
Harlow et al. (1988) Antibodies, A Laboratory Manual. Cold Spring Harbor laboratory. pp. 37-47.
Held-Feindt et al. (2002) "CD70/CD27 Ligand, a member or the TNF family, is expressed in human brain tumors," Int. J. Cancer, 98:352-356.
Hinton et al. (2006) "An Engineered Human IgG1 Antibody with Longer Serum Half-Life," The Journal of Immunology, 176:346-356.
Hishima et al. (2000) "CD70 Expression in Thymic Carcinoma," The American Journal of Surgical Pathology, 2:742-746.
Holliger et al. (2005) "Engineered antibody fragments and the rise of single domains," Nature Biotechnology, 23(9): 1126-1136.
Hsiao et al. (2008) "Tankyrase function at telomeres, spindle poles, and beyond," Biochimie. 90:83-92.
Hu et al., Leukemia, 2009, 23:109-116.
International Preliminary Report on Patentability, PCT/EP2012/054733, dated Sep. 17, 2013, 12 pages.
International Search Report and Written Opinion corresponding to International Patent Application No. PCT/EP2018/066144, dated Aug. 17, 2018.
International Search Report and Written Opinion for International Application No. PCT/EP2019/051058, dated Mar. 21, 2019.
International Search Report, PCT/EP2012/054733, dated Jul. 26, 2012, 5 pages.
Israel et al. (2005) "Anti-CD70 antibodies: a potential treatment for EBV+ CD70-expressing lymphomas," Mol. Cancer Ther. 4:2037-2044.
Jacobs et al. (2015) "CD70: An emerging target in cancer immunotherapy," Pharmacology and Therapeutics 155:1-10.

(56) References Cited

OTHER PUBLICATIONS

Jacobs et al. (2015) "Unlocking the potential of CD70 as a novel immunotherapeutic target for non-small cell lung cancer," Oncotarget, 6(15):13462-13475.
Jak et al., Leukemia & Lymphoma, May 2009; 50(5):788-801.
Jan et al. (2011) "Prospective separation of normal and leukemic stem cells based on differential expression of TIM3, a human acute myeloid leukemia stem cell marker," PNAS, 108(12):5009-5014.
Japp et al. (2015) "Dysfunction of PSA-specific CD8+ cells in prostate cancer patients correlates with CD38 and Tim-3 expression," Cancer of Immunol Immunother, 8 pages.
Jaras et al. (2010) "Isolation and killing of candidate chronic myeloid leukemia stem cells by antibody targeting of IL-1 receptor accessory protein," PNAS, 107(37):16280-16285.
Jilaveanu et al. (2012) "CD70 Expression Patterns in Renal Cell Carcinoma," Human Pathol., 43(9):1394-1399.
Junker et al. (2005) "CD70: A new tumor specific biomarker for renal cell carcinoma," 173:2150-2153.
Kang et al. (2015) "The ITM-containing receptor LAIR1 is essential for acute myeloid leukemia development," Nat. Cell Biol., 17(5):665-677.
Kapinas et al. (2010) "miR-29 modulates Wnt signaling in human osteoblasts through a positive feedback loop," J. Biol. Chem. 285:25221-25231.
Katoh et al. (2007) "WNT signaling pathway and stem cell signaling network," Clin. Cancer Res. 13(14):4042-4045.
Kavalerchik et al. (2008) "Chronic myeloid leukemia stem cells," J. Clin. Oncol. 26:2911-2915.
Kikushige et al. (2010) "TIM-3 is a promising target to selectively kill acute myeloid leukemia stem cells," Cell Stem Cell, 7:708-717.
Kikushige et al. (2013) "TIM-3 as a novel therapeutic target for eradicating acute myelogenous leukemia stem cells," Int. J. Hematol., 98:627-633.
Kikushige et al. (2015) "A TIM-3/Gal-9 Autocrine Stimulatory Loop Drives Self-Renewal of Human Myeloid Leukemia Stem Cells and Leukemic Progression," Cell Stem Cell, 17:341-352.
Koren-Michowitz et al. (Jan. 12, 2012) "Imatinib plasma trough levels in chronic myeloid leukaemia: results of a multicentre study CSTI571AIL11TGLIVEC," Hematol. Oncol. 30:200-205.
Lee et al. (2007) "Unchecked CD70 expression on T cells lowers threshold for T-cell activation in rheumatoid arthritis," J. Immunol., 179(4):2609-2615.
Lens et al. (1999) "Aberrant expression and reverse signaling of CD70 on malignant B cells," British Journal of Hematology, 106:491-503.
Li et al. (Feb. 14, 2012) "Activation of p53 by SIRT1 inhibition enhances elimination of CML leukemia stem cells in combination with imatinib," Cancer Cell. 21:266-281.
Liu et al. (2010) "Sp1/NFκB/HDAC/miR-29b Regulatory Network in KIT-driven Myeloid Leukemia," Cancer Cell. 17:333-347.
Lloyd et al., Protein Engineering, Design & Selection vol. 22 No. 3 pp. 159-168 (2009).
Lugo et al. (1990) "Tyrosine kinase activity and transformation potency of bcr-abl oncogene products," Science. 247:1079-1082.
McEarchern et al. (2008) "Preclinical Characterization of SGN-70, a Humanized Antibody Directed Against CD70," Clin. Cancer Res. 14(23)7763-7772.
McKinney, J Neural Neurosurg Psychiatry 2004;75(Suppl II):ii12-ii17 (2004).
Memorandum, Feb. 22, 2018, Robert W. Bahr, Deputy Commissioner for Patent Examination Policy, pp. 1-2 (2018).
Meyer et al., British Journal of Haematology, 2018, 180, 808-820 (2018).
Naresh et al., Leukemia & Lymphoma, Aug. 2004 Vol. 45 (8), pp. 1569-1577 (2004).
Natsume et al. (2009) "Improving effector functions of antibodies for cancer treatment: Enhancing ADCC and CDC," Drug Design Development and Therapy, 3:7-16.
Nilsson et al. (2005) "Expression of CD27-CD70 on Early B Cell Progenitors in the Bone Marrow: Implication and Therapy of Childhood ALL," Experimental Hematology, 33:1500-1507.
Nolte et al., Immunological Reviews 2009, vol. 2009: 2016-231.
O'Donnell et al. (2017) "Acute Myeloid Leukemia, Version 3," Journal of the National Comprehensive Cancer Network, 15(7):926-957.
O'Hare et al. (2009) "AP24534, a Pan-BCR-ABL Inhibitor for Chronic Myeloid Leukemia, Potently Inhibits the T315I Mutant and Overcomes Mutation-Based Resistance," Cancer Cell. 16:401-412.
Oelke et al. (2004) "Overexpression of CD70 and Overstimulation of IgG Synthesis by Lupus T Cells and T Cells Treated with DNA Methylation Inhibitors," Arthritis and Rheumatism, 50(6):1850-1860.
Ophaegbulam et al. (2015) "Human cancer immunotherapy with antibodies to the PD-1 and PD-L1 pathway," Trends Mol. Med., 21(1):24-33.
O'Hare et al., Nature Reviews Cancer, 2012, 12:513-526.
Padlan (1994) "Anatomy of the antibody molecule," Mol. Immunol. 31(3):169-217.
Perna et al. (2017) "Integration Proteomics and Transcriptomics for Systematic Combinatorial Chimeric Antigen Receptor Therapy of AML," Cancer Cell, 32:506-519.
Petrau et al. (2014) "CD70: A potential target in breast cancer?," Journal of Cancer, 5:761-764.
Polakis (2012) "Drugging Wnt signalling in cancer," EMBO J. 31(12):2737-2746.
Pollyea et al. (2017) "Therapeutic targeting of acute myeloid leukemia stem cells," Blood, 129(12):1627-1635.
Ponce et al. (2017) "SIRPa-antibody fusion proteins stimulate phagocytosis and promote elimination of acute myeloid leukemia cells," Oncotarget, 8(7):11284-11301.
Portolano et al. (1993) "Lack of promiscuity in autoantigen-specific H and L chain combinations as revealed by human H and L chain 'roulette,'" J. Immunol. 150(3):880-887.
Presta et al. (2008) "Molecular engineering and design of therapeutic antibodies," Current Opinion in Immunology, 20:460-470.
Ragusa et al., BMC Cancer 2010, 10: 377.
Ranheim et al., Blood. 1995, pp. 3556-3565 (1995).
Richardson et al. (2014) "Epigenetics in 2013: DNA methylation and miRNA—key roles in systematic autoimmunity," Nat. Rev. Rheumatol., 10(2):72-74.
Riether et al. (Jul. 29, 2015) "Tyrosine kinase inhibitor-induced CD70 expression mediates drug resistance in leukemia stem cells by activating Wnt signaling," Science Translational Medicine. 7:298ra119. pp. 1-35.
Riether et al. (2017) "CD70/CD27 signaling promotes blast sternness and is a viable therapeutic target in acute myeloid leukemia," J. Exp. Med., 214(2):359-380.
Ring et al. (2017) "Anti-SIRPα antibody immunotherapy enhances neutrophil and macrophage antitumor activity," PNAS, 114(49):E10578-E10585.
Rudikoff et al. (1982) "Single amino acid substitution altering antigen-binding specificity," Proc. Natl. Acad. Sci. USA. 79:1979-1983.
Ryan et al. (2010) "Targeting pancreatic and ovarian carcinomas using the auristatin-based anti-CD70 antibody-drug conjugate SGN-75," British Journal of Cancer. 103:676-684.
Sakuishi et al. (2010) "Targeting Tim-3 and PD-1 pathways to reverse T cell exhaustion and restore anti-tumor immunity," J. Exp. Med., 207(10):2187-2194.
Schürch et al. (Feb. 1, 2012) "CD27 signaling on chronic myelogenous leukemia stem cells activates Wnt target genes and promotes disease progression," J. Clin. Invest. 122:624-638.
Shao et al. (2011) "Combination or monoclonal antibodies with DST inhibits accelerated rejection mediated by memory T cells to induce long-lived heart allograft acceptance in mice," Immunology Letters 138:122-128.
Shopes et al. (1992) "A genetically engineered human IgG mutant with enhanced cytolytic activity," The Journal of Immunology, 148:2918-2922.

(56) References Cited

OTHER PUBLICATIONS

Shultz et al. (2005) "Human Lymphoid and Myeloid Cell Development in NOD/LtSz-scid IL2Rγnull Mice Engrafted with Mobilized Human Hemopoietic Stem Cells," J. Immunol. 174:6477-6489.
Silence et al. (2014) "ARGX-110, a highly potent antibody targeting CD70, eliminates tumors via both enhanced ADCC and immune checkpoint blockade," mAbs, 6(2):523-532.
Sloan et al. (2004) "Detection of Differentially Expressed Genes in an Isogenic Breast Metastasis Model using RNA Arbitrarily Primed-Polymerase Chain Reaction Coupled with Array Hybridization (RAP-Array)," American Journal of Pathology, 164(1):315-323.
Tan et al. (Aug. 9, 2013) "Suppression of Wnt Signaling by the miR-29 Family is Mediated by Demethylation of WIF-1 in Non-Small-Cell Lung Cancer," Biochem. Biophys. Res. Commun. 438:673-679.
Tesselaar et al. (1997) "Characterization of murine CD70, the ligand of the TNF receptor family member CD27," J. Immunol. 159:4959-4965.
Tesselaar et al. (2003) "Expression of the murine CD27 ligand CD70 in vitro and in vivo," J. Immunol. 170:33-40.
Theocharides et al. (2012) "Disruption of SIRPα signaling in macrophages eliminates human acute myeloid leukemia stem cells in xenografts," J. Exp. Med., 209(10):1883-1899.
Uniprot Database [Online] (Feb. 6, 2007) "UniProtKB-A1Z199 (A1Z199_HUMAN)," Accession No. A1Z199. Accessible on the Internet at URL: http://www.uniprot.org/uniprot/A1Z199. [Last Accessed Dec. 16, 2016].
Uniprot Database [Online] (Nov. 1, 1996) "UniProtKB-Q13745 (Q13745_HUMAN)," Accession No. Q13745. Accessible on the Internet at URL: http://www.uniprot.org/uniprot/Q13745. [Last Accessed Dec. 16, 2016].
Vaccaro et al. (2005) "Engineering the FC region of immunoglobulin G to modulate in vivo antibody levels," Nature Biotechnology, 23(10):1283-1288.
Vajdos et al. (2002) "Comprehensive Functional Maps of the Antigen-binding Site of an Anti-ErbB2 Antibody Obtained with Shotgun Scanning Mutagenesis," J. Mol. Biol. 320(2):415-428.
Van Doorn et al. (2004) "Aberrant Expression of the Tyrosine Kinase Receptor EphA4 and the Transcription Factor Twist in Sezary Syndrome Identified by Gene Expression Analysis," Cancer Research, 64:5578-5586.
Van Regenmortel, Journal of Immunological Methods, 1998, 216:37-48.
Voronkov et al. (2013) "Wnt/beta-catenin signaling and small molecule inhibitors," Current Pharmaceutical Design. 19:634-664.
Waaler et al. (2012) "A novel tankyrase inhibitor decreases canonical Wnt signaling in colon carcinoma cells and reduces tumor growth in conditional APC mutant mice," Cancer Res. 72(11):2822-2832.
Wajant, H. (2006) "Therapeutic targeting of CD70 and CD27," Expert Opinion on Therapeutic Targets, 20(8):959-973.
Wang et al. (2007) "Antibody Structure, Instability, and Formulation," Journal of Pharmaceutical Sciences, 96(1):1-26.
Wang et al. (2012) "Distinctive Features of the Differentiated Phenotype and Infiltration of Tumor-reactive Lymphocytes in Clear Cell Renal Cell Carcinoma," Cancer Res., 72(23):6119-6129.
Wang et al. (2017) "Circular RNAs in human cancer," Molecular Cancer, 16(25):8 pages.
Webster's New World Dictionary, Third College Edition, 1988, see p. 1067 (1988).
Wischhusen et al. (2002) "Identification of CD70-mediated Apoptosis of Immune Effector Cells as a Novel Immune Escape Pathway of Human Glioblastoma," Cancer Research, 62:2592-2599.
Yamane-Ohnuke et al. (2009) "Production of therapeutic antibodies with controlled fucosylation," mAbs, 1(3):230-236.
Yang et al. (2014) "TGF-βupregulates CD70 expression and induces exhaustion of effector memoryT cells in B-cell non-Hodgkin's lymphoma," Leukemia, 28(9):1872-1884.
Yeung et al. (2009) "Engineering Human IgG1 Affinity to Human Neonatal Fc Receptor: Impact of Affinity Improvement on Pharmacokinetics in Primates," The Journal of Immunology, 182:7663-7671.
Zahnd et al. (2010) "Computational analysis of off-rate selection experiments to optimize affinity maturation by directed evolution," Protein Engineering: Design & Selection. 23(4):175-184.
Zalevsky et al. (2010) "Enhanced antibody half-life improves in vivo activity," Nat. Biotechnol., 28(2):157-159.
Zhang et al. (2010) "Effective targeting of quiescent chronic myelogenous leukemia stem cells by histone deacetylase inhibitors in combination with imatinib mesylate," Cancer Cell. 17:427-442.
Zhou et al. (2011) "Histone modifications and methyl-CpG-binding domain protein levels at the TNFSF7 (CD70) promoter in SLE CD4+ T cells," Lupus, 20:1365-1371.
Aftimos et al., "Phase I Dose-Escalation Study of the Anti-CD70 Antibody ARGX-110 in Advanced Malignancies", Clinical Cancer Research, Nov. 2017, 23(21):6411-6420.
Argenx [online], 2017, "ARGX-110", https://web.archive.org/web/20170505150651/www.argenx.com:80/en-GB/content/argx-110/18/ [accessed May 5, 2017].
Barthelemy et al., "Comprehensive Analysis of the Factors Contributing to the Stability and Solubility of Autonomous Human VH Domains", Journal of Biological Chemistry, 2008, 283: 3639-3654.
Beiboer et al., "Guided selection of a pan carcinoma specific antibody reveals similar binding characteristics yet structural divergence between the original murine antibody and its human equivalent", Journal of Molecular Biology, 2000, 296(3): 833-849.
CAS Registry No. 0641571-10-0. [Last Accessed Dec. 16, 2016].
CAS Registry No. 1165740-62-4. [Last Accessed Dec. 16, 2016].
CAS Registry No. 302962-49-8. [Last Accessed Dec. 16, 2016].
CAS Registry No. 379231-04-6. [Last Accessed Dec. 16, 2016].
CAS Registry No. 380843-75-4. [Last Accessed Dec. 16, 2016].
CAS Registry No. 639089-54-6. [Last Accessed Dec. 16, 2016].
CAS Registry No. 664993-53-7. [Last Accessed Dec. 16, 2016].
CAS Registry No. 82115-62-6. [Last Accessed Dec. 16, 2016].
CAS Registry No. 859212-16-1. [Last Accessed Dec. 16, 2016].
CAS Registry No. 943319-70-8. [Last Accessed Dec. 16, 2016].
Choi et al., "Predicting antibody complementarity determining region structures without classification", Molecular BioSystems, 2011,7(12): 3327-3334.
clinicaltrials.gov, "A Study of ARGX-110 in Combination with Azacytidine in Participants with Newly Diagnosed Acute Myeloid Leukemia (AML) or High Risk Myelodysplastic Syndrome (MDS)", ClinicalTrials.gov Identifier No. NCT03030612, Jan. 25, 2017.
Combined Search and Examination Report dated Feb. 8, 2019 in related Application No. GB1709677.7 (4 pages).
De Genst et al., "Antibody repertoire development in camelids", Developmental and Comparative Immunology, 30 (2006); 187-198.
Griffiths et al., "Human anti-self antibodies with high specificity from phage display libraries", The EMBO Journal, 1993, 12:725-734.
International Preliminary Report on Patentability for PCT International Patent Application No. PCT/EP2019/085982, dated Jun. 19, 2020.
International Search Report and Written Opinion for PCT International Patent Application No. PCT/EP2019/085982, dated Mar. 20, 2020.
International Search Report with Written Opinion for PCT International Patent Application No. PCT/EP2017/067923, dated Nov. 15, 2017.
Jones et al. (2008) "Structure of IL-22 bound to its high-affinity IL-22R1 chain," Structure. 16(9):1333-1344.
Kabat et al. (1977) "Unusual distributions of amino acids in complementarity-determining (hypervariable) segments of heavy and light chains of immunoglobulins and their possible roles in specificity of antibody-combining sites," J. Biol. Chem. 252:6609-6616.
Klimka et al., "Human anti-CD30 recombinant antibodies by guided phage antibody selection using cell panning", British Journal of Cancer, 2000, 83:252-260.
Lefranc et al. (1999) "IMGT, the international ImMunoGeneTics database," Nucleic Acids Res. 27:209-212.

(56) References Cited

OTHER PUBLICATIONS

Ma et al. (2008) "IL-22 is required for Th17 cell-mediated pathology in a mouse model of psoriasis-like skin inflammation," J Clin. Invest. 118:597-607.

MacCallum et al. (1996) "Antibody-antigen interactions: contact analysis and binding site topography," J. Mol. Biol. 262:732-745.

Malia et al., "Epitope mapping and structural basis for the recognition of phosphorylated tau by the anti-tau antibody AT8", Proteins, 2016, 84(4): 427-434.

Martin et al. (1996) "Structural Families in Loops of Homologous Proteins: Automatic Classification, Modelling and Application to Antibodies," J. Mol. Biol. 263(5):800-15.

Mather (1980) "Establishment and Characterization of Two Distinct Mouse Testicular Epithelial Cell Line," Biol. Reprod. 23:243-251.

Mather et al. (1982) "Culture of testicular cells in hormone-supplemented serum-free medium," Annals N.Y. Acad. Sci. 383:44-68.

Morea et al. (2000) "Antibody Modeling: Implications for Engineering and Design," Methods, 20:267-279.

Negger (2001) "Human Vλ Germline Sequences (VBase)," University of Zurich. Accessible on the Internet at URL: http://www.bioc.uzh.ch/antibody/Sequences/Germlines/VBase_hVL.html. [Last Accessed Dec. 4, 2017].

Ono et al. (1999) "The humanized anti-HM1.24 antibody effectively kills multiple myeloma cells by human effector cell-mediated cytotoxicity," Mol. Immunol. 36:387-395.

Pollyea et al., "Venetoclax with azacitidine disrupts energy metabolism and targets leukemia stem cells in patients with acute myeloid leukemia", Nat Medicine, Nov. 12, 2018, 24(12):1859-1866.

Sabat et al. (Jan. 2014) "Therapeutic opportunities of the IL-22-IL-22R1 system," Nat. Rev. Drug Discov. 13(1):21-38.

Tatusova et al. (1999) "Blast 2 sequences—a new tool for comparing protein and nucleotide sequences," FEMS Microbiol Lett. 174:247-250.

Tatusova et al. (1999) "Erratum: Blast 2 sequences—a new tool for comparing protein and nucleotide sequences [FEMS Microbiol. 174 (1999) 247-250]," FEMS Microbiol. Lett. 177:187-188.

Teh et al., "Enhancing venetoclax activity in acute myeloid leukemia by co-targeting MCL1", Leukemia, Jul. 28, 2017, 32(2): 303-312.

Tomlinson et al. (1995) "The structural repertoire of the human V kappa domain," EMBO J. 14:4628-4638.

Tramontano et al. (1989) "Structural determinants of the conformations of medium-sized loops in proteins," Proteins. 6:382-94.

Tramontano et al. (1990) "Framework residue 71 is a major determinant of the position and conformation of the second hypervariable region in the VH domains of immunoglobulins," J. Mol. Biol. 215:175-182.

Urlaub et al. (1980) "Isolation of Chinese hamster cell mutants deficient in dihydrofolate reductase activity," Proc. Natl. Acad. Sci. USA. 77:4216-20.

Van Belle et al. (2012) "IL-22 is required for imiquimod-induced psoriasiform skin inflammation in mice," J. Immunol. 188(1):462-9.

Vinter et al. (Dec. 10, 2014) "Aldara®-induced skin inflammation: studies of patients with psoriasis," Br J Dermatol. 172(2):345-53.

Ward et al., Binding activities of a repertoire of single immunoglobin variable domains secreted from *Escherichia coli*, Nature, 1989, 341:544-546.

Wei et al., "Midostaurin, enasidenib, CPX-351, gemtuzumab ozogamicin, and venetoclax bring new hope to AML", Blood, Dec. 7, 2017, 130(23): 2469-2474.

Williams et al. (1996) "Sequence and evolution of the human germline V lambda repertoire," J. Mol. Biol. 264:220-232.

U.S. Appl. No. 16/011,342, filed Jun. 18, 2018, 2019/0106498, Apr. 11, 2019, Haans De Haard.

\* cited by examiner

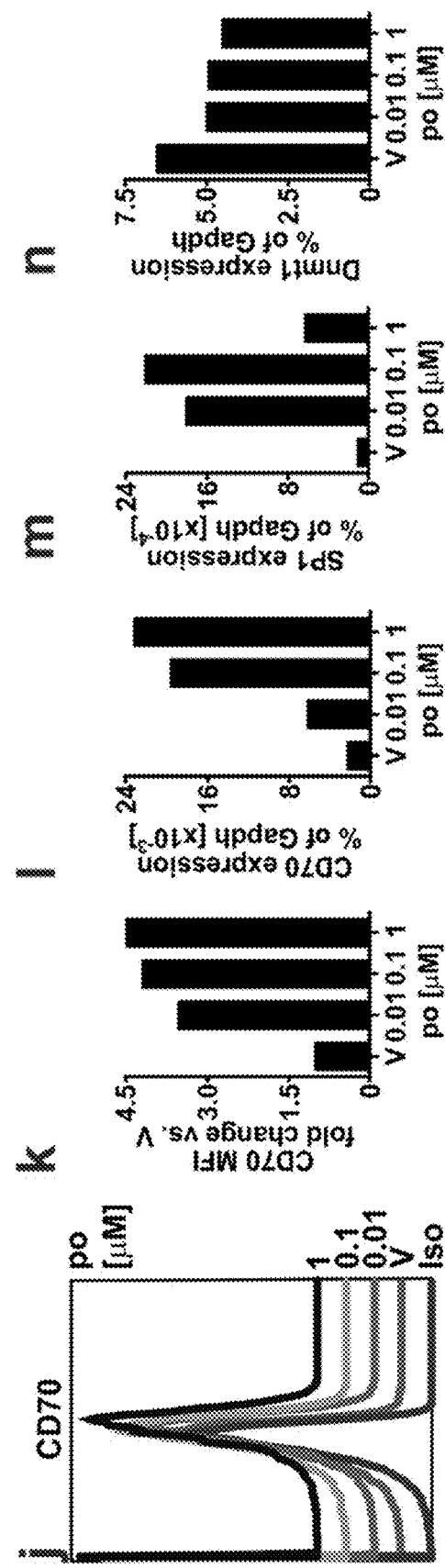
FIGURE 1 (ctd.)

FIGURE 1 (ctd.)
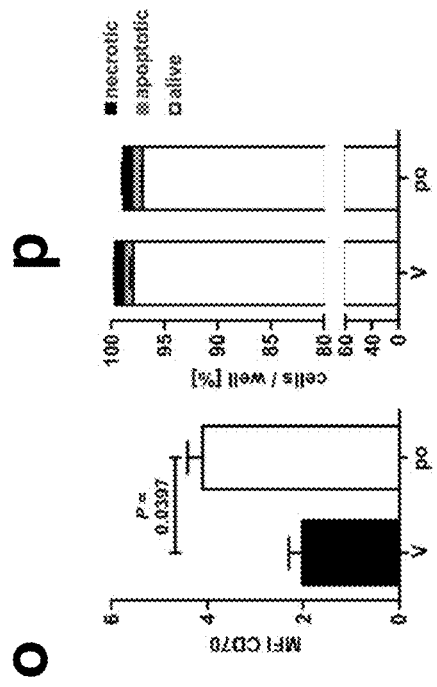
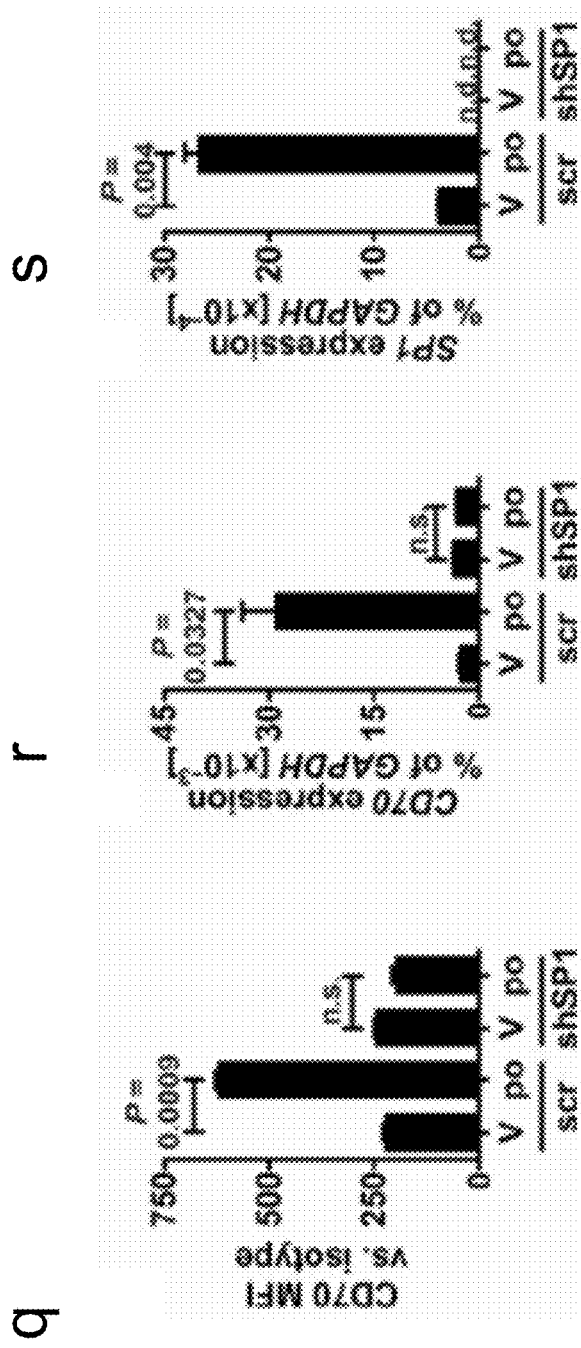

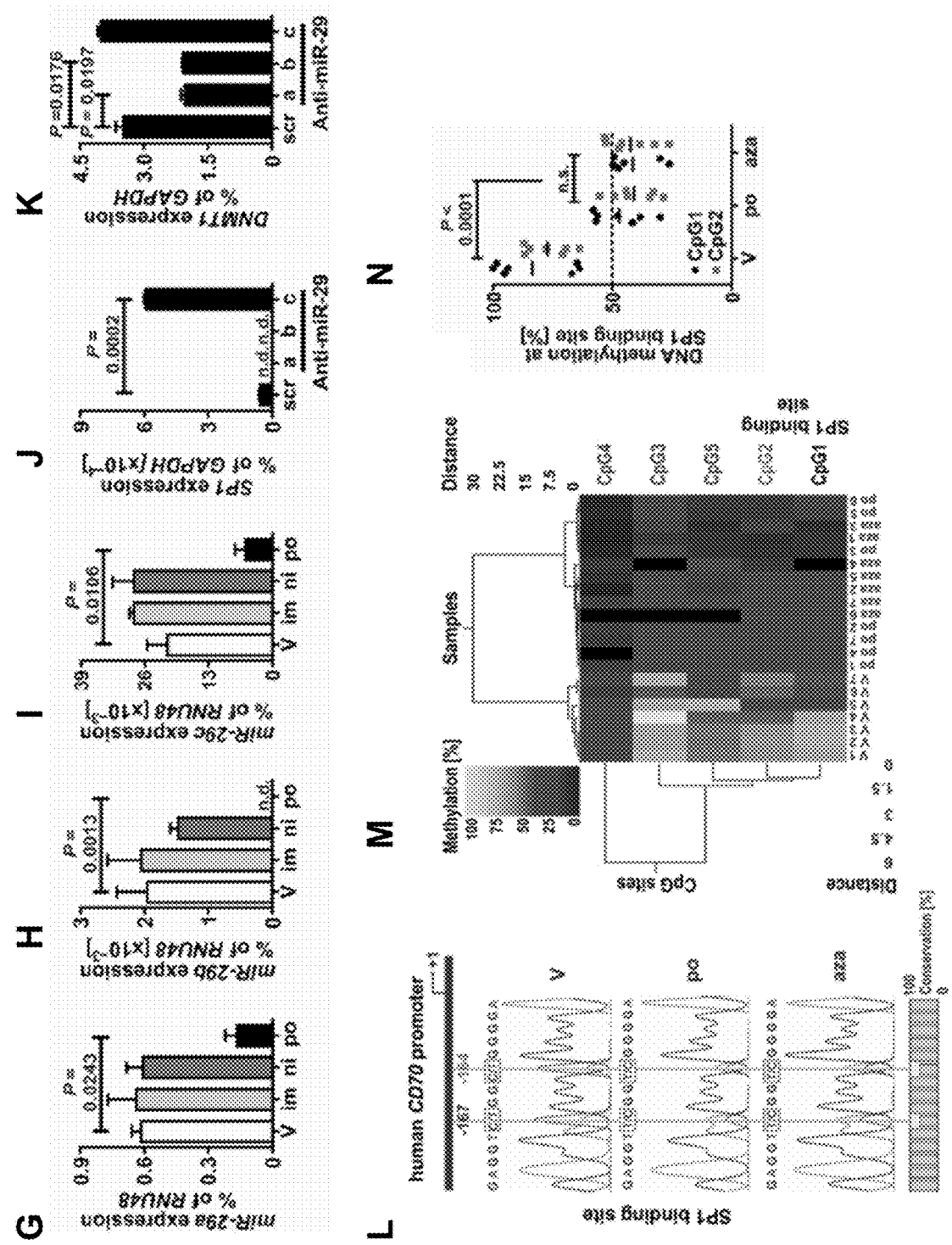
FIGURE 2 (ctd.)

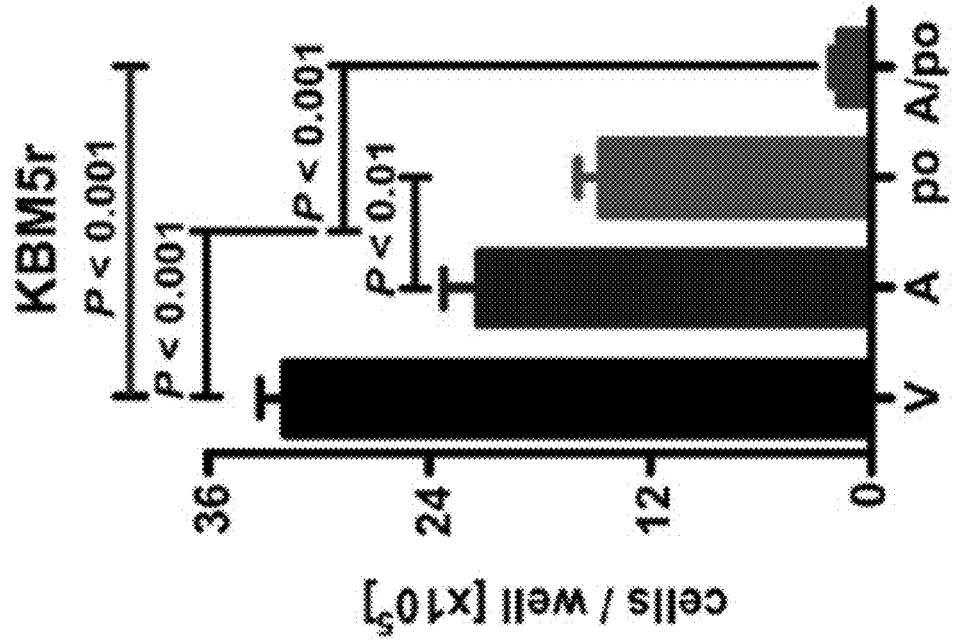
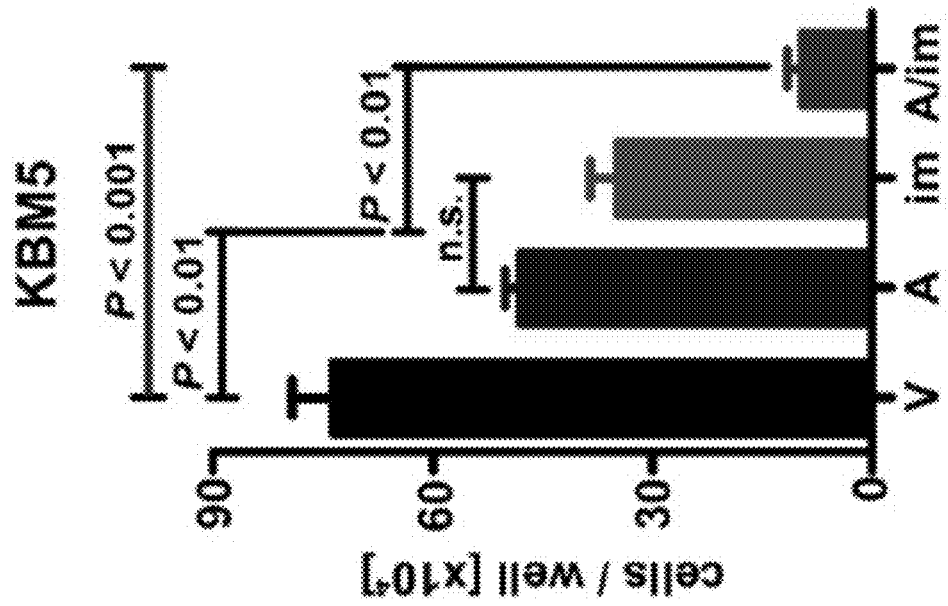
FIGURE 3 (ctd.)

FIGURE 3 (ctd.)
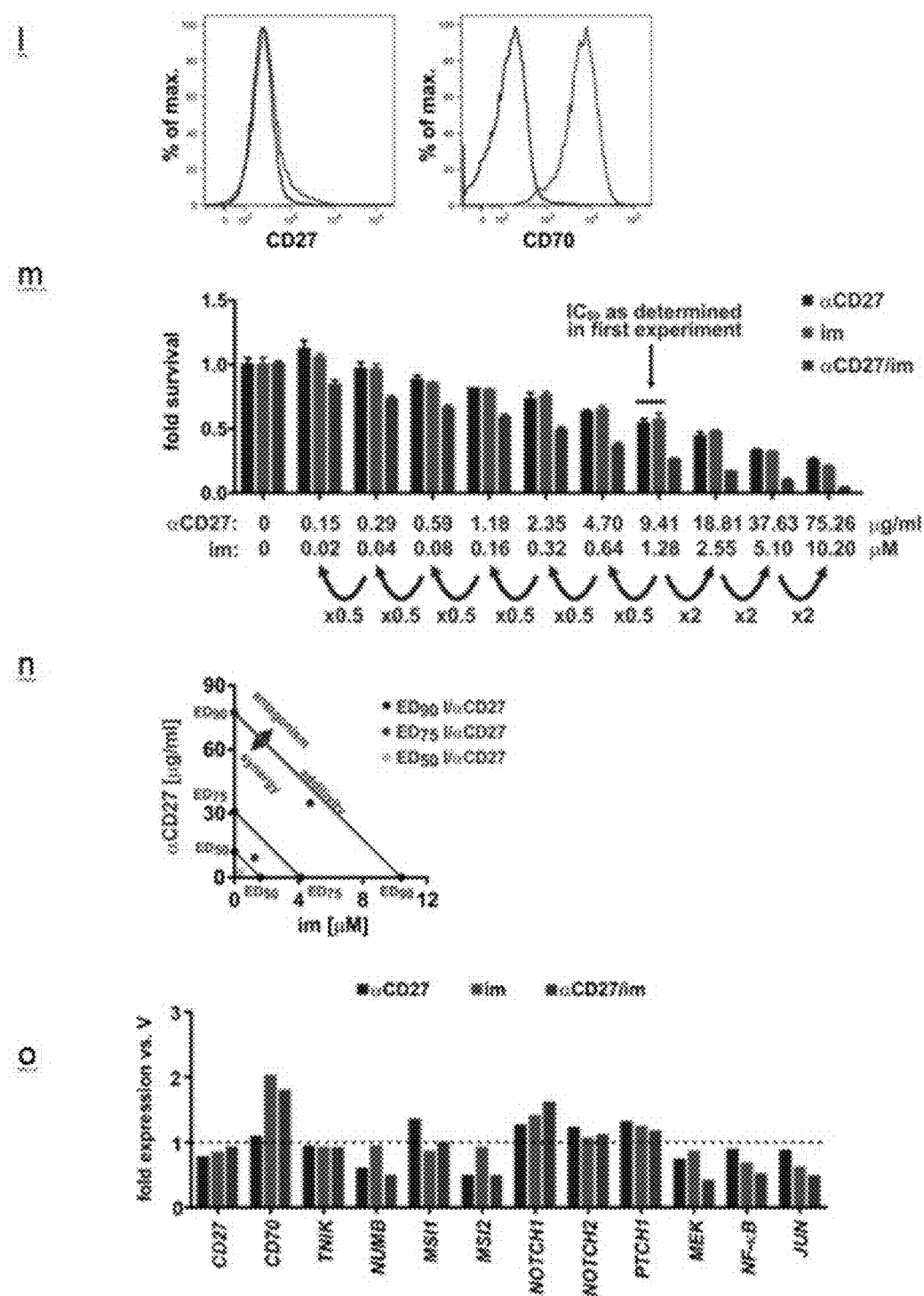

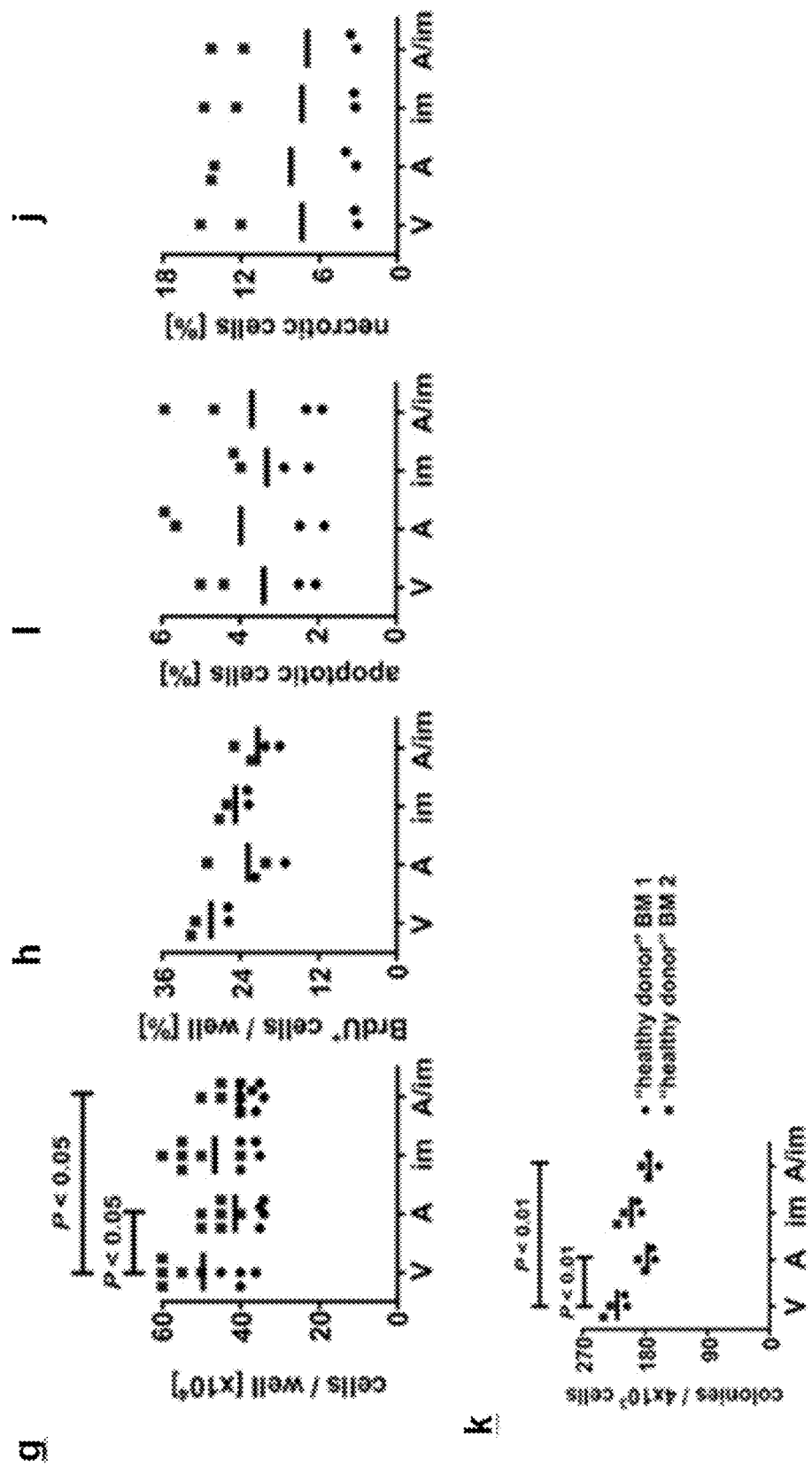
FIGURE 4 (ctd.)

FIGURE 5 (ctd.)
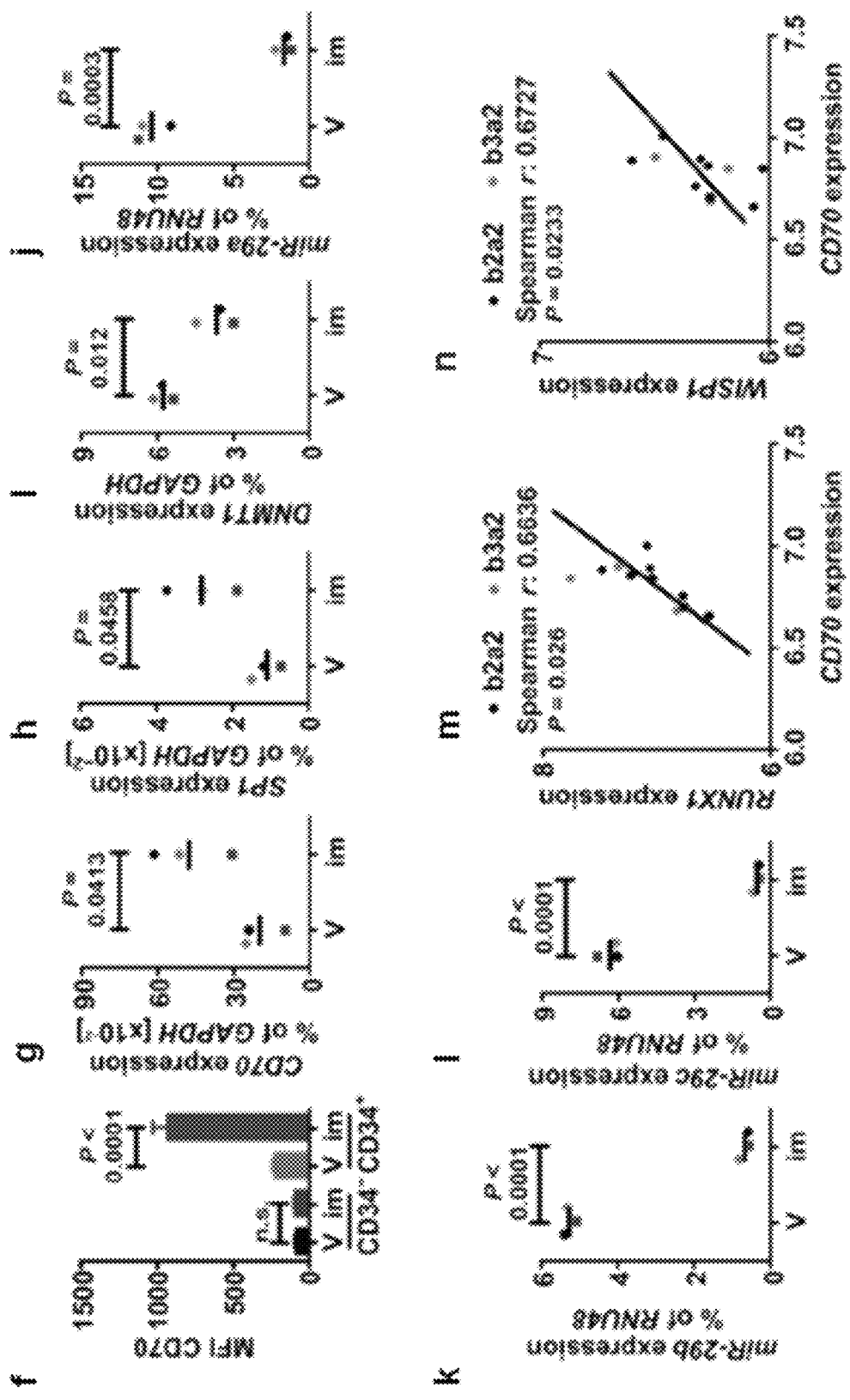

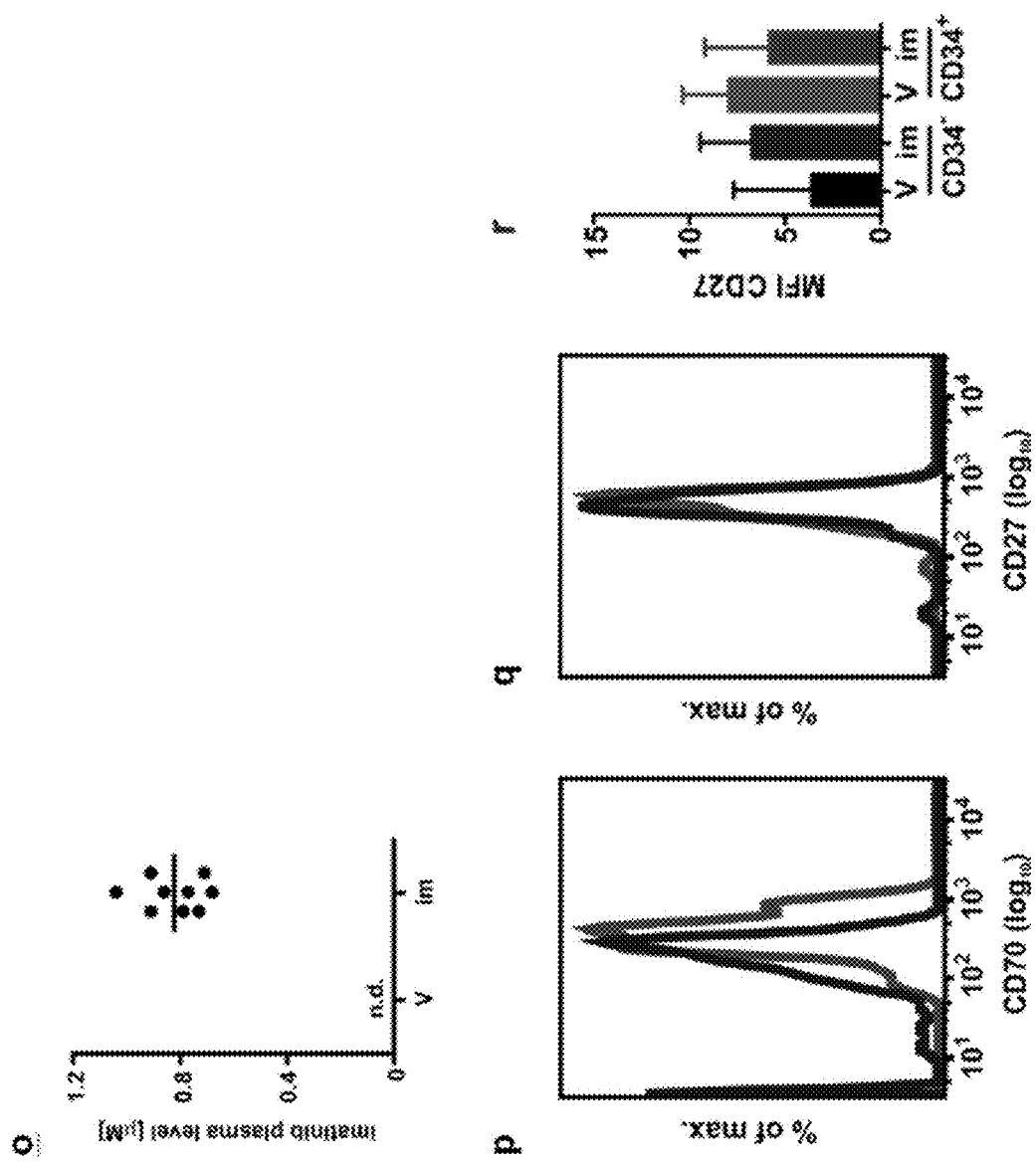
FIGURE 5 (ctd.)

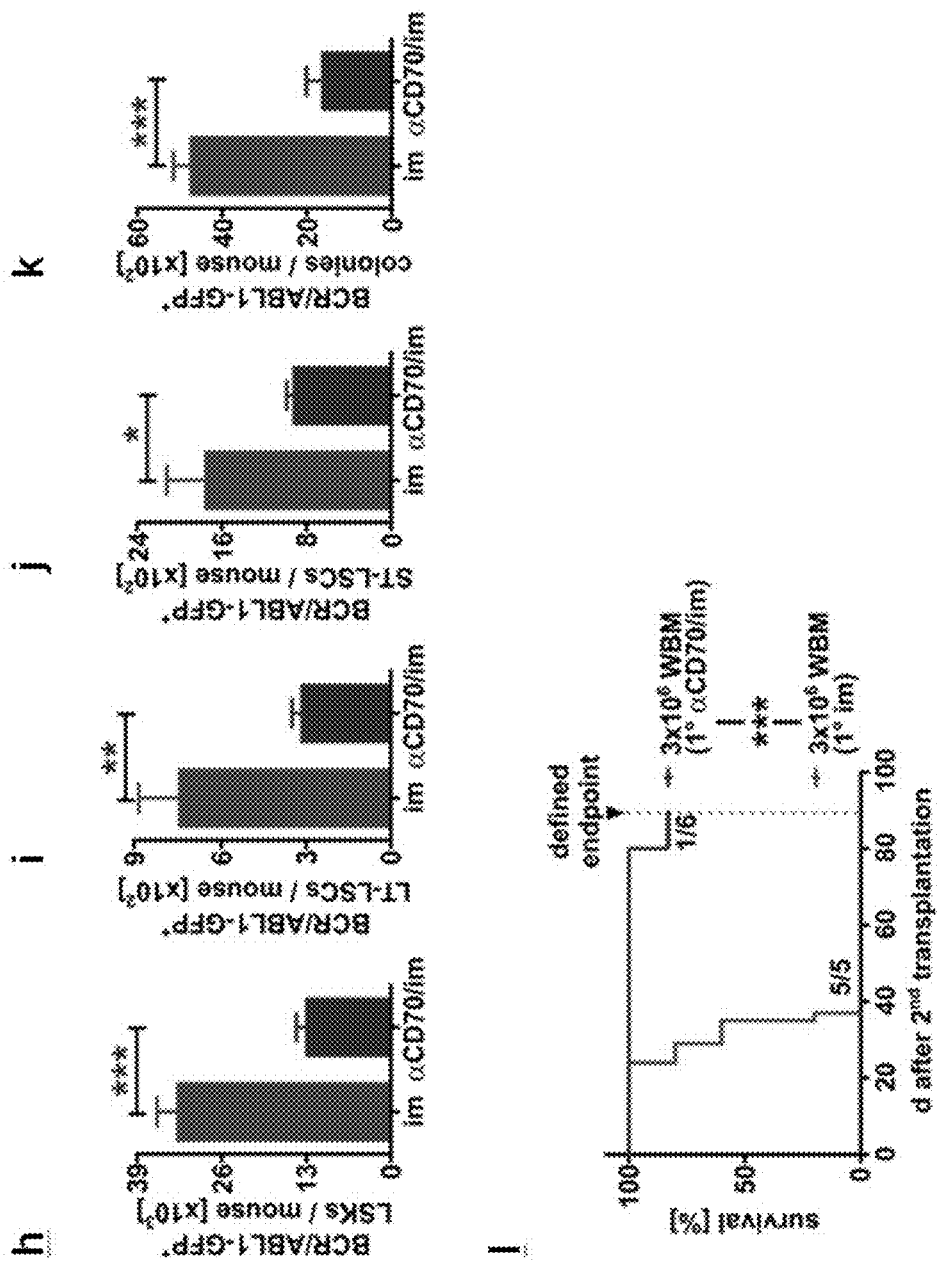
FIGURE 6 (ctd.)

FIGURE 6 (ctd.)
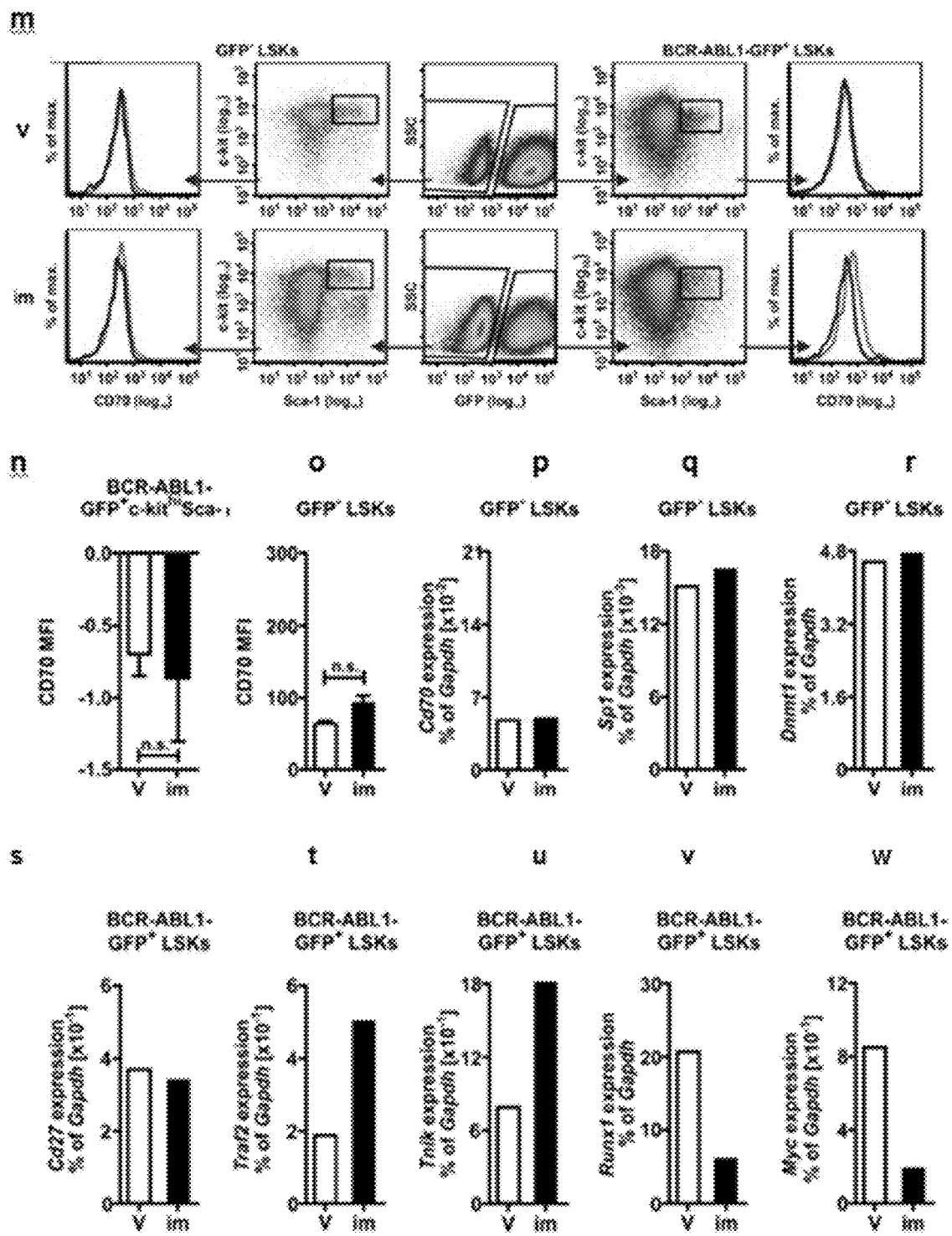

ANTI-CD70 AND BCR-ABL INHIBITOR COMBINATION THERAPY

RELATED APPLICATIONS

This application is a division of U.S. patent application Ser. No. 14/832,333, filed Aug. 21, 2015, now U.S. Pat. No. 10,391,168, which claims the benefit of priority to U.S. Provisional Patent Application Ser. No. 62/040,822, filed Aug. 22, 2014, the entire disclosures of which are hereby incorporated herein by reference.

SEQUENCE LISTING

The instant application contains a Sequence Listing which has been submitted electronically in ASCII format and is hereby incorporated by reference in its entirety. Said ASCII copy, created on Jul. 9, 2019, is named 614774_AGX5-017CON_Sequence_Listing.txt and is 8,303 bytes in size.

FIELD OF THE INVENTION

The present disclosure relates to methods and compositions for the treatment of BCR-ABL1 related disorders (e.g., chronic myelogenous leukemia).

BACKGROUND

Chronic myelogenous leukemia (CML) originates from leukemia stem cells (LSCs) harboring the BCR-ABL1 fusion oncogene, a constitutively active tyrosine kinase (reviewed in Kavalerchik et al. *J Clin Oncol* (2008) 26, 2911-2915; Lugo et al. (1990) *Science* 247, 1079-1082). The introduction of imatinib, a tyrosine kinase inhibitor (TKI) targeting BCR-ABL1, has transformed the clinical approach to the management of CML and dramatically improved the patient outcome (Druker et al. *N Engl J Med* (2001) 344, 1038-1042; Druker et al. (2001) *N Engl J Med* 344, 1031-1037.; and Baccarani et al. (2006) *Blood* 108, 1809-1820).

Nonetheless, a cure for CML remains elusive. Many patients with advanced disease fail to achieve sustainable long term remission primarily because of the emergence of disease-initiating LSCs that are resistant to TKIs despite BCR-ABL1 inhibition (Corbin, A. S., et al. (2011) *J Clin Invest* 121, 396-409). Thus, interruption of TKI treatment leads to a relapse of the disease whereas patients receiving TKI treatment over an extended period of time have a significant risk of acquiring TKI-resistant CML that can progress to acute leukemia (Faderl, S., et al. (1999) *N Engl J Med* 341, 164-172).

Accordingly, there is an urgent need in the art for methods and compositions that can be used to treat chronic myelogenous leukemia, including TKI-resistant chronic myelogenous leukemia.

SUMMARY

The present disclosure provides compositions and methods for treating a subject suffering from a BCR-ABL1 related disorder (e.g., chronic myelogenous leukemia). The methods disclosed herein generally comprise administering to the subject an effective amount of a therapeutic combination of a WNT signaling pathway inhibitor and a BCR-ABL1 tyrosine kinase inhibitor. Such methods are based, in part, on the surprising discovery that a BCR-ABL1 tyrosine kinase inhibitor and CD70/CD27 inhibitor act synergistically to eradicate leukemia cells in vitro and in vivo. The methods and compositions disclosed herein are particularly useful for treating a chronic myelogenous leukemia that is resistant to a BCR-ABL1 tyrosine kinase inhibitor.

Accordingly in one aspect, the present disclosure provides a method of treating a subject with a BCR-ABL1 related disorder (e.g., a chronic myelogenous leukemia), the method comprising administering to the subject an effective amount of a WNT signaling pathway inhibitor and a BCR-ABL1 tyrosine kinase inhibitor.

In certain embodiments, the BCR-ABL1 related disorder is chronic myelogenous leukemia (CML). In certain embodiments, the BCR-ABL1 related disorder is a CML that is resistant to a BCR-ABL1 tyrosine kinase inhibitor.

In certain embodiments, the WNT signaling inhibitor is an inhibitor of CD27 signaling. In certain embodiments, the inhibitor of CD27 signaling is a molecule that binds to CD27 and inhibits the binding of CD70 to CD27. In certain embodiments, the inhibitor of CD27 signaling is an anti-CD27 antibody or antigen binding fragment thereof. In certain embodiments, the antibody is a murine, humanized or human antibody.

In certain embodiments, the inhibitor of CD27 signaling is a molecule that binds to CD70 and inhibits the binding of CD70 to CD27. In certain embodiments, the inhibitor of CD27 signaling is an anti-CD70 antibody or antigen binding fragment thereof. In certain embodiments, the antibody is a murine, humanized or human antibody. In certain embodiments, the antibody is vorsetuzumab. In certain embodiments, the antibody comprises a heavy chain variable domain comprising at least one of CDRH1, CDRH2, and CDRH3 regions, and a light chain variable domain comprising at least one of CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively. In certain embodiments, the antibody comprises a heavy chain variable domain comprising the amino acid sequence set forth in SEQ ID NO: 7. In certain embodiments, the antibody comprises a light chain variable domain comprising the amino acid sequence set forth in SEQ ID NO: 8. In certain embodiments, the antibody comprises a heavy chain variable domain and the light chain variable domain comprising the amino acid sequences set forth in SEQ ID NOs: 7 and 8, respectively.

In certain embodiments, the BCR-ABL1 inhibitor is imatinib, nilotinib, dasatinib, bosutinib, ponatinib, bafetinib, saracatinib, tozasertib, or danusertib.

In another aspect, the instant disclosure provides a therapeutic combination comprising a WNT signaling pathway inhibitor and BCR-ABL1 inhibitor.

In certain embodiments, the WNT signaling inhibitor is an inhibitor of CD27 signaling. In certain embodiments, the inhibitor of CD27 signaling is a molecule that binds to CD27 and inhibits the binding of CD70 to CD27. In certain embodiments, the inhibitor of CD27 signaling is an anti-CD27 antibody or antigen-binding fragment thereof. In certain embodiments, the antibody is murine, humanized, or human antibody.

In certain embodiments, the inhibitor of CD27 signaling is a molecule that binds to CD70 and inhibits the binding of CD70 to CD27. In certain embodiments, the inhibitor of CD70 signaling is an anti-CD70 antibody or antigen binding fragment thereof. In certain embodiments, the antibody is murine, humanized, or human antibody. In certain embodiments, the antibody is vorsetuzumab. In certain embodiments, the antibody comprises a heavy chain variable domain comprising at least one of CDRH1, CDRH2, and CDRH3 regions, and a light chain variable domain comprising at least one of CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively. In certain embodiments, the antibody comprises a heavy chain variable domain comprising the amino acid sequence set forth in SEQ ID NO: 7. In certain embodiments, the antibody comprises a light chain variable domain comprising the amino acid sequence set forth in SEQ ID NO: 8. In certain embodiments, the antibody comprises a heavy chain variable domain and the light chain variable domain comprising the amino acid sequences set forth in SEQ ID NOs: 7 and 8, respectively.

In certain embodiments, the BCR-ABL1 inhibitor is imatinib, nilotinib, dasatinib, bosutinib, ponatinib, bafetinib, saracatinib, tozasertib, or danusertib.

In certain embodiments, the WNT signaling pathway inhibitor and BCR-ABL1 inhibitor are in the same formulation. In certain embodiments, the WNT signaling pathway inhibitor and BCR-ABL1 inhibitor are in separate formulations.

In another aspect, the present disclosure provides a kit comprising any one of the therapeutic combinations disclosed herein, wherein the kit comprises a first container comprising the WNT signaling pathway inhibitor and a second container comprising the BCR-ABL1 inhibitor. In certain embodiments, the kit further comprises instructions for using the therapeutic combination to treat a BCR-ABL1 related disorder.

BRIEF DESCRIPTION OF THE DRAWINGS

The skilled artisan will understand that the drawings, described below, are for illustration purposes only. The figures are not intended to limit the scope of the teachings in any way.

(j-n) $1\times10^5$ imatinib-resistant KBM5r cells were cultured in the presence of vehicle or ponatinib (po) at the indicated concentrations for 72 h. (j) Histograms and (k) mean fluorescence intensity (MFI) of CD70 protein expression (FACS). (l) CD70, (m) SP1, and (n) Dnmt1 mRNA expression (real-time RT-PCR).

(o-p) CD70 up-regulation is induced early after TKI treatment in KBM5r cells. $1\times10^5$ imatinib-resistant KBM5r cells were cultured in duplicates in the presence of vehicle or ponatinib (po, 0.1 μM) for 16 h. (o) Mean fluorescence intensity (MFI) of CD70 protein expression (FACS) and (p) cell viability (FACS). Apoptotic and necrotic cells were defined as Annexin-V+ and Annexin-V+7-AAD+ cells, respectively. Data are displayed as mean±s.e.m. Statistics: student's t-test.

(q-s) Tyrosine kinase inhibitor (TKI)-mediated CD70 up-regulation is mediated by SP1. KBM5r cells ($1\times10^5$) transfected with shSP1 (shSP1) or the respective control scrambled RNA lentiviral particles (scr) were cultured for 72 hours in the presence of vehicle or ponatinib (po; 0.1 μM). MFI of CD70 protein expression (FACS) (q), CD70 (r) and SP1 (s) mRNA expression (qRT-PCR). n.s., not significant; n.d., not detected; GAPDH, glyceraldehyde-3-phosphate dehydrogenase.

Figure 2:
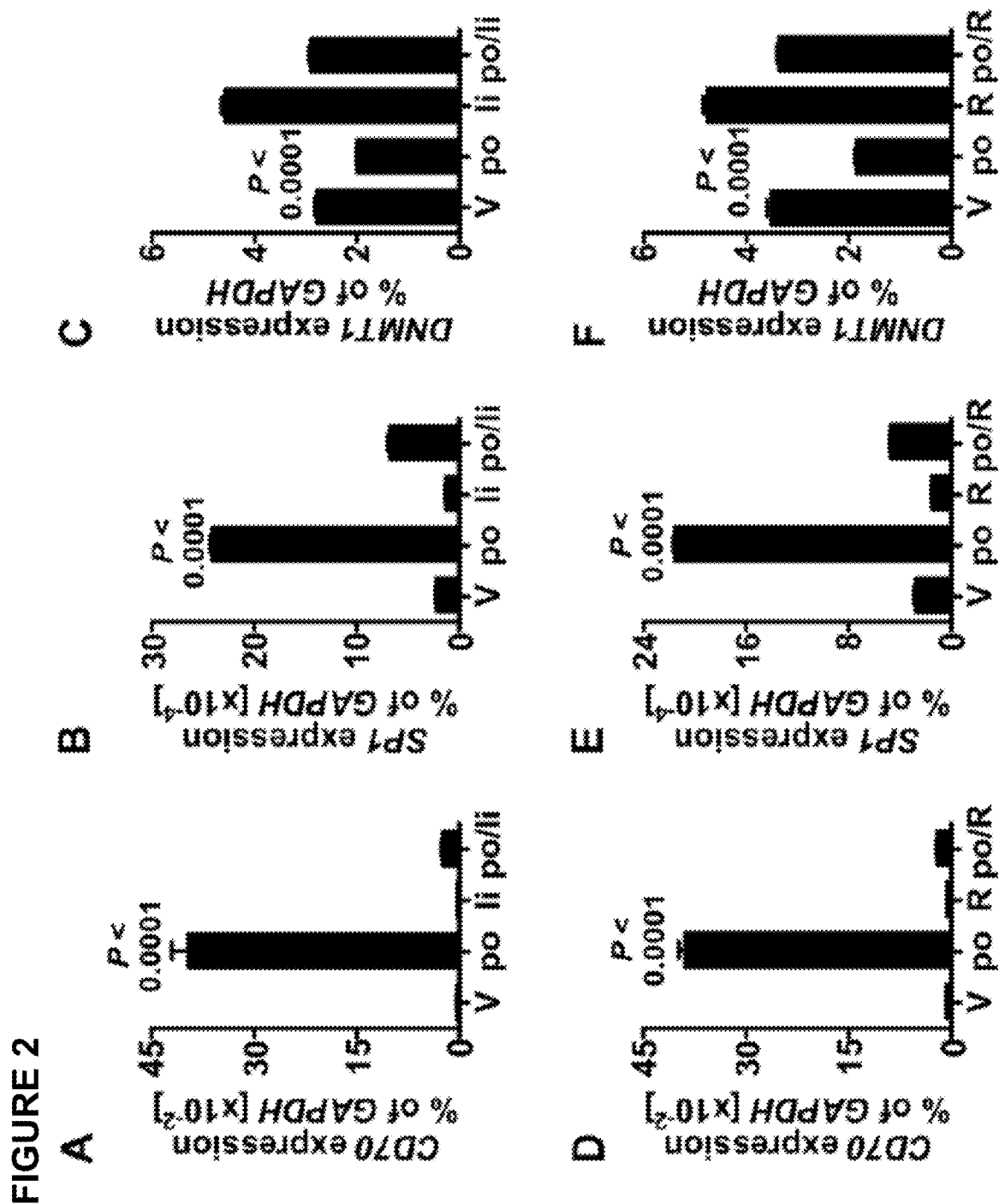

FIG. 2 shows that activation of Wnt signaling by lithium chloride or R-Spondin 1 restores TKI-mediated changes in gene expression. $1\times10^5$ KBM5r cells were cultured in the presence of vehicle, ponatinib (po, 0.1 μM), lithium chloride (li, 10 μM), or both in combination (po/li) for 24 h (A-C). $1\times10^5$ KBM5r cells were cultured in the presence of vehicle, ponatinib (po, 0.1 μM), R-Spondin 1 (R, 10 ng/ml), or both in combination (po/R) for 72 h (D-E). CD70 (A and D), SP1 (B and E), and DNMT1 (C and F) mRNA expression were determined by qRT-PCR. Data from one representative experiment out of two run in duplicates are shown in A-C. Data from one experiment run in duplicates are shown in D-F. Data are displayed as mean±s.e.m. Statistics: one-way ANOVA (all groups vs. po).

(G-K) TKI-mediated BCR-ABL1 inhibition down-regulates miR-29, stimulating SP1 expression and transcription from the CD70 promoter. In G-I, KBM5r cells ($1\times10^5$) were cultured in the presence of vehicle (V; $H_2O$), imatinib (im; 1 μM), nilotinib (ni; 1 μM), or ponatinib (po; 0.1 μM) for 72 hours, and miR29a (G), miR-29b (H), and miR-29c (I) were quantified (qRT-PCR). In (J-K), KBM5r cells ($1\times10^5$) were transfected with anti-miR-29a, anti-miR-29b, anti-miR-29c, or scrambled control (scr) oligonucleotides for 48 hours, and SP1 (J) and DNMT1 (K) mRNA expression were analyzed (qRT-PCR).

(L) shows the methylation status of the CD70 promoter at the SP1 transcription factor binding site (SEQ ID NO: 27) in KBM5r cells upon treatment with vehicle, ponatinib (0.1 μM) or azacytidine (1 μM) as determined by bisulfite sequencing. (M) shows the heat-map of relative quantification of methylated cytosines at five critical CpG sites in the CD70 promoter. (N) shows the semi-quantitative analysis of DNA methylation for CpG1 and CpG2 at the SP1 binding site.

Figure 3:
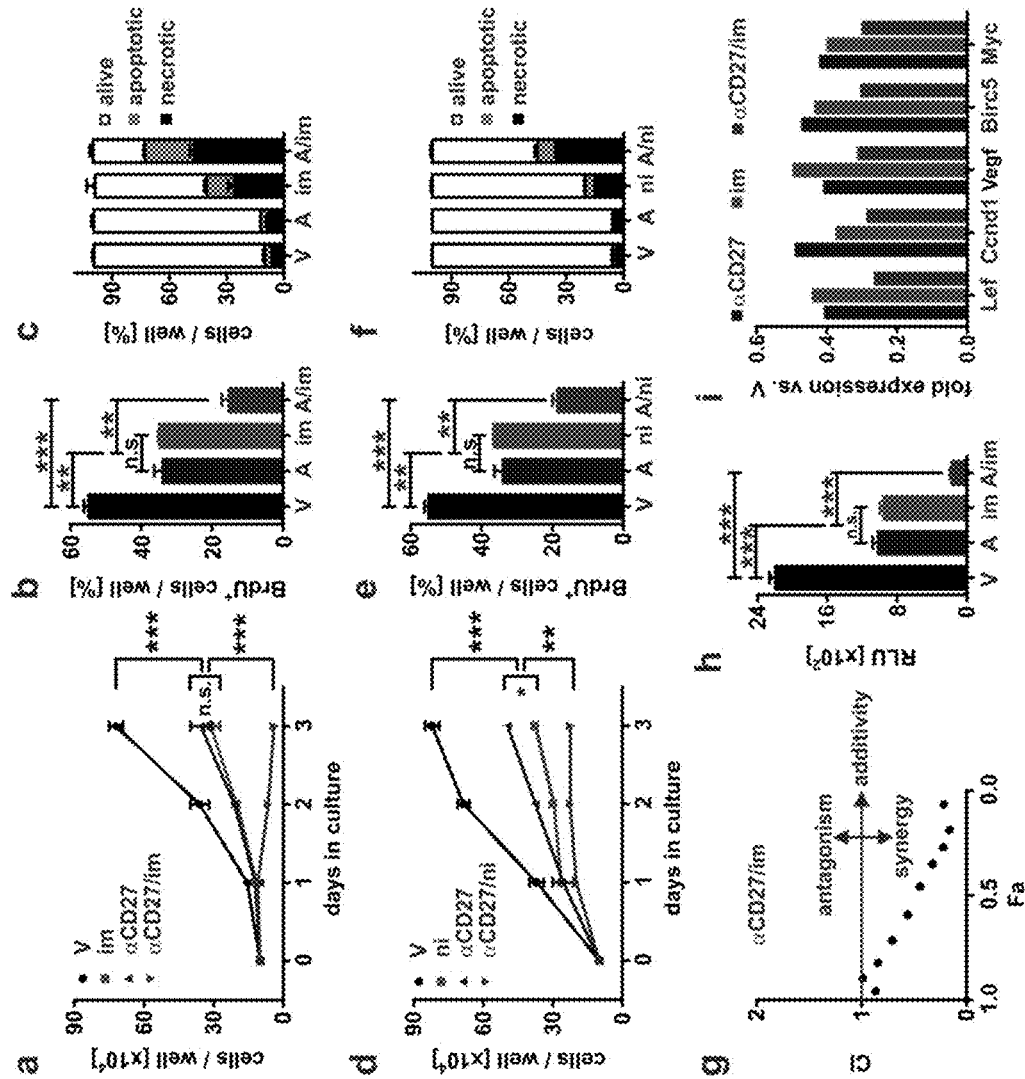

FIG. 3 shows that CD70/CD27 and BCR-ABL1 co-inhibition synergistically eradicates SD-1 leukemia cells. (a-f, h-i) $1\times10^5$ BCR-ABL1+ V SD-1 cells were cultured for 72 h in the presence of either vehicle (V: $H_2O$+IgG), 10 μg/ml of αCD27 blocking mAb (A: $H_2O$+αCD27; clone 15H6), 1 μM of imatinib (im: im+IgG) or 1 μM of nilotinib (ni: ni+IgG) alone or both αCD27/TKI in combination. (a, d) Cell numbers, (b, e) BrdU incorporation and (c, f) cell viability were determined by trypan blue staining and FACS. Apoptotic and necrotic cells were defined as Annexin-V+ and Annexin-V+7-AAD+ cells, respectively. (g) $1\times10^5$ SD-1 cells were treated with either vehicle, αCD27, or imatinib alone or in combination in a constant ratio. Cell numbers per well were counted after 72 h and the effect of drug treatment was calculated as a ratio of vehicle-treated cells. (h-i) Activation of the WNT pathway was assessed using a Tcf/Lef luciferase reporter assay (h) and after 72 h of culture by real-time RT-PCR of selected WNT target genes (i). One representative experiment out of two run in duplicates is shown for each panel. Data are displayed as mean±s.e.m. *p<0.05, p<0.01, *p<0.001. Statistics: (a, d) two-way ANOVA, followed by Bonferroni post-test; (b, e, h) one-way ANOVA.

(j-k) BCR-ABL1 and CD70/CD27 co-inhibition reduces the expansion of KBM5 and KBM5r CML cells in vitro. $1\times10^5$ (j) KBM5 cells or (k) KBM5r cells were cultured for 72 h in the presence of either vehicle (V: $H_2O$+IgG), 10 µg/ml of αCD27 blocking mAb (A: $H_2O$+αCD27; clone 15H6), 1 µM of imatinib (im) or 0.1 µM of ponatinib (po) alone or both in combination (A/im; A/po). Cell numbers were determined by trypan blue staining after 72 h. Data from one experiment run in triplicates are shown. Data are displayed as mean±s.e.m. Statistics: one-way ANOVA.

(l-n) shows the synergy between BCR-ABL1- and CD70/CD27-inhibition. (l) Expression of CD27 and CD70 on SD-1 cells. One representative experiment out of 5 is shown. Isotype controls are blue lines, and CD27 or CD70 stainings are red lines. (m-n) $1×10^5$ SD-1 cells were treated with vehicle, anti-CD27 or imatinib alone or were co-treated in constant ratio combinations. (m) Cell numbers per well were counted after 72 h and the effect of drug treatment was calculated as a ratio of vehicle-treated cells. (n) Isobologram analysis of (m) using the CompuSyn© software at effective doses (ED) 50, 75 and 90. (o) shows that the expression of selected genes involved in stem cell regulation and differentiation (measured by qRT-PCR). The data demonstrate that the Notch, Hedgehog, and MAP (mitogen-activated protein) kinase pathways were unaffected or only minimally affected by the αCD27/imatinib co-treatment.

Figure 4:
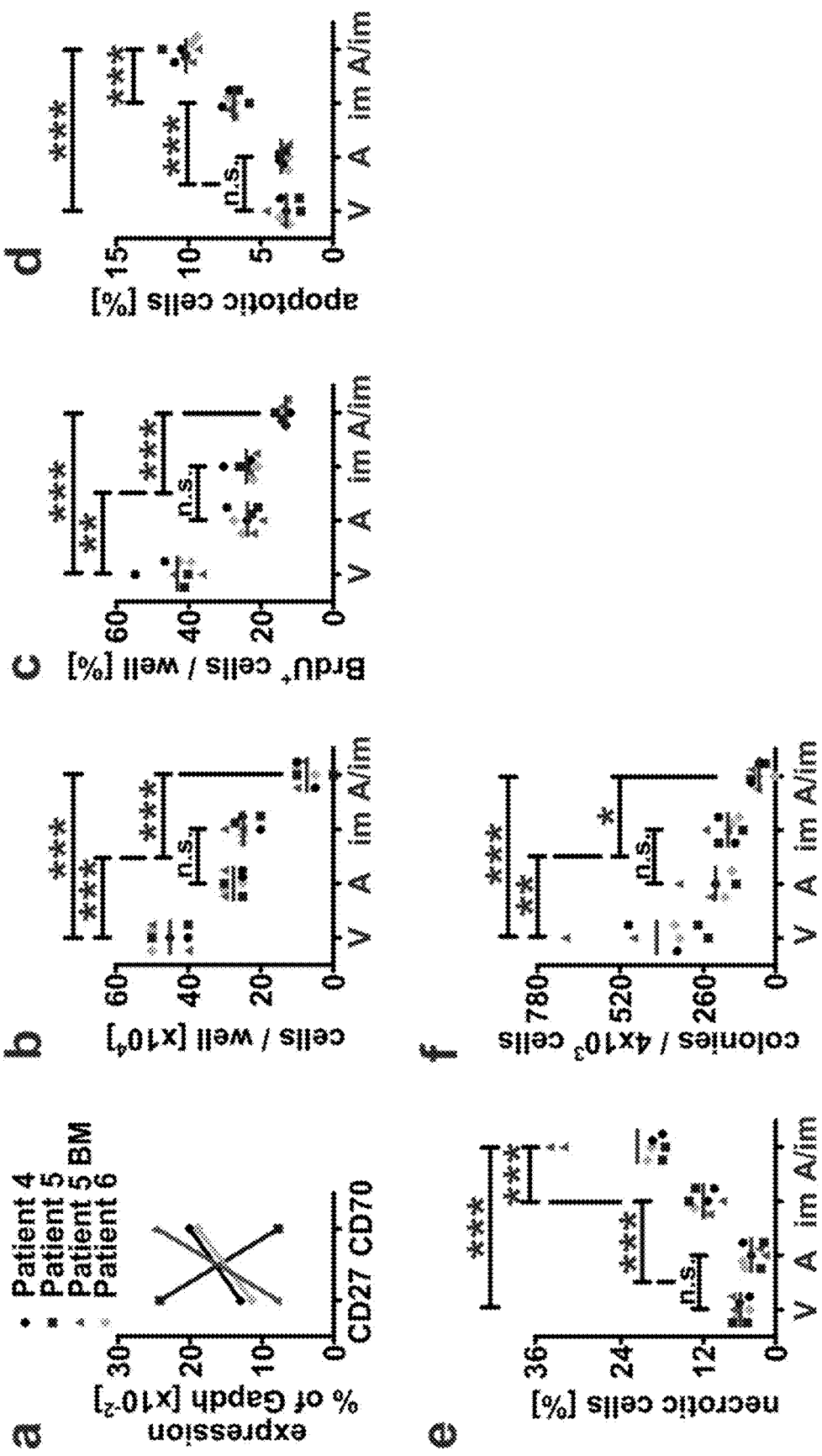

FIG. 4 shows that CD70/CD27 and BCR-ABL1 co-inhibition promotes cell death and inhibits colony formation of CD34$^+$ CML stem/progenitor cells. (a) CD27 and CD70 mRNA expression in FACS-sorted CD34$^+$ cells from blood or BM of newly diagnosed CML patients. (b-e) $1×10^4$ FACS-sorted CD34$^+$ cells were cultured in duplicates in liquid culture medium in the presence of vehicle (V: $H_2O$+IgG), 10 µg/ml of αCD70 blocking mAb (A: $H_2O$+αCD70; clone 41D12-D), 1 µM of imatinib (im: im+IgG) or both in combination (A/im: αCD70+imatinib). (b) Cell numbers, (c) BrdU incorporation and (d-e) cell viability were determined by trypan blue staining and FACS after 7 days. Apoptotic and necrotic cells were defined as Annexin-V$^+$ and Annexin-V$^+$7-AAD$^+$ cells, respectively. (f) Duplicates of $4×10^3$ FACS-sorted CD34$^+$ CML stem/progenitor cells were cultured overnight in 96-well V-bottom plates in the presence of the compounds as described for (b-e) and were then transferred into methylcellulose containing the respective drugs. Colony forming capacity was determined after 14 days by inverted light microscopy. *p<0.05, p<0.01, *p<0.001 (one-way ANOVA).

(g-k) shows that CD70/CD27 and BCR-ABL1 co-inhibition only marginally affects growth and colony formation of human CD34$^+$ stem/progenitor cells from the BM of «healthy donors». (g-j) $1×10^4$ FACS-sorted CD34$^+$ cells from BM aspirates of patients that underwent BM biopsy for other reasons than leukemia («healthy donors») were cultured in duplicates in liquid culture medium in the presence of vehicle (V: $H_2O$+IgG), 10 µg/ml of αCD70 blocking mAb (A: $H_2O$+αCD70; clone 41D12-D), 1 µM of imatinib (im: im+IgG) or both in combination (A/im: αCD70+imatinib). (g) Cell numbers, (h) BrdU incorporation and (i-j) cell viability were determined by trypan blue staining and FACS after 7 days. Apoptotic and necrotic cells were defined as Annexin-V$^+$ and Annexin-V$^+$7-AAD$^+$ cells, respectively. (k) Duplicates of $4×10^3$ FACS-sorted CD34$^+$ cells were cultured overnight in V-bottom plates in the presence of the compounds as described for (g-j) and were then transferred into methylcellulose containing the compounds. Colony forming capacity was determined after 14 days by inverted light microscopy. *p<0.05, p<0.01, *p<0.001 (one-way ANOVA).

Figure 5:
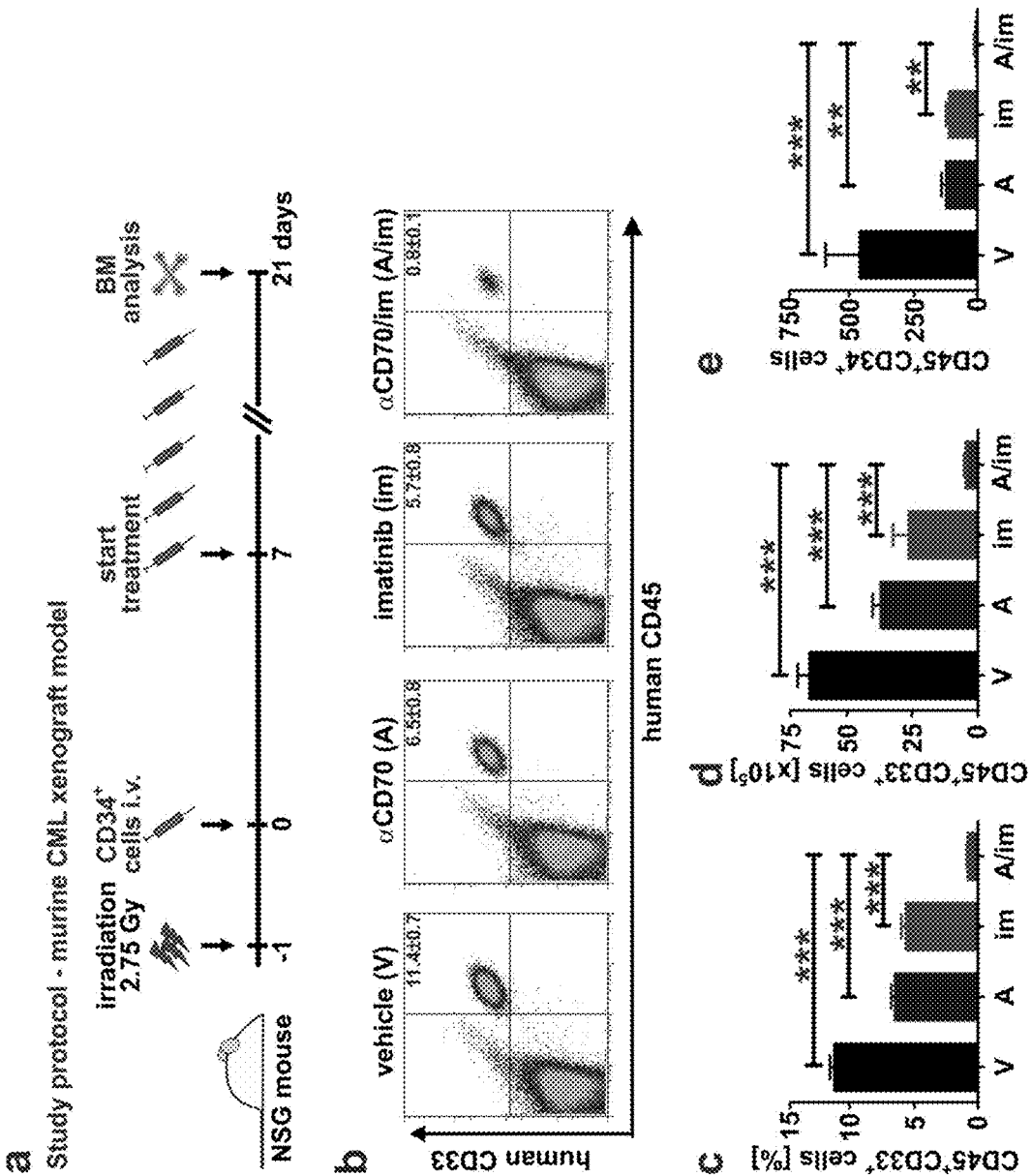

FIG. 5 shows that αCD70 mAb/imatinib combination therapy synergistically eradicates human CD34$^+$ CML stem/progenitor cells in xenografts in vivo. (a) Study design. $2×10^6$ CD34$^+$ stem/progenitor cells from the peripheral blood of a newly diagnosed CML patient were injected intravenously into previously sublethally irradiated (2.75 Gy) NSG mice. Starting one week after transplantation, imatinib (50 mg/kg) was administered once daily by oral gavage. 10 mg/kg of αCD70 blocking mAb (clone 41D12-D) was administered intraperitoneally every 3$^{rd}$ day. Sterile $H_2O$ and a control mAb specific for the F protein of respiratory syncytial virus (Pavilizumab, Synagis®) were used as mock-treatment. After 2 weeks of treatment, mice were euthanized and BM was analyzed for human cells by FACS. (b) Representative dot plots. (c) Frequencies and (d) absolute numbers of human CD45$^+$CD33$^+$ CML myeloid cells and (e) absolute numbers of human CD45$^+$CD34$^+$ CML stem/progenitor cells in the BM of NSG mice. Data are displayed as mean±s.e.m. *p<0.05, p<0.01, *p<0.001 (one-way ANOVA).

(f) MFI of CD70 expression on CD45$^+$ CD34$^-$ CML cells and CD45$^+$ CD34$^+$ CML stem/progenitor cells in xenografted NSG mice (n=3 per xenograft and per treatment). (g-l) CD70 (g), SP1 (h), DNMT1 mRNA (i), and miR-29 expression (j-l) (qRT-PCR) in CD34$^+$ cells. (n-m) Correlation of CD70 expression with the expression of selected Wnt target genes RUNX1 (m) and WISP1 (n) in CD34$^+$ stem/progenitor cells from newly diagnosed chronic phase CML patients. Expression data are derived from a public repository for microarray data and are available under accession number E-MEXP-480 (EMBL EBI Arrayexpress). Data are displayed as means±SEM. Statistics: (c-e), one-way ANOVA; (f-l), Student's t test; (m) and (n), Spearman correlation.

(o) Imatinib concentration was measured in the plasma of xenografted CML mice. CD34$^+$ stem/progenitor cells from the blood of three newly diagnosed CML patients (3, 4, and 5, Table 1) were injected intravenously into irradiated (2.75 Gy) NSG mice. Starting one week after transplantation, imatinib (im, 50 mg/kg) or vehicle was administered once daily by oral gavage. Imatinib concentrations were determined in plasma two weeks later.

(p-r) CD70 and CD27 expression were determined on primary human CML cells. CD34$^+$ stem/progenitor cells from the blood of a newly diagnosed CML patient were injected intravenously into irradiated (2.75 Gy) NSG mice. Starting one week after transplantation, imatinib (im, 50 mg/kg) or vehicle was administered once daily by oral gavage. After 2 weeks of treatment, mice were euthanized and CML cells were analyzed for the expression of CD70 and CD27 by FACS. Histogram of (p) CD70 and (q) CD27 expression on CD45+CD34+ CML stem/progenitor cells and (r) MFI of CD27 expression on CD45$^+$CD34$^-$ CML cells and CD45$^+$CD34$^+$ CML stem/progenitor cells ex vivo from xenografted NSG mice (n=6 per group). (p-q) red lines, CD70 and CD27 antibodies; blue lines, respective isotype controls. Data are displayed as mean±s.e.m.

Figure 6:
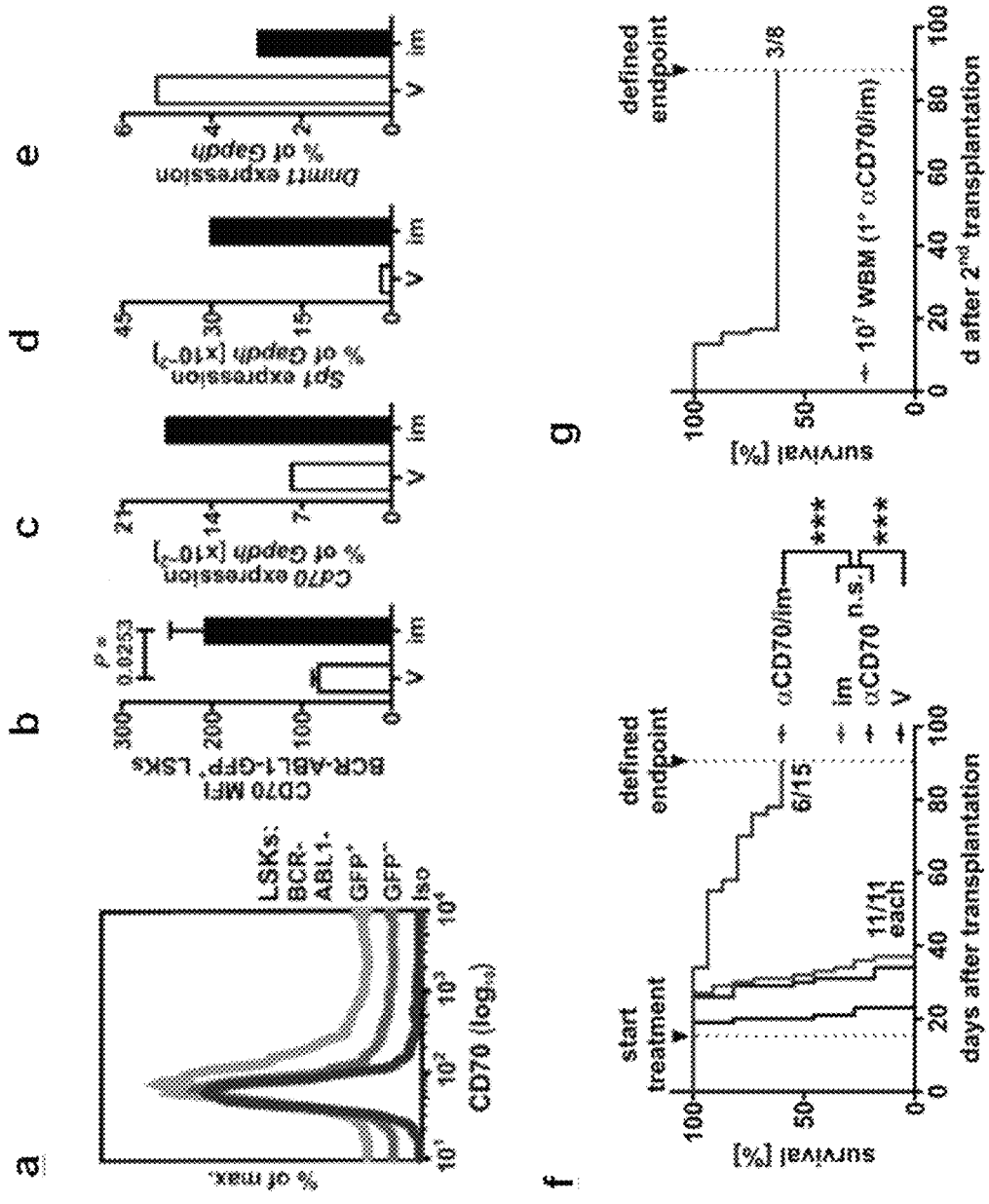

FIG. 6 shows that αCD70 mAb/imatinib combination treatment eradicates LSCs and promotes long-term survival of CML mice.

(a-e) BL/6 CML mice were treated with vehicle ($H_2O$, n=5) or imatinib (50 mg/kg) (im; n=7) once daily by oral gavage starting 15 days after transplantation. Ten days later, CD70 protein expression was analyzed by FACS in BCR-ABL1-GFP$^+$ LSKs and endogenous GFP$^-$ LSKs. (a) Representative histograms. (b) MFI. CD70 (c), Sp1 (d), and Dnmt1 (e) mRNA expression in FACS-sorted, pooled BCR-ABL1-GFP+ LSKs (qRT-PCR).

(f) Kaplan-Meier survival curves of primary BL/6 CML mice. Starting 15 days after transplantation, imatinib (50 mg/kg) was administered once daily by oral gavage. 300 μg of αCD70 blocking mAb (clone FR70) were administered intraperitoneally every $3^{rd}$ day. Sterile $H_2O$ and IgG from rat serum were used as mock-treatment. Pooled data from 2 independent experiments with n=11-15 mice per group are shown. (g) Survival of lethally irradiated (2×6.5 Gy) secondary recipients (n=8) that received 1×10$^7$ whole BM (WBM) cells from co-treated primary CML mice (n=8) that were still alive 90 days after primary transplantation. (h-k) Primary BL/6 CML mice were treated with either imatinib alone or were co-treated as described in (f) starting 15 days after transplantation. Ten days later, numbers of (h) BCR-ABL1-GFP$^+$ LSKs, (i) BCR-ABL1-GFP$^+$ LT-LSCs and (j) BCR-ABL1-GFP$^+$ ST-LSCs were determined in the BM. (k) Equal numbers of total lin$^-$ cells were plated in methylcellulose and BCR-ABL1-GFP$^+$ colonies were enumerated 7 days later by inverted fluorescence microscopy. (l) Primary BL/6 CML mice were treated with either imatinib alone or in combination with αCD70 mAb as described in (f) starting 15 days after transplantation. Ten days later, 3×10$^6$ WBM cells from imatinib or αCD70 mAb/imatinib treated animals were transplanted into sublethally irradiated (4.5 Gy) recipient mice (n=5-6 per group) and survival was monitored. (f, g, l) Numbers of mice that succumbed to CML of total transplanted mice are indicated. Data are displayed as mean±s.e.m. *p<0.05, p<0.01, *p<0.001 (log-rank test, student's t-test).

(m) CD70 expression on murine LSCs and endogenous non-malignant GFP−LSKs was evaluated after imatinib treatment. BL/6 CML mice were treated with vehicle (V: $H_2O$, n=5) or imatinib (im, 50 mg/kg, n=7) once daily by oral gavage starting 15 days after transplantation. 10 days later, the LSC-containing BCR-ABL1-GFP+ LSKs and the endogenous HSC-containing GFP− LSKs were analyzed for CD70 expression by FACS. One representative example of n=5-7 mice is shown. Red lines, CD70 staining; blue lines, isotype control.

(n-w) TKI treatment induces CD70 expression on murine LSCs but not on leukemia progenitors or endogenous non-malignant GFP− LSKs. BL/6 CML mice were treated with vehicle (V: H2O, n=5) or imatinib (im, 50 mg/kg, n=7) once daily by oral gavage starting 15 days after transplantation. 10 days later, the BCR-ABL1-GFP+c-kit$^{hi}$Sca-1− leukemia progenitors, the LSC-containing BCR-ABL1-GFP+ LSKs, and the endogenous HSC-containing GFP− LSKs were analyzed. (n, o) MFI of CD70 protein expression (FACS) on (n) BCR-ABL1-GFP+c-kit$^{hi}$Sca-1$^-$ leukemia progenitor cells and (o) endogenous GFP− LSKs. (p) Cd70, (q) Sp1, and (r) Dnmt1 mRNA expression in FACS-sorted endogenous GFP− LSKs pooled from n=5-7 mice (qRT-PCR). (s) Cd27, (t) Traf2, (u) Tnik, (v) Runx1, and (w) Myc mRNA expression in FACS-sorted BCR-ABL1-GFP$^+$ LSKs pooled from n=5-7 mice (qRT-PCR). Data are displayed as mean±s.e.m. Statistics: Student's t-test.

Figure 7:
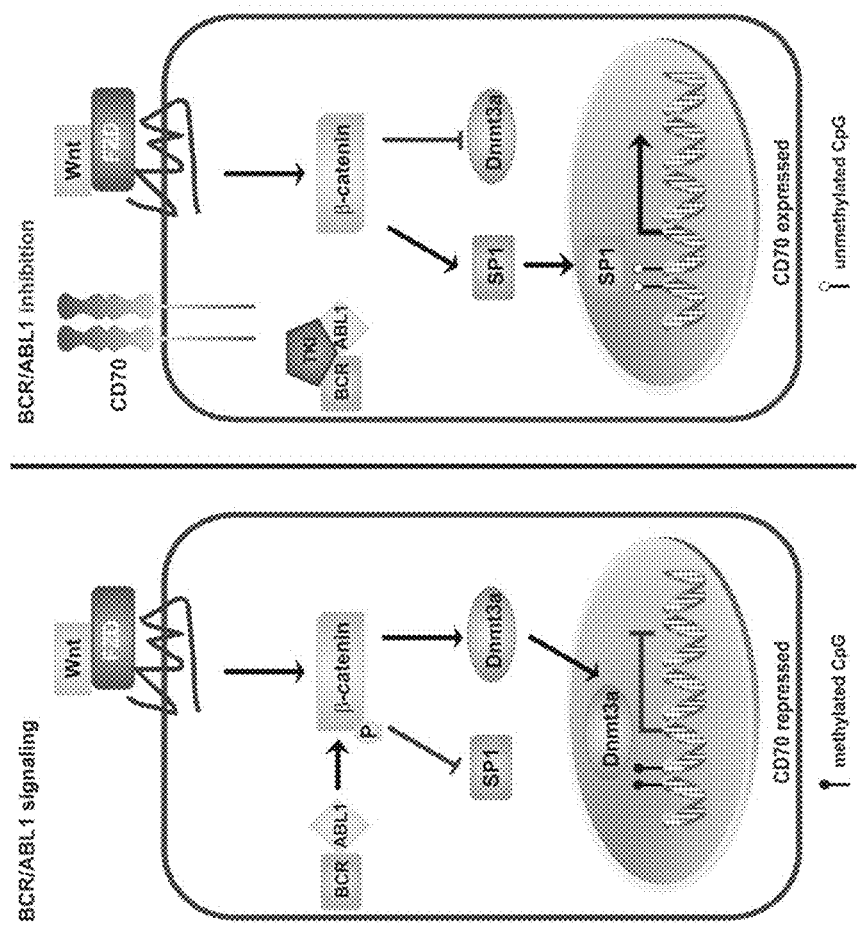

FIG. 7 depicts a schematic representation of WNT activation in TKI resistant CML LSCs. Constant signaling via β-catenin sustaining permanent WNT pathway activation is crucial for LSC survival and maintenance. In the absence of WNT signals that are transduced via the Frizzled (FZD) receptor, β-catenin is unstable and gets degraded in the proteasome. In CML, β-catenin is constantly kept stable via BCR-ABL1-mediated tyrosine phosphorylation. In addition, CD27 signaling induces WNT activation in LSCs via TRAF2 and TNIK. Upon treatment with BCR-ABL1 TKIs, β-catenin is no longer stabilized by BCR-ABL1 tyrosine kinase activity. However, TKI-mediated BCR-ABL1 inhibition represses Dnmt mRNA expression leading to reduced methylation of the CD70 promoter. Furthermore, TKI treatment induces SP1 mRNA expression. Binding of SP1 to a de-methylated CD70 promoter increases CD70 mRNA and protein expression. Autocrine CD70/CD27 signaling on LSCs triggers a feedback loop that keeps the WNT pathway active and sustains LSC survival even in the presence of BCR-ABL1 TKIs. Blocking the CD70/CD27-interaction in conjunction with BCR-ABL1 TKI treatment inhibits the WNT pathway and eradicates LSCs.

Figure 8:
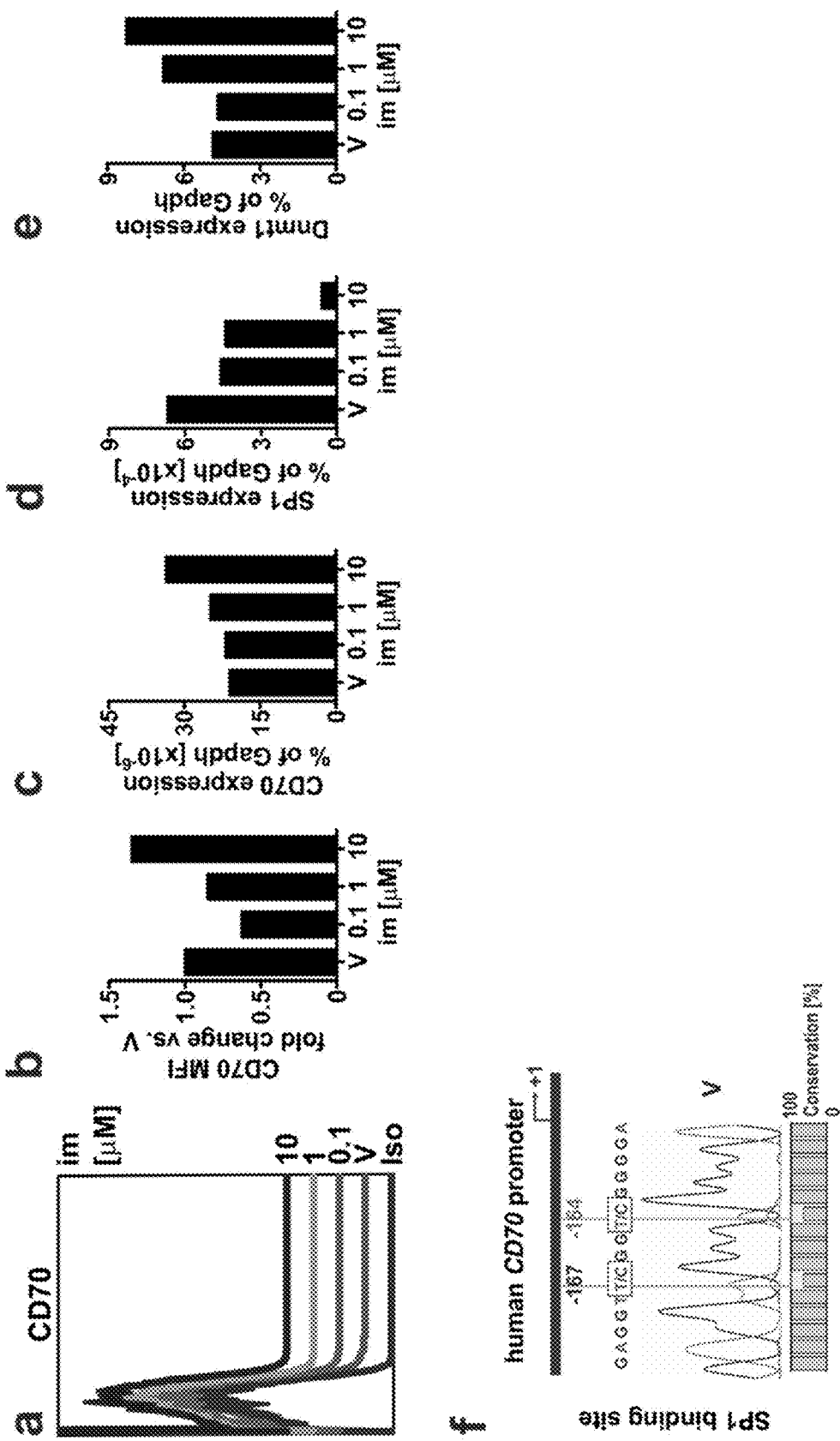

FIG. 8 shows that TKI-induced CD70 up-regulation is mediated via BCR-ABL1 inhibition. (a-e) 1×10$^5$ imatinib-resistant KBM5r cells were cultured in 24-well tissue culture plates in the presence of vehicle or imatinib (im) at the indicated concentrations for 72 h. (a) Histograms and (b) mean fluorescence intensity (MFI) of CD70 protein expression (FACS). (c) CD70, (d) SP1, and (e) Dnmt1 mRNA expression (real-time RT-PCR). (f) Methylation status of the CD70 promoter at the SP1 transcription factor binding site (SEQ ID NO: 27) of vehicle-treated KBM5 cells as determined by bisulfite sequencing. Data are displayed as mean±s.e.m.

Figure 9:
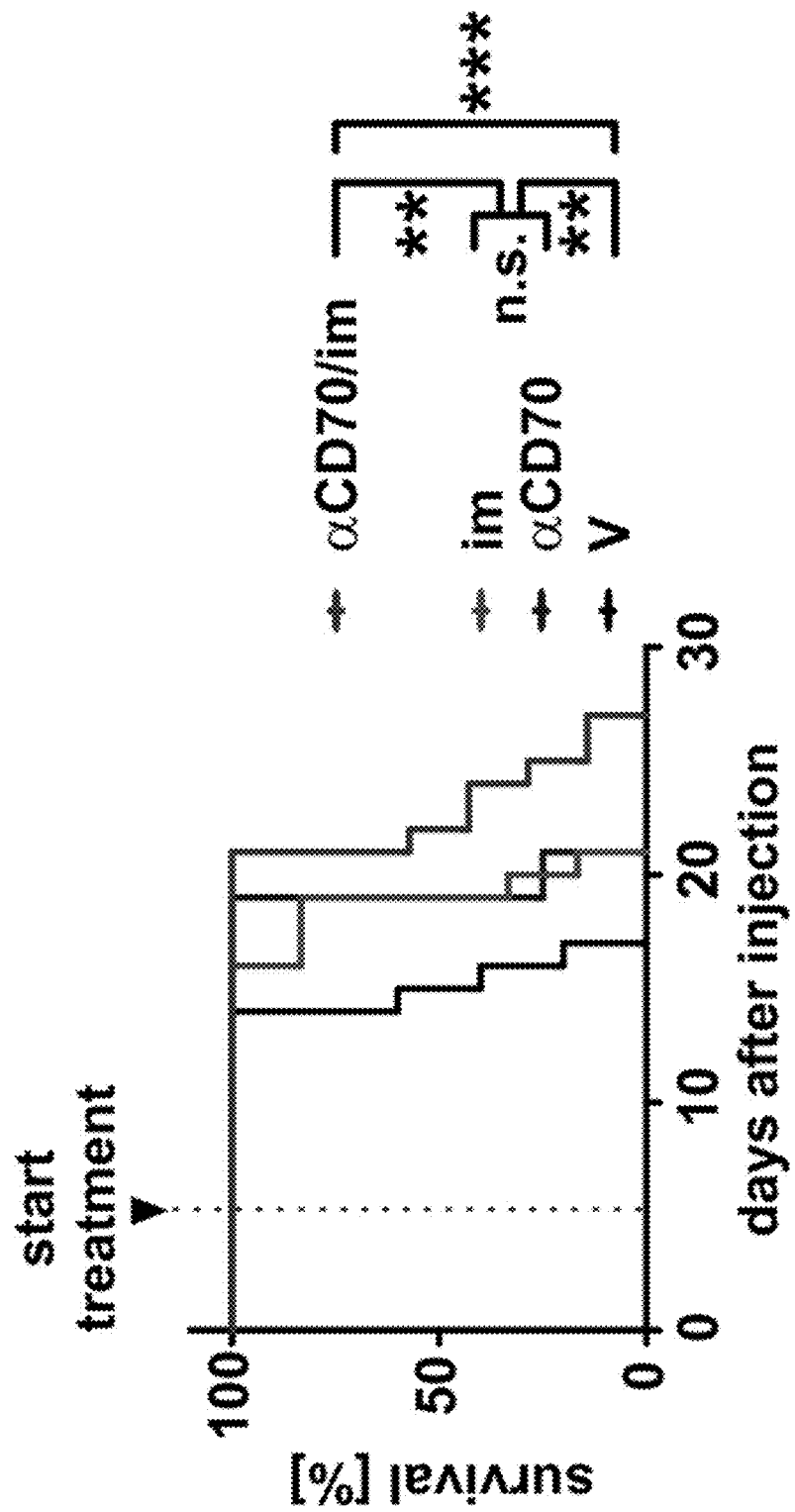

FIG. 9 shows that co-treatment significantly prolongs survival in a highly aggressive SD-1 xenotransplantation model. 1×10$^5$ SD-1 cells were injected intravenously into previously sublethally irradiated (2.75 Gy) NSG mice. Starting one week after transplantation, imatinib (50 mg/kg) was administered once daily by oral gavage. 10 mg/kg of αCD70 blocking mAb (clone 41D12-D) was administered intraperitoneally every $3^{rd}$ day. Sterile $H_2O$ and a control mAb specific for the F protein of respiratory syncytial virus (Pavilizumab, Synagis®) were used as mock-treatment. Mice were monitored and euthanized when showing signs of leukemia. Pooled data from 2 independent experiments with n=4-7 mice per group are shown. p<0.01, *p<0.001 (log-rank test).

Figure 10:
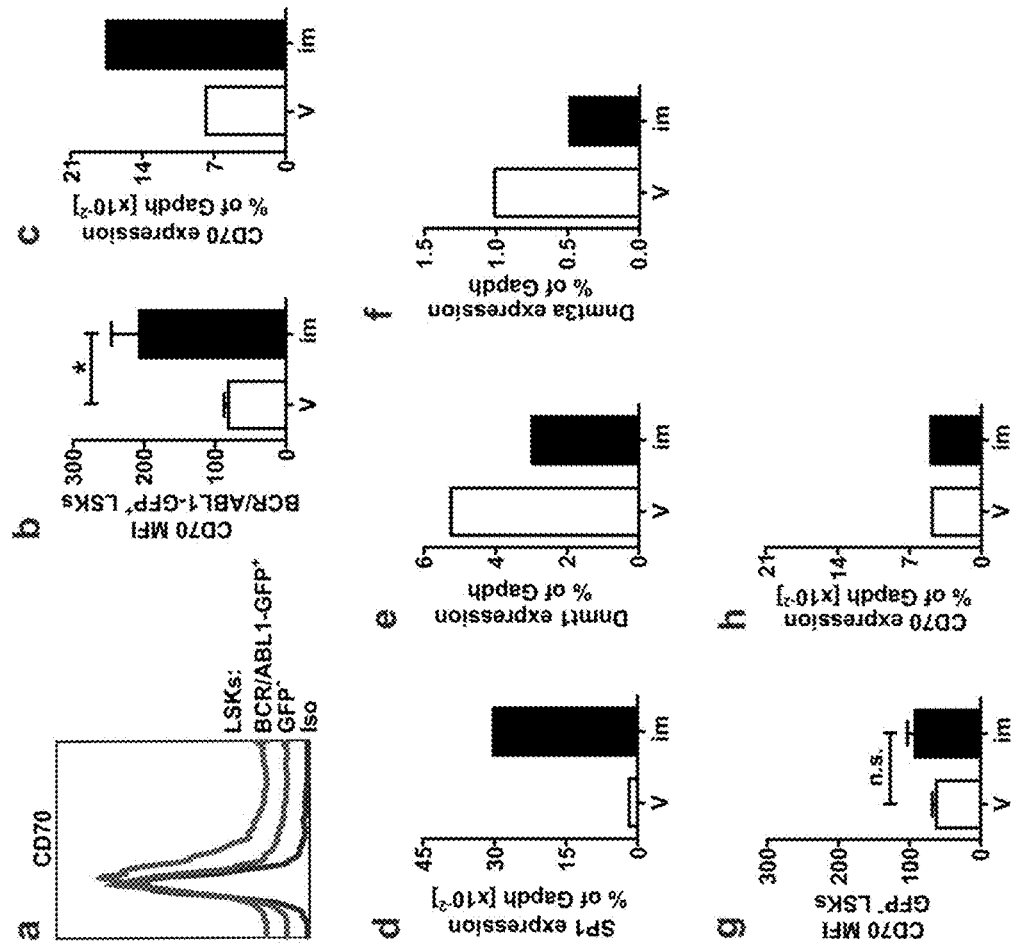

FIG. 10 shows that TKIs up-regulate CD70 on murine LSCs but not endogenous HSCs. BL/6 CML mice were treated with vehicle (V: H2O) or 50 mg/kg of imatinib (im) starting 15 days after transplantation. Ten days later, the LSC-containing BCR-ABL1-GFP+ LSKs and the endogenous HSC-containing GFP− LSKs were analyzed. (a) Histograms and (b, g) mean fluorescence intensity (MFI) of CD70 protein expression as determined by FACS of (a-b) BCR-ABL1-GFP+ LSKs and (a, g) endogenous GFP− LSKs. (c) CD70, (d) SP1, (e) Dnmt1 and (f) Dnmt3a mRNA expression in FACS-sorted BCR-ABL1-GFP+ LSKs and (h) CD70 mRNA expression in FACS-sorted GFP− LSKs as analyzed by real-time RT-PCR.

Figure 11:
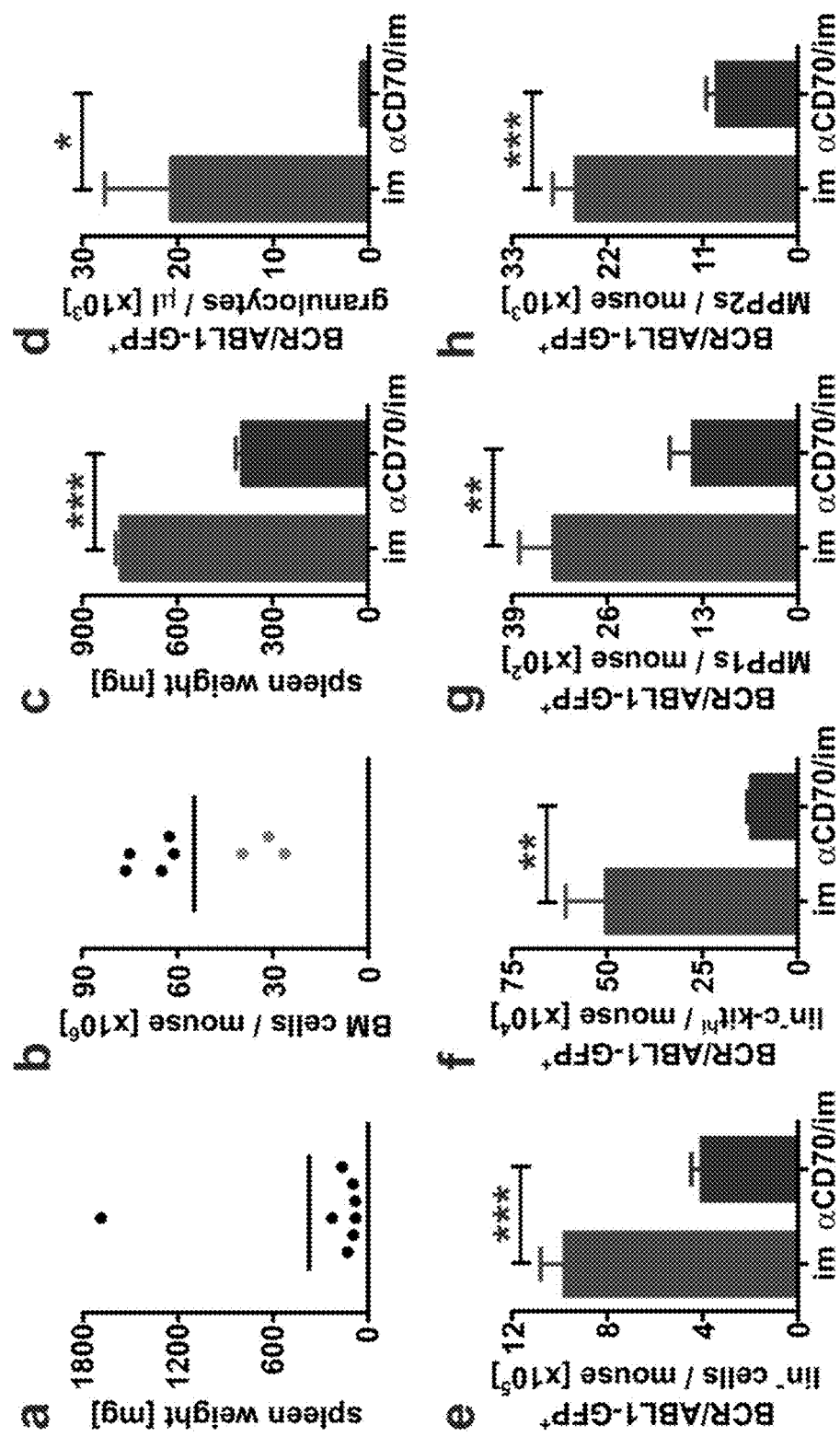

FIG. 11 shows that co-treatment eradicates LSCs and promotes long-term survival of CML mice. (a) Spleen weights and (b) total BM cell numbers of co-treated CML mice that were still alive 90 days after primary transplantation. The grey dots in (b) indicate mice with higher residual disease load (11%, 53% and 74% BCR-ABL1-GFP$^+$ BM cells, respectively; data not shown) that led to death upon secondary transplantation into lethally irradiated (2×6.5 Gy) recipient mice (see FIG. 5b). (c-h) Primary BL/6 CML mice were either treated with 50 mg/kg imatinib (im) daily by oral gavage or were co-treated with imatinib and 300 μg of αCD70 blocking (clone FR70) intraperitoneally every $3^{rd}$ day (αCD70/im) starting 15 days after transplantation. Sterile $H_2O$ and IgG from rat serum were used as mock-treatment. After ten days of treatment, (c) spleen weights, (d) numbers of BCR-ABL1-GFP$^+$ Gr-1$^+$ granulocytes in peripheral blood and numbers of (e) BCR-ABL1-

GFP⁺lin⁻ leukemia cells, (f) BCR-ABL1-GFP⁺lin⁻c-kit$^{hi}$ leukemia progenitors and (g-h) BCR-ABL1-GFP⁺lin⁻c-kit$^{hi}$ leukemia multipotent progenitors (MPPs) in the BM were determined by FACS. Data are displayed as mean±s.e.m. *p<0.05, p<0.01, *p<0.001 (student's t-test).

Figure 12:
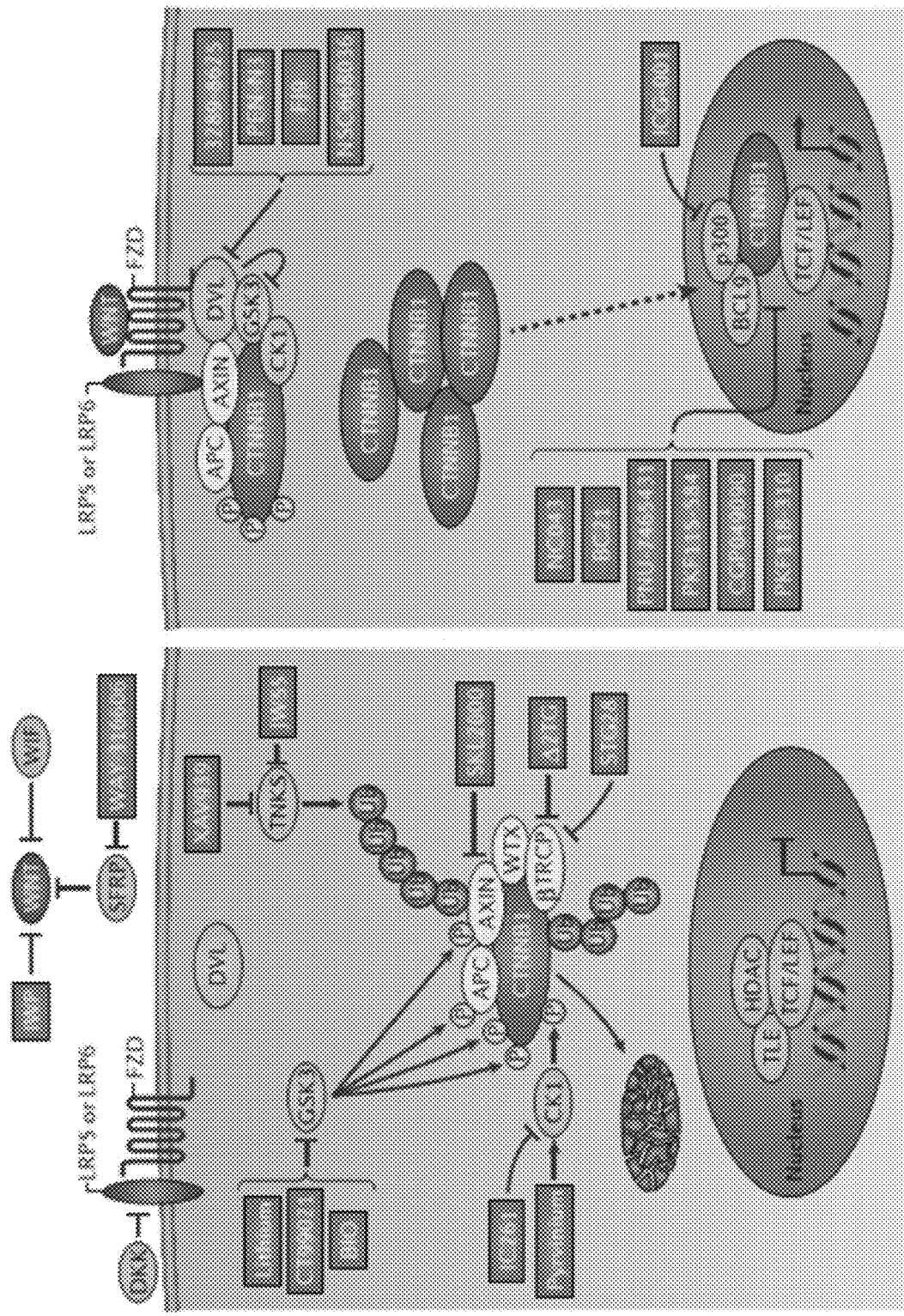

FIG. 12 provides a schematic representation of the canonical and non-canonical WNT/β-catenin (CTNNB1) signaling pathways. The WNT-CTNNB1 signaling pathway. β-catenin (CTNNB1)-dependent WNT signaling pathways have crucial roles in the regulation of diverse cell behaviors, including cell fate, proliferation, survival, differentiation, migration and polarity. Small-molecule inhibitors and activators of various pathway components are indicated in this figure in boxes. In the absence of WNT stimulation, a destruction complex, containing the proteins adenomatous polyposis coli (APC), glycogen synthase kinase 33 (GSK33) and AXIN, phosphorylates (P) and targets CTNNB1 for ubiquitylation (Ub) and proteasomal degradation. In the absence of WNTs, members of the TCF/LEF family of high-mobility-group transcription factors associate in a repressive complex with transducin-like enhancer protein (TLE; also known as Groucho) co-repressor proteins, which promote the recruitment of histone deacetylases (HDACs) to repress CTNNB1 target genes. b | The binding of WNTs, such as WNT3A and WNT1, to frizzled (FZD) and LRP5 or LRP6 co-receptors transduces a signal across the plasma membrane that results in the activation of the Dishevelled (DVL) protein. Activated DVL inhibits the destruction complex, resulting in the accumulation of CTNNB1, which then enters the nucleus where it can act as a co-activator for TCF/LEF-mediated transcription. CTNNB1 acts on a transcriptional switch, as the presence of CTNNB1 reduces the association of TLE with TCF/LEF, while recruiting various transcriptional cofactors including BCL9, Pygopus and histone acetyltransferases. WNT-CTNNB1-dependent transcription ultimately modulates changes in cell behaviors such as proliferation, survival and differentiation. CK1, casein kinase 1; DKK dickkopf homologue; SFRP, secreted frizzled-related protein; TNKS, tankyrase; 3TRCP, 3-transducin repeat-containing E3 ubiquitin protein ligase; WIF, WNT inhibitory factor; WTX, Wilms tumour gene on the X chromosome.

Figure 13:
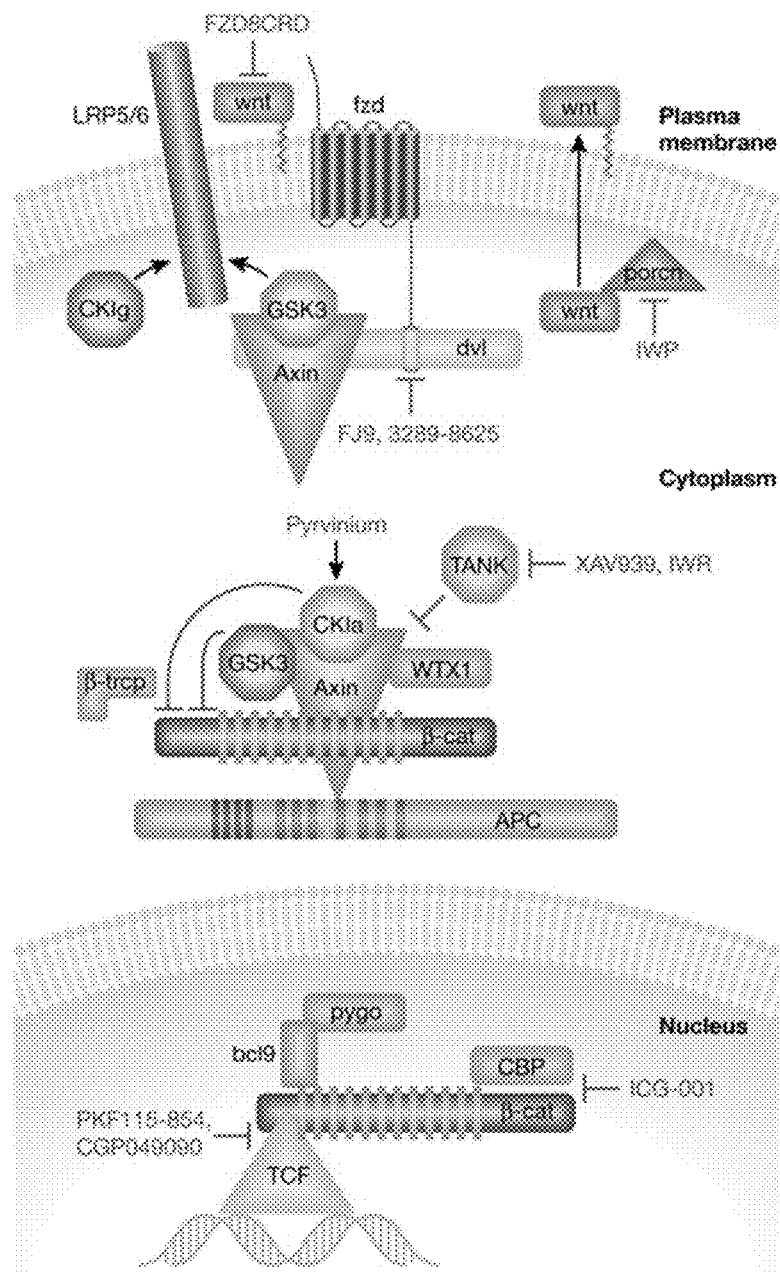

FIG. 13 shows a schematic of the current therapeutic intervention in WNT signaling. Components of WNT signaling at the plasma membrane (PM), in the cytoplasm and nucleus are represented with the locus of intervention for some of the inhibitors (text adjacent to bar-headed lines) described in section 5 (cited from Polakis EMBO J. (2012) 31, Issue 12, pp 2664-2832).

Figure 14:
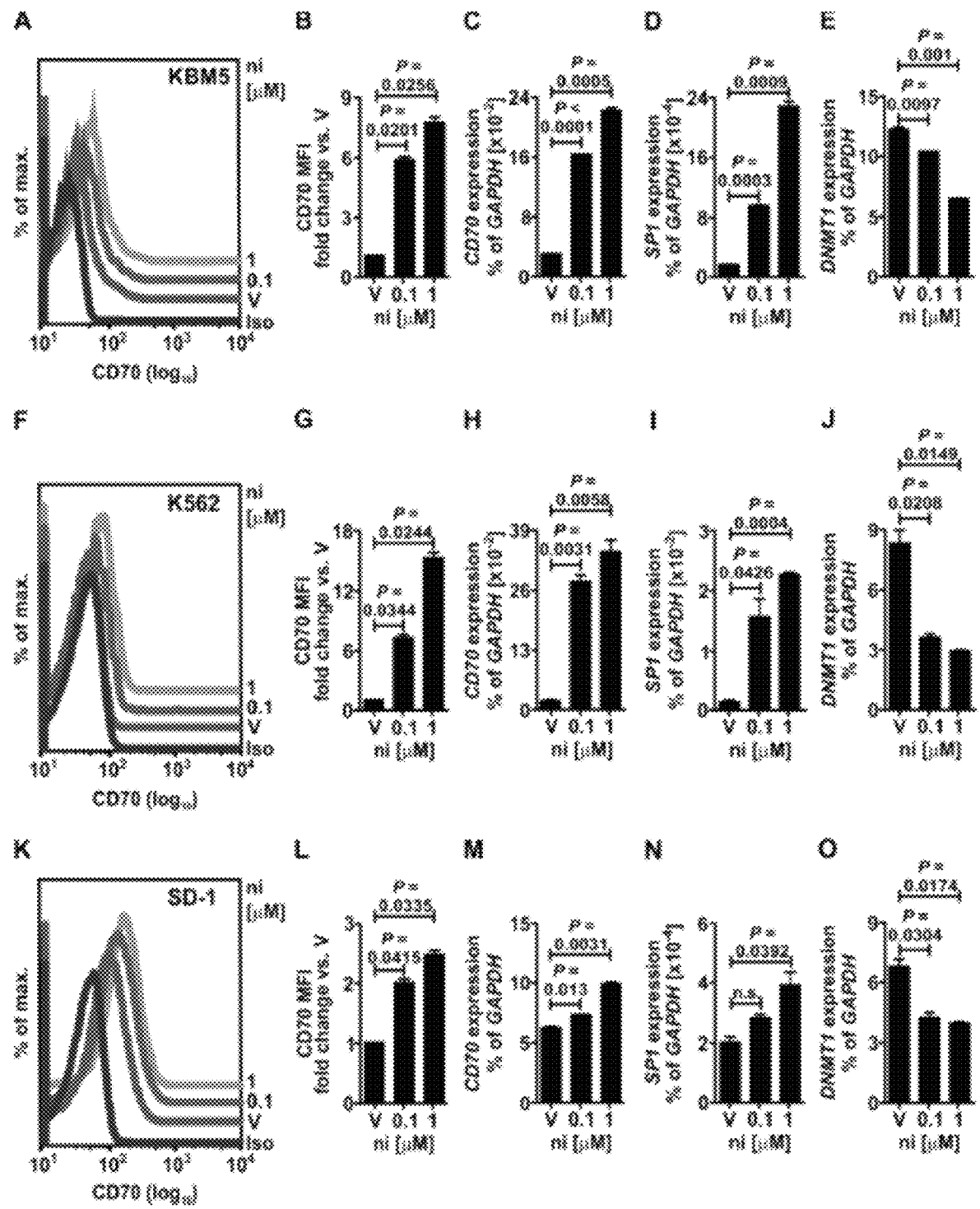

FIG. 14: TKI treatment induces CD70 expression on human BCR-ABL1+ leukemia cell lines (KBM5, K562, or SD-1 cells). 1×10⁵ KBM5, K562, or SD-1 cells were cultured for 72 h in the presence of vehicle (V: H₂O) or the second-generation TKI nilotinib (ni) at the indicated concentrations. Histograms (A, F and K) and mean fluorescence intensity (MFI) (B, G and L) of CD70 protein expression for each cell line (FACS). CD70 (C, H, and M), SP1 (D, I, and N), and DNMT1 (E, J and O) mRNA expression for each cell line (qRT-PCR). Pooled data from two independent experiments run in duplicates are shown. Data are displayed as mean±s.e.m. Statistics: (B, G, and L), one-sample t-test (hypothetical value 1); (C-E, H-J and M-O), student's t-test.

DETAILED DESCRIPTION

The present disclosure provides compositions and methods for treating a subject suffering from a BCR-ABL1 related disorder (e.g., chronic myelogenous leukemia). The methods disclosed herein generally comprise administering to the subject an effective amount of a therapeutic combination of a WNT signaling pathway inhibitor and a BCR-ABL1 tyrosine kinase inhibitor. Such methods are based, in part, on the surprising discovery that a BCR-ABL1 tyrosine kinase inhibitor and CD70/CD27 inhibitor act synergistically to eradicate leukemia cells in vitro and in vivo. The methods and compositions disclosed herein are particularly useful for treating a chronic myelogenous leukemia that is resistant to a BCR-ABL1 tyrosine kinase inhibitor.

1) Definitions

Certain terms used herein are described below. Compounds and antibodies of the present invention are described using standard nomenclature. Unless defined otherwise, all technical and scientific terms used herein have the same meaning as is commonly understood by one of skill in the art to which this invention belongs.

The meaning and scope of the terms should be clear, however, in the event of any latent ambiguity, definitions provided herein take precedence over any dictionary or extrinsic definition. Further, unless otherwise required by context, singular terms shall include pluralities and plural terms shall include the singular. Generally, nomenclature used in connection with, and techniques of, cell and tissue culture, molecular biology, immunology, microbiology, genetics and protein and nucleic acid chemistry and hybridization described herein are those well-known and commonly used in the art.

In order that the present invention may be more readily understood, certain terms are first defined.

The terms "a" and "an" and "the" and similar references in the context of describing the invention (especially in the context of the following claims) are to be construed to cover both the singular and the plural, unless otherwise indicated herein or clearly contradicted by context. Where the plural form is used for compounds, salts, and the like, this is taken to mean also a single compound, salt, or the like.

The term "WNT" as used herein refers to members of the family of secreted glycoproteins that interact with Frizzled family members and/or LRP5/LRP6 co-receptor to activate intracellular signaling cascades. The term includes proteins related in sequence to human WNT1 (NCBI Accession No. P04628) but is not limited to human WNT proteins. Thus, the term includes homologues of WNT family proteins found in all animals. In some embodiments, "WNT" refers to one of the 19 WNT proteins identified including, but not limited to, WNT1, WNT2, WNT2B/13, WNT3, WNT3A, WNT4, WNT5A, WNT5B, WNT6, WNT7A, WNT7B, WNT8A, WNT8B, WNT9A (previously WNT14), WNT9B (previously WNT15), WNT10A, WNT10B, WNT11, and WNT16.

The term "WNT signaling pathway" as used herein refers to cellular signaling cascades mediated by WNT proteins. It includes all components of the transduction cascade, including the WNT protein itself, cell surface receptor complex, intracellular signaling proteins, and transcriptional regulators. This term is not limited to the human WNT pathway proteins, but includes homologues of WNT pathway components found in all animal models.

The term "inhibition" in the context of a signaling pathway refers to any reduction in signaling to below wild type levels in a given context. Inhibition may be partial or complete depending upon the specific context.

The term "inhibition of WNT signaling" as used herein refers to reduction of WNT-mediated signal transduction to below wild type levels. Inhibition may occur at any point in the pathway including but not limited to WNT transcription, translation, folding, post-translational modification, secretion, ligand-receptor binding, intracellular signal transmission, and transcriptional activation of WNT target genes. A WNT signaling inhibitor includes, but is not limited to, for example, Porcupine inhibitors, tankyrase inhibitors, Frizzled antibodies and LRP6 antibodies.

"CD70" or "CD27L" (also known as TNFSF7, CD27LG, Ki-24) is a type II integral membrane protein whose expression on normal tissues is highly restricted to a subset of activated T and B cells, dendritic cells and to a small subset of cells in the thymic epithelium. The biological functions of CD27L, which include augmentation or regulation of the immune response, are mediated via binding to its receptor, CD27, which is expressed predominately on lymphoid cells. CD27L/CD27 interactions regulate B-cell proliferation and differentiation and T-cell costimulation/activation.

A "CD70 inhibitor" denotes an agent that reduces or attenuates the activity level of the CD70 antigen expressed on cells including activated B cells, T lymphocyte cells, and APCLP cells. Such inhibition can result from a variety of events, such as the interrupted binding of the CD70 antigen to an appropriate receptor, inactivating the CD70 antigen, such as by cleavage or other modification, altering the affinity or CD70 to its ligand or receptor, preventing or reducing the expression of CD70 on a cell, expressing an abnormal or inactive CD70 antigen, or deactivating the antigen, preventing or reducing the proper conformational folding of the CD70 antigen, modifying the binding properties of the CD70 antigen, interfering with signals that are required to activate or deactivate CD70, activating the CD70 antigen at the wrong time, or interfering with other molecules required for the normal synthesis or functioning of CD70.

"CD27" (NCBI-GeneID: 939) also called "TNFRSF7" (Tumor Necrosis Factor Receptor Superfamily, Member 7), T14, CD27 Antigen, CD27L Receptor, T-Cell Activation Antigen CD27, T cell Activation Antigen S152, S152. LPFS2, Tp55) is a member of the TNF Receptor superfamily that is required for the generation and long term maintenance of T cell immunity. CD27 binds to ligand CD70, and plays a key role in regulating B-cell activation and immunoglobulin synthesis. This receptor transduces signals that lead to the activation of NF-kappaB and MAPK8/JNK. Adaptor proteins TRAF2 and TRAF5 have been shown to mediate the signaling process of this receptor. CD27-binding protein (SIVA), a proapoptotic protein, can bind to this receptor and is thought to play an important role in the apoptosis induced by this receptor.

A "CD27 signaling pathway inhibitor" denotes an agent that reduces or attenuates the activity level of signaling through CD27.

A "CD27 inhibitor" in the context of the invention denotes an agent that acts directly on CD27 to reduce or attenuate the activity level of signaling through CD27. Such inhibition can result from a variety of events, such as the interrupted binding of the CD27 antigen to an appropriate receptor, inactivating the CD27 antigen, such as by cleavage or other modification, altering the affinity or CD27 to its ligand or receptor, preventing or reducing the expression of CD27 on a cell, expressing an abnormal or inactive CD27 antigen, or deactivating the antigen, preventing or reducing the proper conformational folding of the CD27 antigen, modifying the binding properties of the CD27 antigen, interfering with signals that are required to activate or deactivate CD27, activating the CD27 antigen at the wrong time, or interfering with other molecules required for the normal synthesis or functioning of CD27.

As used herein, the term "BCR-ABL1" refers to the fusion oncogene which encodes a chimeric BCR-ABL1 protein with a constitutively active BCR-ABL1 tyrosine kinase (TK) activity. In this context, protein tyrosine kinases encoded by the BCR-ABL1 gene can include, for example BCR-ABL1 p210 fusion protein (accession number: A1Z199) and BCR-ABL pi 85 fusion protein (accession number: Q13745). The term BCR-ABL1 is intended to be inclusive of alternative BCR-ABL1 gene products and also is inclusive of alternative designations such as BCR-ABL oncogene, BCR-ABL proto-oncogene, BCR-ABL1, and BCR-ABL oncoprotein used by those skilled in the art. In rare CML cases lacking the traditional t (9;22) translocation, other translocations result in the creation of the BCR-ABL1 fusion gene, which sometimes involve multiple chromosomes.

As used herein, the terms "BCR-ABL1 tyrosine kinase inhibitor," "BCR-ABL1 kinase inhibitor," "BCR-ABL1 KI" and "BCR-ABL1 TKI" refer to any compound or agent that can inhibit BCR-ABL1 TK activity in an animal, in particular a mammal, for example a human. In this context, an inhibitor is understood to decrease the activity of a BCR-ABL1 tyrosine kinase compared to the activity in the absence of the exogenously administered compound or agent. The term is intended to include indirectly or directly acting compounds or agents. As used in the art, BCR-ABL1 TKI generally refers to a class of compounds which are known to inhibit BCR-ABL1 TK, but may further inhibit alternative signaling pathways, such as for example, Src pathway. Additional information can be found, for example, in WO2013177420, the contents of which are hereby incorporated by reference in their entirety.

As used herein, the term "BCR-ABL1 related disorders" refers to disorders or diseases which are associated with or manifest from BCR-ABL1-mediated activity, and is intended to be inclusive of mutated forms of BCR-ABL1. In this context, disorders associated with BCR-ABL1 would benefit by direct or indirect BCR-ABL1 inhibition.

The term "antibody" refers to an immunoglobulin (Ig) molecule, which is generally comprised of four polypeptide chains, two heavy (H) chains and two light (L) chains, or a functional fragment, mutant, variant, or derivative thereof that retains the epitope binding features of an Ig molecule. Such fragment, mutant, variant, or derivative antibody formats are known in the art. In an embodiment of a full-length antibody, each heavy chain is comprised of a heavy chain variable region (VH) and a heavy chain constant region (CH). The heavy chain variable region (domain) is also designated as VH in this disclosure. The CH is comprised of three domains, CH1, CH2 and CH3. Each light chain is comprised of a light chain variable region (VL) and a light chain constant region (CL). The CL is comprised of a single CL domain. The light chain variable region (domain) is also designated as VL in this disclosure. The VH and VL can be further subdivided into regions of hypervariability, termed complementarity determining regions (CDRs), interspersed with regions that are more conserved, termed framework regions (FRs). Generally, each VH and VL is composed of three CDRs and four FRs, arranged from amino-terminus to carboxy-terminus in the following order: FR1, CDR1, FR2, CDR2, FR3, CDR3, and FR4. Immunoglobulin molecules can be of any type (e.g., IgG, IgE, IgM, IgD, IgA and IgY), class (e.g., IgG1, IgG2, IgG3, IgG4, IgA1 and IgA2), or subclass.

The term "humanized antibody" refers to an antibody from a non-human species that has been altered to be more "human-like", i.e., more similar to human germline sequences. One type of humanized antibody is a CDR-grafted antibody, in which non-human CDR sequences are introduced into human VH and VL sequences to replace the corresponding human CDR sequences. A "humanized antibody" is also an antibody or a variant, derivative, analog or fragment thereof that comprises framework region (FR) sequences having substantially (e.g., at least 80%, at least 85%, at least 90%, at least 95%, at least 98% or at least 99% identity to) the amino acid sequence of a human antibody and at least one CDR having substantially the amino acid sequence of a non-human antibody. A humanized antibody may comprise substantially all of at least one, and typically two, variable domains (Fab, Fab', F(ab') 2, FabC, Fv) in which the sequence of all or substantially all of the CDR regions correspond to those of a non-human immunoglobulin (i.e., donor antibody) and the sequence of all or substantially all of the FR regions are those of a human immunoglobulin. The humanized antibody also may include the CH1, hinge, CH2, CH3, and CH4 regions of the heavy chain. In an embodiment, a humanized antibody also comprises at least a portion of a human immunoglobulin Fc region. In some embodiments, a humanized antibody only contains a humanized light chain. In some embodiments, a humanized antibody only contains a humanized heavy chain. In some embodiments, a humanized antibody only contains a humanized variable domain of a light chain and/or humanized variable domain of a heavy chain. In some embodiments, a humanized antibody contains a light chain as well as at least the variable domain of a heavy chain. In some embodiments, a humanized antibody contains a heavy chain as well as at least the variable domain of a light chain.

The term "subject" is intended to include animals. Examples of subjects include mammals, e.g., humans, dogs, cows, horses, pigs, sheep, goats, cats, mice, rabbits, rats, and transgenic non-human animals. In certain embodiments, the subject is a human, e.g., a human suffering from, at risk of suffering from, or potentially capable of suffering from cancers.

The term "effective amount" or "therapeutically effective amount" of a combination of therapeutic agents is an amount sufficient to provide an observable improvement over the baseline clinically observable signs and symptoms of the disorders treated with the combination.

The term "pharmaceutical combination" as used herein refers to either a fixed combination in one dosage unit form, or non-fixed combination or a kit of parts for the combined administration where two or more therapeutic agents can be administered independently at the same time or separately within time intervals, especially where these time intervals allow that the combination partners show a cooperative, e.g. synergistic effect.

The term "combination therapy" refers to the administration of two or more therapeutic agents to treat a therapeutic condition or disorder described in the present disclosure. Such administration encompasses co-administration of these therapeutic agents in a substantially simultaneous manner, such as in a single capsule having a fixed ratio of active ingredients or in multiple, separate containers (e.g., capsules and/or intravenous formulations) for each active ingredient. In addition, such administration also encompasses use of each type of therapeutic agent in a sequential manner, either at approximately the same time or at different times. In either case, the treatment regimen will provide beneficial effects of the drug combination in treating the conditions or disorders described herein.

The term "pharmaceutically acceptable" as used herein refers to those compounds, antibodies, materials, compositions and/or dosage forms, which are, within the scope of sound medical judgment, suitable for contact with the tissues a warm-blooded animal, e.g., a mammal or human, without excessive toxicity, irritation allergic response and other problem complications commensurate with a reasonable benefit/risk ratio.

The terms "fixed combination", "fixed dose" and "single formulation" as used herein refers to a single carrier or vehicle or dosage form formulated to deliver an amount, which is jointly therapeutically effective for the treatment of cancer, of both therapeutic agents to a patient. The single vehicle is designed to deliver an amount of each of the agents, along with any pharmaceutically acceptable carriers or excipients. In some embodiments, the vehicle is a tablet, capsule, pill, or a patch. In other embodiments, the vehicle is a solution or a suspension.

The term "non-fixed combination" or "kit of parts" means that the active ingredients, e.g. a BCR-ABL1 tyrosine kinase inhibitor (TKI), e.g., imatinib and a WNT/β-catenin signaling pathway inhibitor, are both administered to a patient as separate entities either simultaneously, concurrently or sequentially with no specific time limits, wherein such administration provides therapeutically effective levels of the two compounds in the body of the warm-blooded animal in need thereof. The latter also applies to cocktail therapy, e.g., the administration of three or more active ingredients.

The term "unit dose" is used herein to mean simultaneous administration of both agents together, in one dosage form, to the patient being treated. In some embodiments, the unit dose is a single formulation. In certain embodiments, the unit dose includes one or more vehicles such that each vehicle includes an effective amount of at least one of the agents along with pharmaceutically acceptable carriers and excipients. In some embodiments, the unit dose is one or more tablets, capsules, pills, or patches administered to the patient at the same time.

As used herein, the terms "administering" and "administration" refer to any method of providing a pharmaceutical preparation to a subject. Such methods are well known to those skilled in the art and include, but are not limited to, oral administration, transdermal administration, administration by inhalation, nasal administration, topical administration, intravaginal administration, ophthalmic administration, intraaural administration, intracerebral administration, rectal administration, sublingual administration, buccal administration, and parenteral administration, including injectable such as intravenous administration, intra-arterial administration, intramuscular administration, and subcutaneous administration. Administration can be continuous or intermittent. In various aspects, a preparation can be administered therapeutically; that is, administered to treat an existing disease or condition. In further various aspects, a preparation can be administered prophylactically; that is, administered for prevention of a disease or condition.

The term "treat" is used herein to mean to relieve, reduce or alleviate, at least one symptom of a disease in a subject. Within the meaning of the present invention, the term "treat" also denotes, to arrest, delay the onset (i.e., the period prior to clinical manifestation of a disease or symptom of a disease) and/or reduce the risk of developing or worsening a symptom of a disease.

2) WNT Signaling Inhibitors

The methods disclosed herein generally comprise administering to the subject an effective amount of a therapeutic combination of a WNT signaling pathway inhibitor and a BCR-ABL1 tyrosine kinase inhibitor. The WNT signaling pathway and suitable, non-limiting WNT signaling pathway inhibitors for use in the disclosed methods are described in detail below.

a) The WNT Signaling Pathway

A schematic of the canonical and non-canonical WNT signaling pathways can be found in FIG. 12 (reproduced from Katoh et al. Clin Cancer Res (2007) 13 (14) 4042-4045, which is incorporated by reference it its entirety). WNT signals are transduced to the canonical pathway for cell fate determination, and to the noncanonical pathway for control of cell movement and tissue polarity (recently reviewed by Clevers and Nusse Cell (2012) 149, 1192-1205). Canonical WNT signals are transduced through Frizzled family receptors and LRP5/LRP6 co-receptor to the β-catenin signaling cascade. Noncanonical WNT signals are transduced through Frizzled family receptors and ROR2/RYK co-receptors to the DVL-dependent (Rho family GTPases and INK) or the $Ca^{2+}$-dependent (NLK and NFAT) signaling cascades. Microtubule affinity-regulating kinase (MARK; PAR-1) family kinases, CKIF, and FRAT are positive regulators of the canonical WNT pathway, whereas APC, AXIN1, AXIN2, CKIα, NKD1, NKD2, βTRCP1, βTRCP2, ANKRD6, NLK, and PPARγ are negative regulators. FGF20, DKK1, WISP1, MYC, CCND1, and Glucagon (GCG) are target genes of the canonical WNT signaling pathway. WNT signals are context-dependently transduced to both pathways based on the expression profile of WNT, SFRP, WIF, DKK, Frizzled receptors, co-receptors, and the activity of intracellular WNT signaling regulators.

Examples of proteins implicated in the secretion of functional WNTs include, but are not limited to, porcupine (Porcn), wntless/evenness interrupted/sprinter (wls/evi), and Vps35p.

Wls/evi is a 7 pass transmembrane protein which resides in the Golgi apparatus and is required for secretion of Wg (*drosophila*) MOM-2 (*C. elegans*) and WNT3A. It contains a conserved structural motif (PFAM: DUF1171) whose structure and function are both unknown.

Vps35p is a subunit of a multiprotein complex called the retromer complex which is involved in intracellular protein trafficking. In yeast, Vpsl Op, Vps29p, and Vps35p function together to direct "cargo selection" for endocytic vesicles that recycle proteins from endosomes to the late Golgi or trans-Golgi network. Vps35p functions in binding target proteins for recruitment into vesicles.

Fatty acid modification of WNTs is critical for their function. WNTs are palmitoylated on one or two highly conserved sites. The enzyme responsible for this modification, Porcupine (Porcn) is a member of the membrane-bound O-acyltransferase (MBOAT) family of palmitoyl transferases. The sequence conservation at both known WNT modification sites suggests that Porcn may act on and be required for secretion and activity of all members of the WNT family. Inhibitors of porcupine, e.g. LGK974, may therefore block all functional WNT signaling b) Inhibitors of CD27 Signaling

In certain embodiments, the WNT signaling pathway inhibitor is an inhibitor of the CD27 signaling pathway.

In certain embodiments, the inhibitor of CD27 signaling is a CD70 inhibitor. CD70 inhibitors include, without limitation, inhibitory proteins (e.g., antibodies), inhibitory carbohydrates, inhibitory glycoproteins, chemical entities, inhibitory nucleic acids (e.g., antisense, siRNA, and miRNA), and small molecules. In certain embodiments, CD70 inhibitors are antibodies.

Characteristic anti-CD70 antibodies are disclosed, for instance, in K. Tesselaar et al., The Journal of Immunology, 170: pages 33-40 (2003) and Israel et al., Mol Cancer Ther (2005) 4; 2037, the pertinent disclosures of which are incorporated herein in its entirety. Exemplary methods of targeting CD70 can be found in Boursalian et al., Advances in Experimental Medicine and Biology Volume 647, 2009, pp 108-119.

In certain embodiments, the CD70 antibody is an antibody set forth in U.S. Pat. Nos. 8,663,642 and 8,535,678 and the published U.S. Patent Application No. 2010/0150950, the pertinent disclosures of which are incorporated by reference herein in its entirety.

In certain embodiments, the CD70 antibody is vorsetuzumab (also known as: D10342, CAS: 1165740-62-4, PubChem: 172232436; described in McEarchern et al. Clin Cancer Res. (2008) 1; 14(23):7763-72), which blocks binding of CD70 to CD27.

In certain embodiments, the CD70 antibody is MDX-1411 (Bristol Myers Squibb and Medarex) is a glycoengineered, fully humanized IgG1 monoclonal antibody directed against the extracellular domain of the human CD70 molecule (described in U.S. Pat. No. 8,124,738, which is incorporated herein by reference in its entirety.

In certain embodiments, the CD70 antibody is AMG 172 (Amgen; NCT01497821), an antibody drug conjugate (ADC) that binds to CD70. AMG 172 is currently in Phase I clinical trials for the treatment of Clear Cell Renal Cell Carcinoma (ccRCC).

In certain embodiments, the CD70 antibody is an antibody set forth in U.S. Patent Publication No. US2013/0078237 and U.S. Pat. No. 7,261,892, which are incorporated herein by reference in its entirety.

In certain embodiments, the CD70 antibody is an antibody set forth in U.S. Patent Publication No. US20140147450, which are incorporated herein by reference in its entirety.

In certain embodiments, the anti-CD70 antibody comprises one or more of the VH, VL or CDR amino acid sequences set forth in Table 1 herein.

TABLE 1

| VH, VL or CDR amino acid sequences of an exemplary CD70 antibody | | |
|---|---|---|
| Name | Sequence | SEQ ID NO: |
| CDRl | VYYMN | 1 |
| HCDR2 | DINNEGGTTYYADSVKG | 2 |
| HCDR3 | DAGYSNHVPIFDS | 3 |

TABLE 1-continued

VH, VL or CDR amino acid sequences of an exemplary CD70 antibody

| Name | Sequence | SEQ ID NO: |
|---|---|---|
| LCDR1 | GLKSGSVTSDNFPT | 4 |
| LCDR2 | NTNTRHS | 5 |
| LCDR3 | ALFISNPSVE | 6 |
| VH | EVQLVESGGGLVQPGGSLRLSCAASGFTFSVYYMNWVRQAPGKGLE WVSDINNEGGTTYYADSVKGRFTISRDNSKNSLYLQMNSLRAEDTAV YYCARDAGYSNHVPIFDSWGQGTLVTVSS | 7 |
| VL | QAVVTQEPSLTVSPGGTVTLTCGLKSGSVTSDNFPTWYQQTPGQAPRL LIYNTNTRHSGVPDRFSGSILGNKAALTITGAQADDEAEYFCALFISNPS VEFGGGTQLTVLG | 8 |

In certain embodiments, the CD70 antibody comprises a heavy chain variable domain comprising at least one of CDRH1, CDRH2, and CDRH3 regions having the amino acid sequences set forth in SEQ ID NOs: 1, 2, and 3, respectively.

In certain embodiments, the CD70 antibody comprises a light chain variable domain comprising at least one of CDRL1, CDRL2, and CDRL3 regions, having the amino acid sequences set forth in SEQ ID NOs: 4, 5, and 6, respectively.

In certain embodiments, the CD70 antibody comprises a heavy chain variable domain comprising CDRH1, CDRH2, and CDRH3 regions, and a light chain variable domain comprising CDRL1, CDRL2, and CDRL3 regions, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively.

In certain embodiments, the CD70 antibody comprises a heavy chain variable domain comprising an amino acid sequence having at least 90% sequence identity (e.g., 90, 91, 92, 93, 94, 95, 96, 97, 98, or 99% identity) to the amino acid sequence set forth in SEQ ID NO: 7.

In certain embodiments, the CD70 antibody comprises a light chain variable domain comprising an amino acid sequence having at least 90% sequence identity (e.g., 90, 91, 92, 93, 94, 95, 96, 97, 98, or 99% identity) to the amino acid sequence set forth in SEQ ID NO: 8.

In certain embodiments, the CD70 antibody comprises a heavy chain variable domain comprising the amino acid sequence set forth in SEQ ID NO: 7.

In certain embodiments, the CD70 antibody comprises a light chain variable domain comprising the amino acid sequence set forth in SEQ ID NO: 8.

In certain embodiments, the CD70 antibody comprises a heavy chain variable domain and the light chain variable domain comprising the amino acid sequences set forth in SEQ ID NOs: 7 and 8, respectively.

In certain embodiments, the CD27 signaling pathway inhibitor is a CD27 inhibitor. CD27 inhibitors include, without limitation, inhibitory proteins (e.g., antibodies), inhibitory carbohydrates, inhibitory glycoproteins, chemical entities inhibitory nucleic acids (e.g., antisense, siRNA, and miRNA), and small molecules.

In certain embodiments, the CD27 inhibitor is an anti-CD27 antibody. Antibodies against CD27 are available, for example, from eBioscience (Cat. #14-0271-82). Humanized antibodies that specifically bind to an extracellular region of a polypeptide encoded by the CD27 gene can be found, for example, in published U.S. Patent Application Nos. 2013/0243795 and 2012/0093805 the pertinent disclosures of which are incorporated by reference herein in its entirety.

c) Small Molecule WNT Signaling Pathway Inhibitors

In certain embodiments, the WNT signaling inhibitor is a small molecule inhibitor that interferes with activity of one or more components of the WNT signaling pathway. Non limiting examples of small molecules inhibitors of the WNT signaling pathway that may be used in the methods and compositions disclosed herein are shown in Table 2, and are set forth in the sections below (see Voronnkov and Krauss, Current Pharmaceutical Design (2013) 19, 634-664, which is incorporated by reference herein in its entirety). A diagram depicting the mode of action of some of these inhibitors can be found in FIG. 13 herein.

(i) XAV939 (Novartis; Pre-Clinical)

A key feature of the WNT pathway is the regulated proteolysis (degradation) of β-catenin by the β-catenin destruction complex. Proteins like WTX, APC or Axin are involved in the degradation process. A proper degradation of β-catenin is important to avoid an inappropriate activation of the WNT pathway which has been observed in many cancers. Tankyrases I and II inhibit activity of Axin and hence inhibit the degradation of β-catenin. Consequently, tankyrase inhibitors increase degradation of β-catenin.

XAV9393 blocks WNT-stimulated accumulation of β-catenin by increasing the levels of the AXIN1 and AXIN2 proteins. XAV939 also regulates AXIN levels via inhibition of tankyrases 1 and 2 (TNKS1 and TNKS2), both of which are members of the poly(ADP-ribose) polymerase (PARP) protein family (S. J. Hsiao et al., Biochimie 90, 2008, 83-92). XAV939 inhibits growth of DLD-1-cancer cells derived from a colorectal adenocarcinoma.

XAV939 is further described in the published U.S. Patent Application US20100267626, which is incorporated herein in its entirety.

(ii) LGK974 (Novartis; NCT01351103)

This small molecule inhibits the acyltransferase porcupine. Preclinical work demonstrates this enzyme's action is crucial in the secretion of WNT ligands out of the cell; therefore, inhibiting porcupine can be a small-molecule-based method for inhibiting WNT ligand-mediated activation.

LGK974 is currently in Phase I clinical trials for the treatment of gastric cancer, breast cancer, pancreatic neuroendocrine tumors and melanoma.

(iii) PRI-724 (Prism Pharma Co, Ltd/Eisai)

PRI-724 is a small-molecule inhibitor of the interaction between β-catenin and Creb-binding protein (CBP). Disrupting the interaction prevents activated transcription by aberrant WNT signaling at many levels. It is being studied in both solid tumors and myeloid malignancies.

(iv) JW55 (Tocris Bioscience; Pre-Clinical; CAS #: 664993-53-7)

JW55 (or N-(4-(((4-(4-methoxyphenyl)tetrahydro-2H-pyran-4-yl)methyl)carbamoyl)phenyl)furan-2-carboxamide) is a tankyrase 1 and tankyrase 2 (TNKS1/2) inhibitor. JW55 functions via inhibition of the PARP domain of tankyrase 1 and tankyrase 2 (TNKS1/2), regulators of the β-catenin destruction complex. Inhibition of TNKS1/2 poly (ADP-ribosyl)ation activity by JW55 led to stabilization of AXIN2, a member of the β-catenin destruction complex, followed by increased degradation of β-catenin. In a dose-dependent manner, JW55 inhibited canonical WNT signaling in colon carcinoma cells that contained mutations in either the APC (adenomatous polyposis coli) locus or in an allele of β-catenin. In addition, JW55 reduced XWNT8-induced axis duplication in *Xenopus* embryos and tamoxifen-induced polyposis formation in conditional APC mutant mice. (Waaler et al. Cancer Res. 2012; 72(11):2822-32).

(v) CWP232291 (CWP291; JW Theriac Pharmaceutical; NCT01398462)

CWP232291 was identified in a high throughput screen for inhibitors of WNT mediated transcriptional activity. In vitro, CWP232291 demonstrated anti-proliferative effects in various cell lines, and inhibited transcription of β-catenin target genes. In an in vivo AML model, CWP232291 inhibited tumor progression and exhibited a favorable safety profile, and is currently scheduled for Phase I clinical trials in AML and multiple myeloma. While its mechanism of action remains to be elucidated, this compound was reported to be active in the context of both wild-type and mutant β-catenin, raising the possibility of anti-tumor effects across a broad range of cancers.

TABLE 2

Small molecules inhibitors of the WNT signaling

| Structure | Compound | Target |
|---|---|---|
| 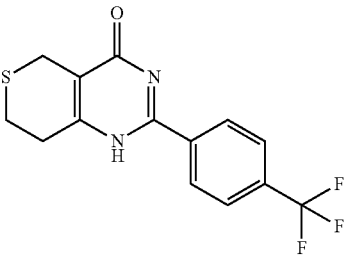 [SMILES: O=c1nc(-c2ccc(C(F)(F)F)cc2)[nH]c2c1CSCC2] | XAV939 | Tankyrases 1, 2 |
| 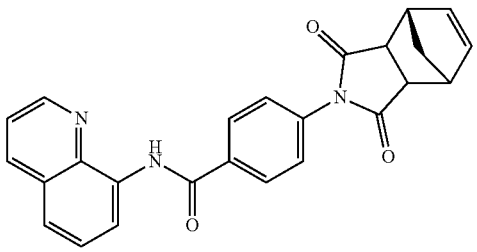 [SMILES: O=C(Nc1cccc2cccnc12)c1ccc(N2C(=O)C3C4C=C[C@H](C4)C3C2=O)cc1] | IWR1 | Tankyrases 1, 2 |
| 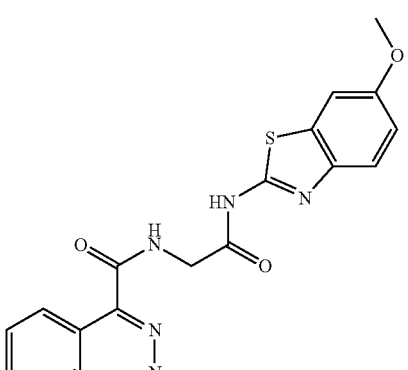 | IWP-1 | Porcupine |

TABLE 2-continued
Small molecules inhibitors of the WNT signaling
| Structure | Compound | Target |
|---|---|---|
| 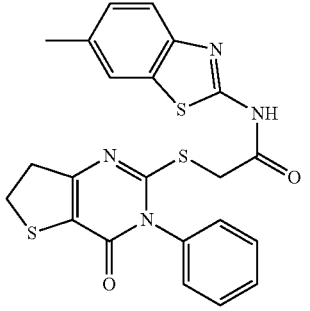 [SMILES: Cc1ccc2nc(NC(=O)CSc3nc4c(c(=O)n3-c3ccccc3)SCC4)sc2c1] | IWP-2 | Porcupine |
| 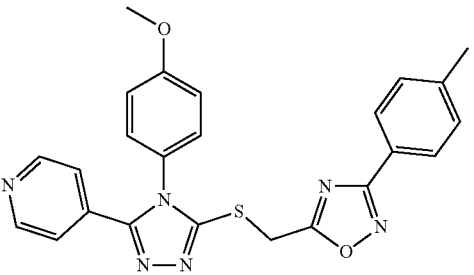 [SMILES: COc1ccc(-n2c(SCc3nc(-c4ccc(C)cc4)no3)nnc2-c2ccncc2)cc1] | JW74 | Tankyrases 1, 2 |
| 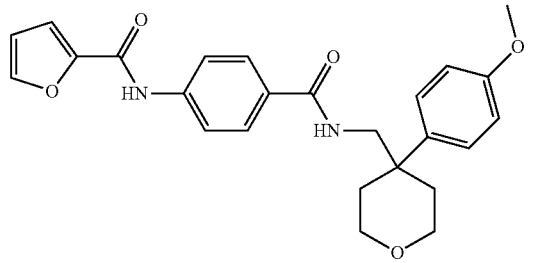 [SMILES: COc1ccc(C2(CNC(=O)c3ccc(NC(=O)c4ccco4)cc3)CCOCC2)cc1] | JW55 | Tankyrases 1, 2 |
| 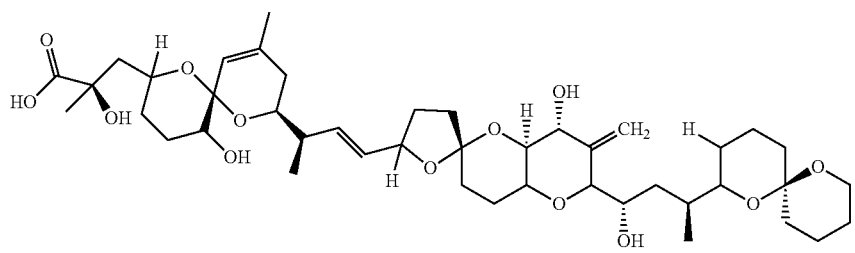 | Okadaic acid | PP2A phosphatase |
| 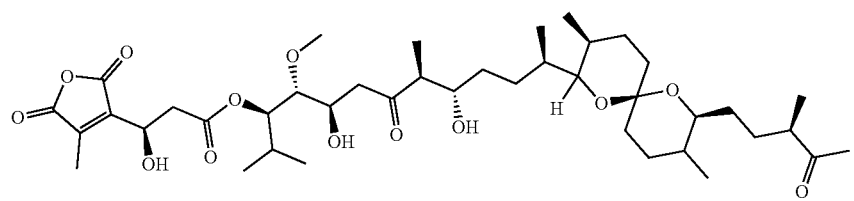 | Tautomycin | PP1 phosphatase |

TABLE 2-continued

Small molecules inhibitors of the WNT signaling

| Structure | Compound | Target |
|---|---|---|
| 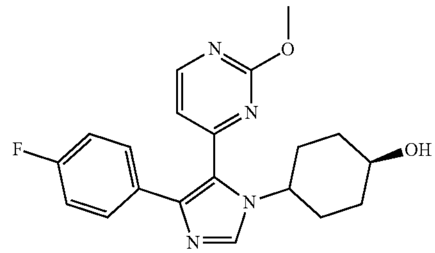 | SB239063 | P38 MAPK |
| 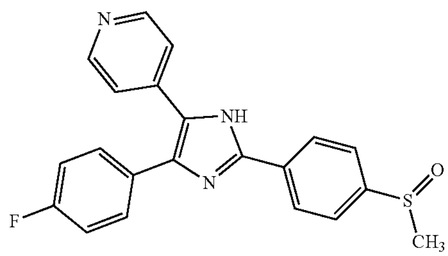 [SMILES: CS(=O)c1ccc(-c2nc(-c3ccc(F)cc3)c(-c3ccncc3)[nH]2)cc1] | SB203580 | P38 MAPK |
| 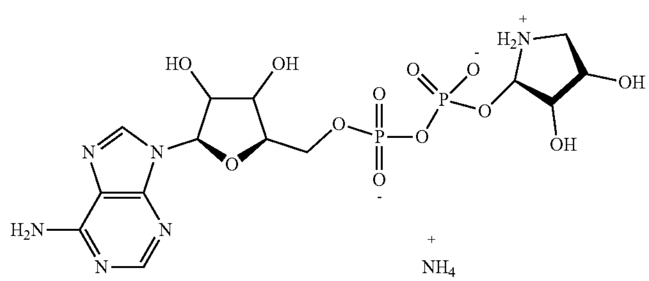 | ADP-HPD | PARG |
| 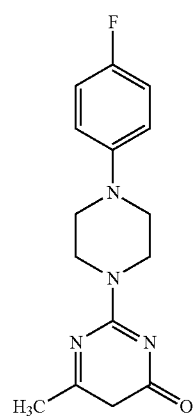 [SMILES: CC1=NC(N2CCN(c3ccc(F)cc3)CC2)=NC(=O)C1] | 2-[4-(4-fluoro-phenyl)piperazin-1-yl-[-6-methylpyrimidin-4(3H)-one | Tankyrases 1, 2 |
| 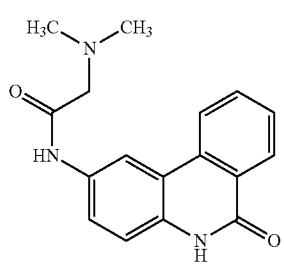 [SMILES: CN(C)CC(=O)Nc1ccc2[nH]c(=O)c3ccccc3c2c1] | PJ34 | Tankyrases 1, 2 |

TABLE 2-continued

Small molecules inhibitors of the WNT signaling

| Structure | Compound | Target |
|---|---|---|
| 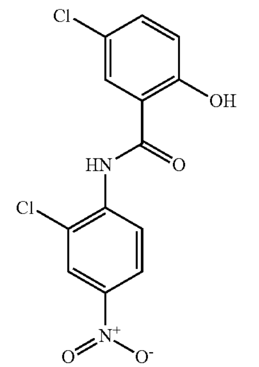 [SMILES: O=C(Nc1ccc([N+](=O)[O-])cc1Cl)c1cc(Cl)ccc1O] | Niclosamide | Downregulates Dvl-2, triggers LRP6 degradation |
| 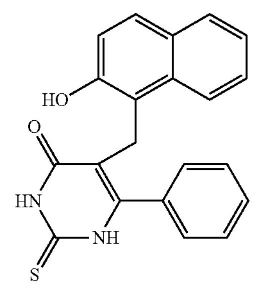 [SMILES: O=c1[nH]c(=S)[nH]c(-c2ccccc2)c1Cc1c(O)ccc2ccccc12] | Cambinol | SIRT1 |
| 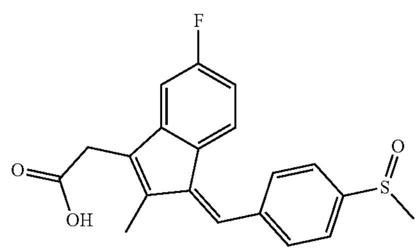 [SMILES: CC1=C(CC(=O)O)c2cc(F)ccc2/C1=C\c1ccc(S(C)=O)cc1] | Sulindac | PDZ domain of Dishevelled |
| 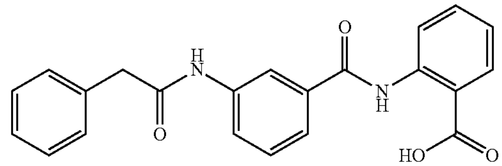 [SMILES: O=C(Cc1ccccc1)Nc1cccc(C(=O)Nc2ccccc2C(=O)O)c1] | 3289-8625 | Dishevelled |
| 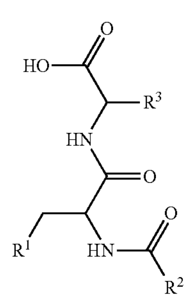 | Scaffold A for series of analogs | Dishevelled |

TABLE 2-continued

Small molecules inhibitors of the WNT signaling

| Structure | Compound | Target |
|---|---|---|
| 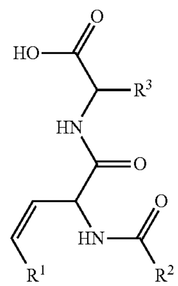 | Scaffold B for series of analogs | Dishevelled |
| 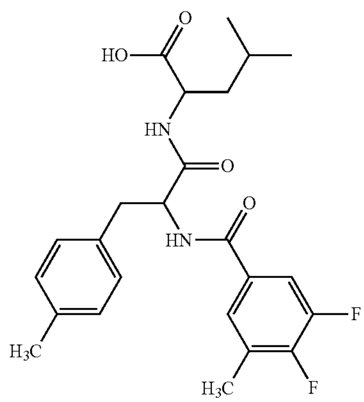 [SMILES: Cc1ccc(CC(NC(=O)c2cc(C)c(F)c(F)c2)C(=O)NC(CC(C)C)C(=O)O)cc1] | J01-017a | Dishevelled |
| 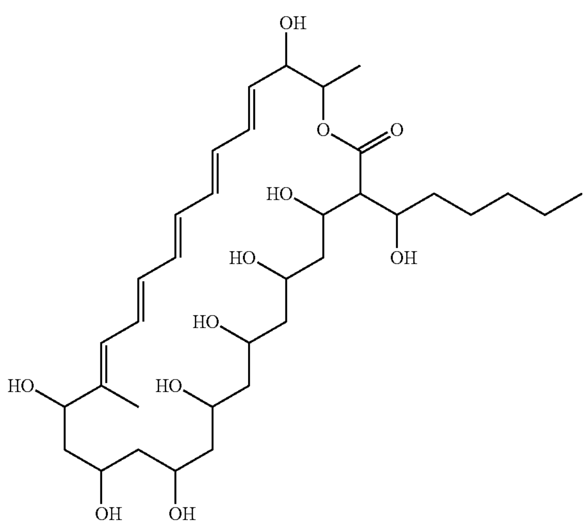 [SMILES: CCCCCC(O)C1C(=O)OC(C)C(O)/C=C/C=C/C=C/C=C/C=C(\C)C(O)CC(O)CC(O)CC(O)CC(O)CC(O)CC1O] | NSC668036 | Dishevelled |
| 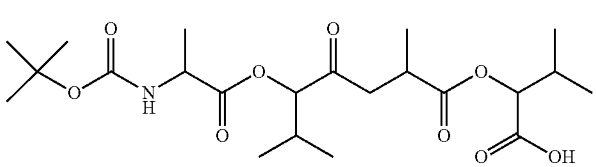 [SMILES: CC(CC(=O)C(OC(=O)C(C)NC(=O)OC(C)(C)C)C(C)C)C(=O)OC(C(=O)O)C(C)C] | Filipin | Caveolin-mediated endocytosis |

TABLE 2-continued

Small molecules inhibitors of the WNT signaling

| Structure | Compound | Target |
|---|---|---|
| 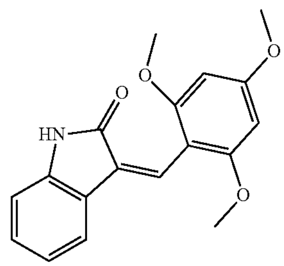 [SMILES: COc1cc(OC)c(/C=C2\C(=O)Nc3ccccc32)c(OC)c1] | IC261 | CK1δ/ε |
| 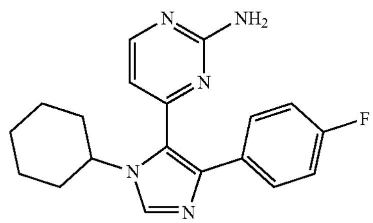 [SMILES: Nc1nccc(-c2c(-c3ccc(F)cc3)ncn2C2CCCCC2)n1] | PF670462 | CK1ε and CK1δ |
| 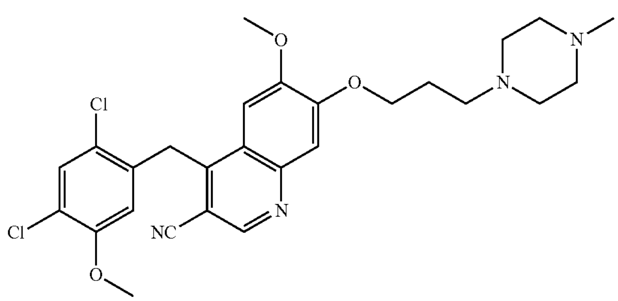 [SMILES: COc1cc(Cc2c(C#N)cnc3cc(OCCCN4CCN(C)CC4)c(OC)cc23)c(Cl)cc1Cl] | Bosutinib | Src kinase |
| 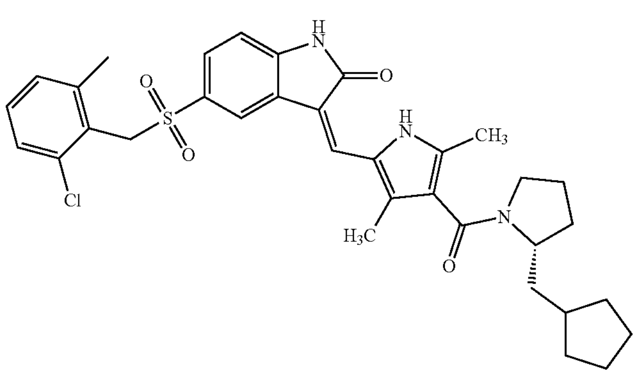 [SMILES: Cc1cccc(Cl)c1CS(=O)(=O)c1ccc2c(c1)/C(=C/c1[nH]c(C)c(C(=O)N3CCC[C@@H]3CC3CCCC3)c1C)C(=O)N2] | PHA665752 | c-Met |

TABLE 2-continued
Small molecules inhibitors of the WNT signaling
| Structure | Compound | Target |
|---|---|---|
| 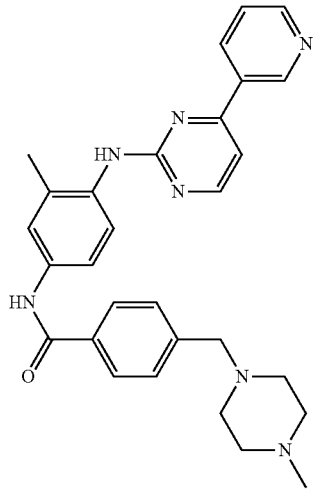 [SMILES: Cc1cc(NC(=O)c2ccc(CN3CCN(C)CC3)cc2)ccc1Nc1nccc(-c2cccnc2)n1] | Imatinib | Different tyrosine kinases |
| 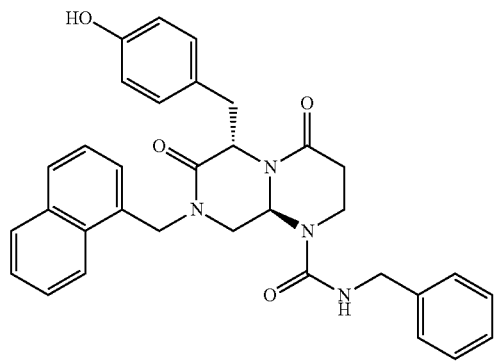 [SMILES: O=C1[C@H](Cc2ccc(O)cc2)N2C(=O)CCN(C(=O)NCc3ccccc3)[C@H]2CN1Cc1cccc2ccccc12] | ICG-001 | CREB binding protein (CBP) |
| 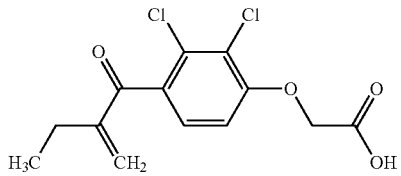 [SMILES: C=C(CC)C(=O)c1ccc(OCC(=O)O)c(Cl)c1Cl] | Ethacrynic acid | Lef-1 |
| 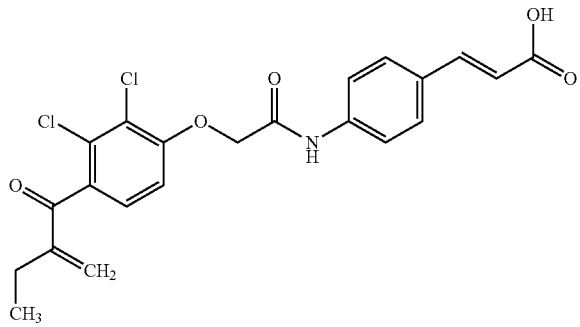 [SMILES: C=C(CC)C(=O)c1ccc(OCC(=O)Nc2ccc(/C=C/C(=O)O)cc2)c(Cl)c1Cl] | Ethacrynic acid derivative | Lef-1 |

TABLE 2-continued
Small molecules inhibitors of the WNT signaling
| Structure | Compound | Target |
| --- | --- | --- |
| 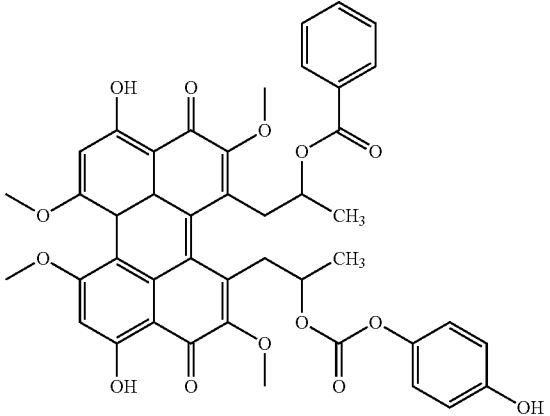 [SMILES: COC1=CC(O)=C2C(=O)C(OC)=C(CC(C)OC(=O)c3ccccc3)C3=C4C(CC(C)OC(=O)Oc5ccc(O)cc5)=C(OC)C(=O)c5c(O)cc(OC)c(c54)C1C23] | PKF115-584 | β-catenin |
| 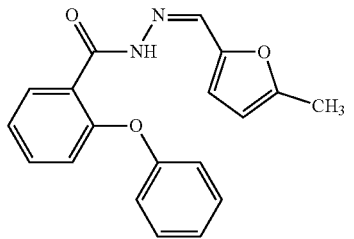 [SMILES: Cc1ccc(/C=N\NC(=O)c2ccccc2Oc2ccccc2)o1] | PNU-74654 | β-catenin |
| 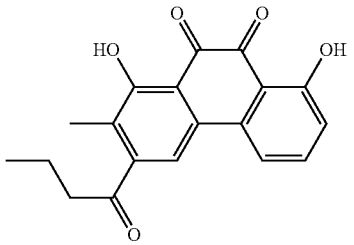 [SMILES: CCCC(=O)c1cc2c(c(O)c1C)C(=O)C(=O)c1c(O)cccc1-2] | PKF118-744 | β-catenin |
| 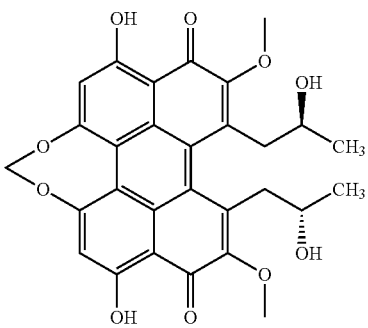 [SMILES: COc1c(C[C@H](C)O)c2c3c(C[C@H](C)O)c(OC)c(=O)c4c(O)cc5c(c6c(cc(O)c(c1=O)c62)OCO5)c43] | CGP049090 | β-catenin |
| 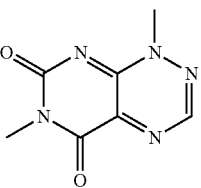 | PKF118-310 | β-catenin |

TABLE 2-continued

Small molecules inhibitors of the WNT signaling

| Structure | Compound | Target |
|---|---|---|
| 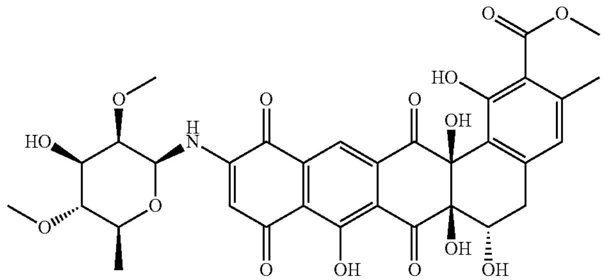 | ZTM000990 | β-catenin |
| 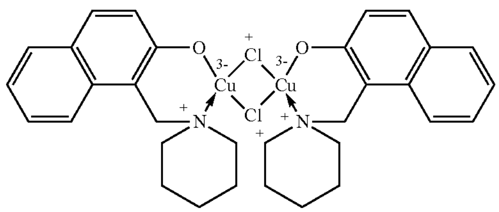 | BC21 | β-catenin |
| 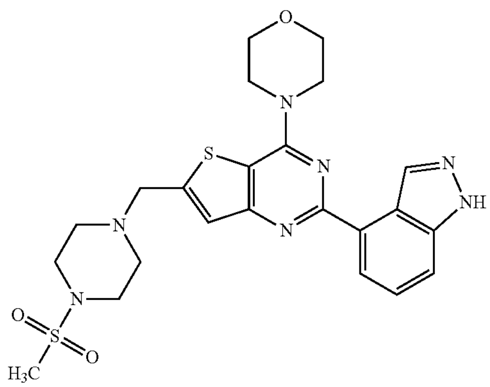 [SMILES: CS(=O)(=O)N1CCN(Cc2cc3nc(-c4cccc5[nH]ncc45)nc(N4CCOCC4)c3s2)CC1] | GDC-0941 | PI3K |
| | Rp-8-Br-cAMP | PKA | d) Antibodies Directly Targeting the WNT Signaling Pathway Components

In certain embodiments, the WNT signaling inhibitor is an antibody that directly targets one or more components of the WNT signaling pathway. Exemplary antibodies are set forth in the sections below.

(i) OMP-18R5 (Vantictumab; OncoMed Pharmaceuticals/Bayer)

This monoclonal antibody targets the Frizzled receptors to block association with WNT ligands. It was recently shown to potently block the capabilities of pancreatic tumor-initiating cells in a serial dilution assay. In xenograft models of breast, lung, pancreatic, and colon cancer, OMP-18R5 demonstrated significant inhibition of tumor growth, and it synergized with standard-of-care treatment in these models. OMP-18R5 (in combination with standard chemotherapy drugs) is currently being evaluated in Phase I clinical trials for the treatment of NSCLC, metastatic breast cancer, and stage IV pancreatic cancer (NCT01957007, NCT01973309, NCT02005315 respectively). Other frizzled receptor binding proteins are described in U.S. Pat. Nos. 8,507,442 and 7,982,013.

(ii) OMP-54F28 (Ipafricept; OncoMed Pharmaceuticals/Bayer)

This agent is a fusion protein of the Frizzled8 ligand-binding domain with the Fc region of a human immunoglobulin. It binds and sequesters soluble WNT ligand, impairing its recognition by receptors on tissues. FZD-Fc soluble receptors are described in detail in U.S. Pat. Nos. 7,723,477, 8,324,361 and 8,765,913, the contents of which are incorporated herein in their entirety.

e) Other Examples of WNT Signaling Pathway Inhibitors

Additional examples of inhibitors of the WNT signaling pathway that can be used in the methods and compositions disclosed herein include, without limitation, tankyrase inhibitors disclosed in WO2014045101, Indazole WNT inhibitors disclosed in U.S. Pat. No. 8,604,052. WNT pathway inhibitors are also disclosed in WO 2013093508, WO2013185353, PCT/US2009/052481.

In certain embodiments, the WNT signaling pathway inhibitor is a WNT inhibitor protein, for example, as disclosed in U.S. Pat. No. 6,844,422.

In certain embodiments, the WNT signaling pathway inhibitor is a WNT pathway siRNA, for example, as disclosed in U.S. Pat. No. 7,745,419.

3) BCR-ABL1 TKI Inhibitors

The methods disclosed herein generally comprise administering to the subject an effective amount of a therapeutic combination of a WNT signaling pathway inhibitor and a BCR-ABL1 tyrosine kinase inhibitor. Suitable, non-limiting BCR-ABL1 tyrosine kinase inhibitors for use in the disclosed methods are described in detail below.

In certain embodiments, the BCR-ABL1 tyrosine kinase inhibitor is imatinib, and pharmaceutically acceptable salts thereof (marketed by Novartis as GLEEVEC®; CAS Number: 82115-62-6), and pharmaceutically acceptable salts thereof, having a structure represented by the formula:

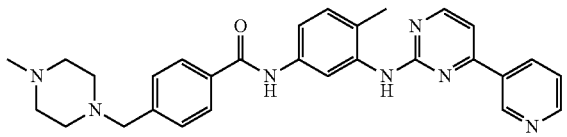 [SMILES: Cc1ccc(NC(=O)c2ccc(CN3CCN(C)CC3)cc2)cc1Nc1nccc(-c2cccnc2)n1]

This compound has been described as inhibiting the activity of BCR-ABL1, KIT, and the platelet-derived growth factor receptor (PDGFR).

In certain embodiments, the BCR-ABL1 tyrosine kinase inhibitor is dasatinib (marketed by Bristol-Myers Squibb as SPRYCELL®; CAS Number: 302962-49-8), and pharmaceutically acceptable salts thereof, having a structure represented by the formula:

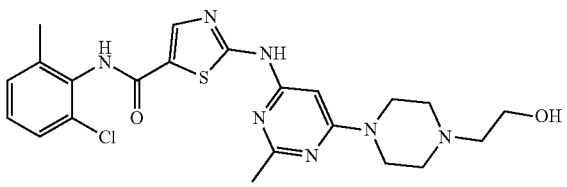 [SMILES: Cc1nc(Nc2ncc(C(=O)Nc3c(C)cccc3Cl)s2)cc(N2CCN(CCO)CC2)n1]

This compound has been described as inhibiting the activity of SRC and SRC-family kinases, BCR-ABL1, KIT, PDGFR and ephrin receptor tyrosine kinases.

In certain embodiments, the BCR-ABL1 tyrosine kinase inhibitor is nilotinib (marketed by Novartis as TASIGNA®; CAS Number: 0641571-10-0), and pharmaceutically acceptable salts thereof, having a structure represented by the formula:

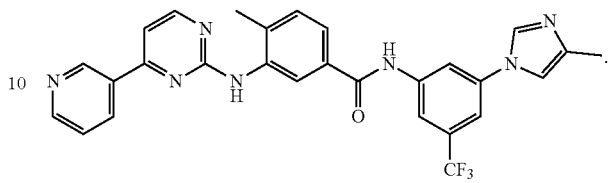

This compound has been described as inhibiting the activity BCR-ABL1, KIT, and PDGFR. It is also suspected of inhibiting ABL-related kinase ARG and the ephrin receptor EPHB4.

In certain embodiments, the BCR-ABL1 tyrosine kinase inhibitor is bosutinib (marketed by Pfizer as BOSULIF®; CAS Number: 380843-75-4), and pharmaceutically acceptable salts thereof, having a structure represented by the formula:

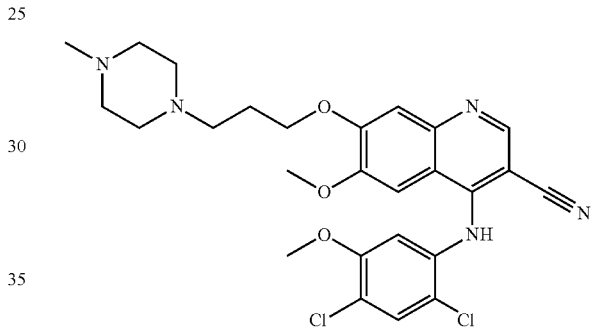

This compound has been described as inhibiting the activity of BCR-ABL1, SRC-family kinases, and STAT5.

In certain embodiments, the BCR-ABL1 tyrosine kinase inhibitor is ponatinib (marketed by Ariad as ICLUSIG®; CAS Number: 943319-70-8), and pharmaceutically acceptable salts thereof, having a structure represented by the formula:

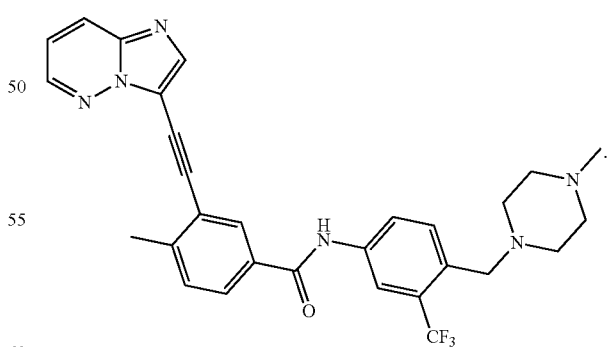

This compound has been described as inhibiting the activity of BCR-ABL1, FLT3, vascular endothelial growth factors (VEGFRs), fibroblast growth factors (FGFRs), and angiopoietin (Tie2).

In certain embodiments, the BCR-ABL1 tyrosine kinase inhibitor is bafetinib (developed by CytRx and also known as INNO-406; CAS Number: 859212-16-1), and pharmaceutically acceptable salts thereof, having a structure represented by the formula:

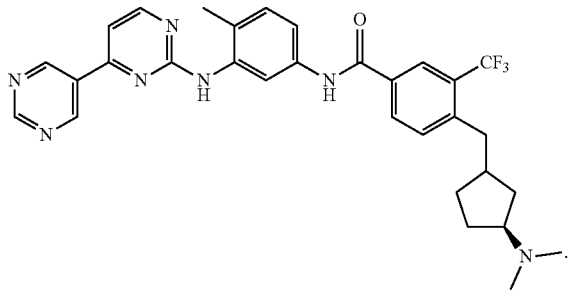 [SMILES: Cc1ccc(NC(=O)c2ccc(CC3CC[C@H](N(C)C)C3)c(C(F)(F)F)c2)cc1Nc1nccc(-c2cncnc2)n1]

This compound has been described as inhibiting the activity of BCR-ABL1, LYN, PDGFR, and KIT.

In certain embodiments, the BCR-ABL1 tyrosine kinase inhibitor is saracatinib (developed by AstraZeneca, also known as AZD0530; CAS No. 379231-04-6), and pharmaceutically acceptable salts thereof, having a structure represented by the formula:

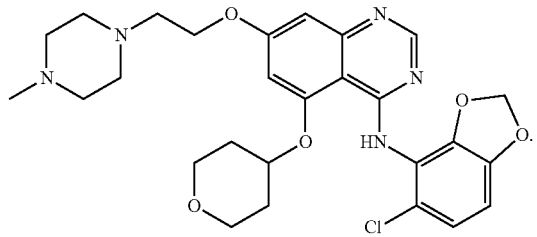 [SMILES: CN1CCN(CCOc2cc(OC3CCOCC3)c3c(Nc4c(Cl)ccc5c4OCO5)ncnc3c2)CC1]

This compound has been described as inhibiting the activity of BCR-ABL1 and the SRC-family kinases.

In certain embodiments, the BCR-ABL1 tyrosine kinase inhibitor is tozasertib (developed by Merck and Vertex; CAS Number: 639089-54-6), and pharmaceutically acceptable salts thereof, having a structure represented by the formula:

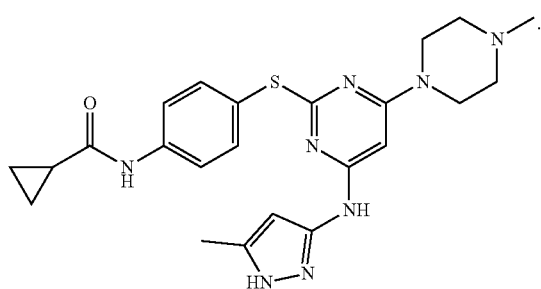 [SMILES: Cc1cc(Nc2cc(N3CCN(C)CC3)nc(Sc3ccc(NC(=O)C4CC4)cc3)n2)n[nH]1]

This compound has been described as inhibiting the activity of BCR-ABL1, Aurora kinases, FLT3, and JAK2.

In certain embodiments, the BCR-ABL1 tyrosine kinase inhibitor is danusertib, and pharmaceutically acceptable salts thereof, having a structure represented by the formula:

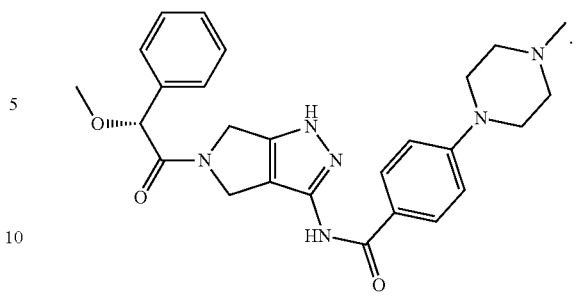

This compound has been described as inhibiting the activity of BCR-ABL1 and Aurora kinases.

4) Methods of Treatment

The present invention provides a method of treating a BCR-ABL related disorder (e.g., CML (e.g., TKI-resistant CML)) in an subject by administering a combination of a BCR-ABL1 TKI inhibitor or a pharmaceutically acceptable salt thereof and a WNT signaling pathway inhibitor to the subject in need thereof.

In one embodiment, the present invention provides a method of treating a BCR-ABL1 related disorder (e.g., CML) in a subject (e.g., patient) by administering to the subject in need of such treatment a therapeutically effective amount or dose of a combination of a BCR-ABL1 TKI inhibitor or a pharmaceutically acceptable salt thereof and a WNT/β catenin signaling pathway inhibitor.

In another embodiment, the WNT signaling inhibitor is an inhibitor of CD27 signaling, for example, a molecule that binds to CD27 and inhibits the binding of CD70 to CD27, e.g., an anti-CD27 antibody.

In another embodiment, the WNT signaling inhibitor is an inhibitor of CD27 signaling, for example, a molecule that binds to CD70 and inhibits the binding of CD70 to CD27, e.g., an anti-CD70 antibody.

In a further embodiment, the present invention provides a method of treating a BCR-ABL1 related disorder (e.g., CML) by administering to a subject in need of such treatment a quantity of a BCR-ABL1 TKI inhibitor or pharmaceutically acceptable salt thereof and a WNT signaling pathway inhibitor which is jointly therapeutically effective for said treatment.

The structure of the active agents identified by code nos., generic or trade names can be taken from the actual edition of the standard compendium "The Merck Index" or from databases, e.g., Patents International (e.g., IMS World Publications). The corresponding content thereof is incorporated by reference.

In one embodiment, the present invention provides a method of treating BCR-ABL1 related disorder (e.g., CML) by administering to a subject in need of such treatment a quantity of a BCR-ABL1 TKI inhibitor or pharmaceutically acceptable salt thereof and a WNT signaling pathway inhibitor which is jointly therapeutically effective for said treatment.

In a further embodiment, a BCR-ABL1 TKI inhibitor and a WNT signaling pathway inhibitor are in a single formulation or unit dosage form. In a further embodiment, a BCR-ABL1 TKI inhibitor and a WNT signaling pathway inhibitor are in separate formulations or unit dosage forms.

In a further embodiment, a BCR-ABL1 TKI inhibitor and/or a WNT signaling pathway inhibitor are administered at substantially the same time. In a further embodiment, a BCR-ABL1 TKI inhibitor and/or a WNT signaling pathway inhibitor are administered at different times. In a further embodiment, a BCR-ABL1 TKI inhibitor is administered to the subject prior to administration of a WNT signaling pathway inhibitor. In a further embodiment, a WNT signaling pathway inhibitor is administered to the subject prior to administration of a BCR-ABL1 TKI inhibitor.

5) Dosages

The optimal dose of the combination of agents for treatment of disease can be determined empirically for each individual using known methods and will depend upon a variety of factors, including, though not limited to, the degree of advancement of the disease; the age, body weight, general health, gender and diet of the individual; the time and route of administration; and other medications the individual is taking. Optimal dosages can be established using routine testing and procedures that are well known in the art.

The amount of combination of agents that can be combined with the carrier materials to produce a single dosage form will vary depending upon the individual treated and the particular mode of administration. In some embodiments the unit dosage forms containing the combination of agents as described herein will contain the amounts of each agent of the combination that are typically administered when the agents are administered alone.

Frequency of dosage can vary depending on the compound used and the particular condition to be treated or prevented. In general, the use of the minimum dosage that is sufficient to provide effective therapy is preferred. Patients can generally be monitored for therapeutic effectiveness using assays suitable for the condition being treated or prevented, which will be familiar to those of ordinary skill in the art.

The dosage form can be prepared by various conventional mixing, comminution and fabrication techniques readily apparent to those skilled in the chemistry of drug formulations.

The oral dosage form containing the combination of agents or individual agents of the combination of agents can be in the form of micro-tablets enclosed inside a capsule, e.g. a gelatin capsule. For this, a gelatin capsule as is employed in pharmaceutical formulations can be used, such as the hard gelatin capsule known as CAPSUGEL®, available from Pfizer.

Many of the oral dosage forms useful herein contain the combination of agents or individual agents of the combination of agents in the form of particles. Such particles can be compressed into a tablet, present in a core element of a coated dosage form, such as a taste-masked dosage form, a press coated dosage form, or an enteric coated dosage form, or can be contained in a capsule, osmotic pump dosage form, or other dosage form.

The drug compounds of the present invention (for example, a BCR-ABL1 TKI inhibitor or a pharmaceutically acceptable salt thereof and a WNT signaling pathway inhibitor) are present in the combinations (fixed or non-fixed), dosage forms, pharmaceutical compositions and pharmaceutical formulations disclosed herein in a ratio in the range of 100:1 to 1:100. For example, the ratio of a BCR-ABL1 TKI inhibitor:a WNT signaling pathway inhibitor can be in the range of 1:100 to 1:1, for example, 1:100, 1:90, 1:80, 1:70, 1:60, 1:50, 1:40, 1:30, 1:20, 1:10, 1:5, 1:2, or 1:1. In another example, the ratio of a WNT signaling pathway inhibitor:a BCR-ABL1 TKI inhibitor can be in the range of 1:100 to 1:1, for example, 1:100, 1:90, 1:80, 1:70, 1:60, 1:50, 1:40, 1:30, 1:20, 1:10, 1:5, 1:2, or 1:1.

The optimum ratios, individual and combined dosages, and concentrations of the drug compounds that yield efficacy without toxicity are based on the kinetics of the active ingredients' availability to target sites, and are determined using methods known to those of skill in the art.

The pharmaceutical compositions or combinations provided herein (i.e., a BCR-ABL1 TKI inhibitor or a pharmaceutically acceptable salt thereof and a WNT signaling pathway inhibitor) can be tested in clinical studies. Suitable clinical studies can be, for example, open label, dose escalation studies in patients with cancer. Such studies prove in particular the synergism of the active ingredients of the combination of the invention. The beneficial effects on cancer can be determined directly through the results of such studies as are known as such to a person skilled in the art. Such studies can be, in particular, suitable to compare the effects of a monotherapy using the active ingredients and a combination of the invention. In one embodiment, the dose of a BCR-ABL1 TKI inhibitor is escalated until the Maximum Tolerated Dosage is reached, and a WNT signaling pathway inhibitor is administered with a fixed dose. Alternatively, a BCR-ABL1 TKI inhibitor can be administered in a fixed dose and the dose of a WNT signaling pathway inhibitor can be escalated. Each patient can receive doses of the compounds either on set schedule (e.g., daily) or on an irregular basis. The efficacy of the treatment can be determined in such studies, e.g., after 12, 18 or 24 weeks by evaluation of symptom scores every 6 weeks.

The administration of a combination therapy of the invention can result not only in a beneficial effect, e.g. a synergistic therapeutic effect, e.g. with regard to alleviating, delaying progression of or inhibiting the symptoms, but also in further surprising beneficial effects, e.g. fewer side-effects, an improved quality of life or a decreased morbidity, compared with a monotherapy applying only one of the pharmaceutically active ingredients used in the combination of the invention.

A further benefit can be that lower doses of the active ingredients of the combination of the invention can be used, for example, that the dosages need not only often be smaller but can also be applied less frequently, which can diminish the incidence or severity of side-effects. This is in accordance with the desires and requirements of the patients to be treated.

It is one objective of this invention to provide a pharmaceutical combination comprising a quantity, which can be jointly therapeutically effective at targeting or preventing cancer, e.g., a BCR-ABL1 related disorder (e.g., CML) BCR-ABL1 related disorder (e.g., CML). In this combination, a BCR-ABL1 TKI inhibitor and a WNT signaling pathway inhibitor can be administered together, one after the other or separately in one combined unit dosage form or in two separate unit dosage forms. The unit dosage form can also be a fixed combination.

The pharmaceutical compositions for separate administration (or non-fixed dose) of both compounds, or for the administration in a fixed combination, i.e. a single composition comprising both compounds according to the invention can be prepared in a manner known per se and are those suitable for enteral, such as oral or rectal, and parenteral administration to mammals (warm-blooded animals), including humans, comprising a therapeutically effective amount of at least one pharmacologically active combination partner alone, e.g. as indicated above, or in combination with one or more pharmaceutically acceptable carriers or diluents, especially suitable for enteral or parenteral application.

In one embodiment, the present invention relates to a pharmaceutical composition or pharmaceutical formulation comprising (a) a BCR-ABL1 TKI inhibitor or a pharmaceutically acceptable salt thereof, and (b) a WNT signaling pathway inhibitor, and optionally one or more pharmaceutically acceptable carriers.

In a further embodiment, the present invention further relates to a pharmaceutical composition or pharmaceutical formulation comprising (a) a BCR-ABL1 TKI inhibitor or a pharmaceutically acceptable salt thereof, and (b) a WNT signaling pathway inhibitor, and optionally one or more pharmaceutically acceptable carriers, for use in the treatment of cancer.

In a further embodiment, the present invention relates to (a) a pharmaceutical combination comprising a BCR-ABL1 TKI inhibitor or a pharmaceutically acceptable salt thereof, and (b) a pharmaceutical composition comprising a WNT signaling pathway inhibitor administered in separate pharmaceutical compositions to a subject in need thereof.

6) Formulations

The drug combinations provided herein can be formulated by a variety of methods apparent to those of skill in the art of pharmaceutical formulation. As discussed above, a BCR-ABL1 TKI inhibitor and a WNT signaling pathway inhibitor can be formulated into the same pharmaceutical composition or into separate pharmaceutical compositions for individual administration. Suitable formulations include, for example, tablets, capsules, press coat formulations, intravenous solutions or suspensions, and other easily administered formulations.

One or both combination partners can be administered in a pharmaceutical formulation comprising one or more pharmaceutically acceptable carriers. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous saline solutions and aqueous dextrose and glycerol solutions are preferably employed as carriers, particularly for injectable solutions. Suitable pharmaceutical carriers are described in "Remington's Pharmaceutical Sciences" by E. W. Martin.

Suitable pharmaceutical formulations can contain, for example, from about 0.1% to about 99.9%, preferably from about 1% to about 60%, of the active ingredient(s). Pharmaceutical formulations for the combination therapy for enteral or parenteral administration are, for example, those in unit dosage forms, such as sugar-coated tablets, tablets, capsules or suppositories, or ampoules. If not indicated otherwise, these are prepared in a manner known per se, for example by means of conventional mixing, granulating, sugar-coating, dissolving or lyophilizing processes. It will be appreciated that the unit content of a combination partner contained in an individual dose of each dosage form need not in itself constitute an effective amount since the necessary effective amount can be reached by administration of a plurality of dosage units.

In accordance with the present invention, a therapeutically effective amount of each of the combination partners of the combination of the invention can be administered simultaneously or sequentially and in any order, and the components can be administered separately or as a fixed combination. Alternatively, an amount, which is jointly therapeutically effective for the treatment of cancer, of each combination partner of the combination of the invention can be administered simultaneously or sequentially and in any order, and the components can be administered separately or as a fixed combination.

For example, the method of treating a disease according to the invention can comprise (i) administration of the first agent in free or pharmaceutically acceptable salt form and (ii) administration of the second agent in free or pharmaceutically acceptable salt form, simultaneously or sequentially in any order, in jointly therapeutically effective amounts, preferably in synergistically effective amounts, e.g. in daily or intermittently dosages corresponding to the amounts described herein. The individual combination partners of the combination of the invention can be administered separately at different times during the course of therapy or concurrently in divided or single combination forms. Furthermore, the term administering also encompasses the use of a pro-drug of a combination partner that convert in vivo to the combination partner as such. The instant invention is therefore to be understood as embracing all such regimens of simultaneous or alternating treatment and the term "administering" is to be interpreted accordingly.

The effective dosage of each of the combination partners employed in the combination of the invention can vary depending on the particular compound or pharmaceutical composition employed, the mode of administration, the condition being treated, and the severity of the condition being treated. Thus, the dosage regimen of the combination of the invention is selected in accordance with a variety of factors including the route of administration and the renal and hepatic function of the patient. A clinician or physician of ordinary skill can readily determine and prescribe the effective amount of the single active ingredients required to alleviate, counter or arrest the progress of the condition.

Suitable administration frequencies for a BCR-ABL1 TKI inhibitor or a WNT signaling pathway inhibitor used in the methods described herein are on the order of about 10 times per day to about once per month (e.g., about 10, 9, 8, 7, 6, 5, 4, 3, 2, 1 times per day to about 31, 30, 29, 28, 27, 26, 25, 24, 23, 22, 21, 20, 19, 18, 17, 16, 15, 14, 13, 12, 11, 10, 9, 8, 7, 6, 5, 4, 3, 2, or 1 times per month).

Any patent, patent application, publication, or other disclosure material identified in the specification is hereby incorporated by reference herein in its entirety. Any material, or portion thereof, that is said to be incorporated by reference herein, but which conflicts with existing definitions, statements, or other disclosure material set forth herein is only incorporated to the extent that no conflict arises between that incorporated material and the present disclosure material.

EXAMPLES

The invention is further illustrated by the following examples. The examples have been set forth below for the purpose of illustration and to describe certain specific embodiments of the invention. The scope of the claims is not to be in any way limited by the examples set forth herein.

In the examples, the antibodies, lineage depletion and flow cytometry used the following reagents: αc-kit-PE-Cy7, αSca-1-perinidin-chlorophyll-protein (PerCP)-Cy5.5, and αGr-1-PE were from eBioscience. αCD27-FITC, Armenian-hamster-IgG-PE, αc-kit-APC-Alexa750, αCD3α-biotin, αCD19-biotin, αGr-1-biotin, αTer119-biotin, αCD34-

APC, αCD45-Pacific-Blue, Streptavidin-BDHorizonV500, and Annexin-V-Pacific-Blue were from BioLegend. 7-Aminoactinomycin D (7-AAD), αBrdU-APC (3D4), αCD70-PE (Ki-24), and the corresponding isotype control (MOPC21) were from BD Pharmingen.

Statistical analysis was performed using GraphPad Prism® 5.0 (GraphPad Software). Data are represented as mean±s.e.m. Data were analyzed using one-way ANOVA and Tukey's or Dunnett's multiple comparison test, two-way ANOVA and Bonferroni post-test or student's t-test (two-tailed). Significance of differences in Kaplan-Meier survival curves was determined using the log-rank test (two-tailed). p<0.05 was considered significant.

Example 1: Tyrosine Kinase Inhibitor (TKI) Treatment Increases CD70 Expression in Human BCR-ABL1+ Cells To analyze the impact of a tyrosine kinase inhibitor (TKI) treatment on CD70 expression, $1 \times 10^5$ human BCR-ABL1+ CML KBM5 cells were cultured in the presence of vehicle (V: $H_2O$) or imatinib (im; Novartis) at a concentration of 0, 0.1, 1 or 10 µM for 72 h. CD70 mRNA and protein expression in samples were then measured by real time RT-PCR or FACS analysis respectively.

1) FACS Analysis of CD70 Protein Expression

A monoclonal phycoerythrin (PE) conjugated mouse anti-human CD70 (anti-CD70-PE (clone Ki-24); catalog #555835) and the corresponding isotype control (MOPC21) were purchased from BD Pharmingen. Anti-CD70-PE FACS sorting of samples to determine CD70 protein expression was performed in a BD LSRII Flow Cytometer in combination with a BD FACS Aria cell sorter (BD Biosciences). Data were analyzed using FlowJo software (Treestar).

Figure 1:
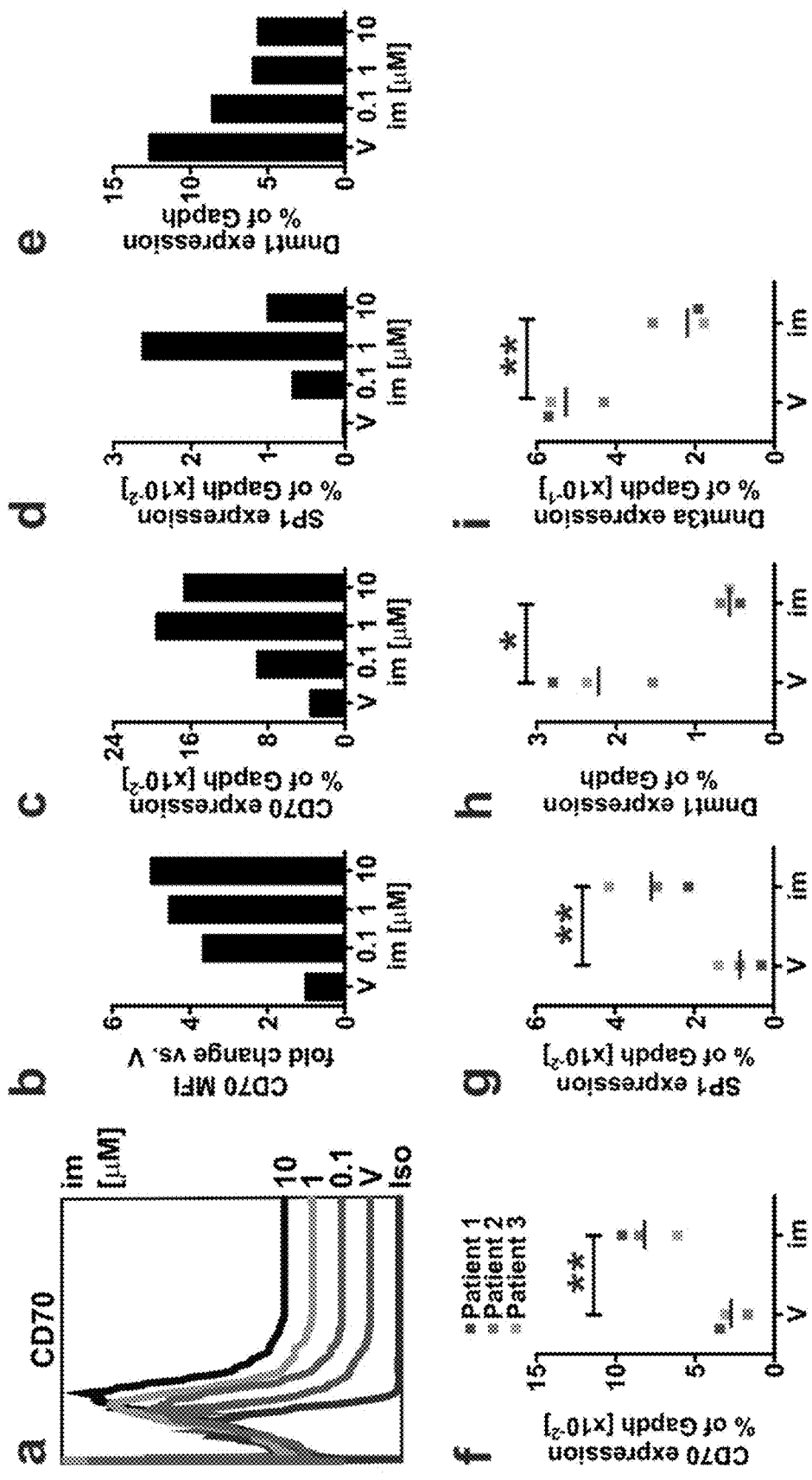
FIG. 1 shows that TKI treatment up-regulates CD70 in human CML cell lines and human $CD34^+$ CML stem/progenitor cells. (a-e) $1\times10^5$ KBM5 cells were cultured in the presence of vehicle (V: $H_2O$) or imatinib (im) at the indicated concentrations for 72 h. (a) Histograms and (b) mean fluorescence intensity (MFI) of CD70 protein expression (FACS). (c) CD70, (d) SP1 and (e) Dnmt1 mRNA expression (real-time RT-PCR). (f-i) $1\times10^4$ FACS-sorted $CD34^+$ stem/progenitor cells from the blood of newly diagnosed CML patients were cultured in liquid culture medium for 7 days in the presence of vehicle or imatinib (1 μM). (f) CD70, (g) SP1, (h) Dnmt1 and (i) Dnmt3a mRNA expression (real-time RT-PCR).

FIG. 1, *a* (histogram) and *b* (CD70 mean fluorescence intensity (MFI)) show that imatinib treatment of human BCR-ABL1+ CML KBM5 cells increased CD70 protein expression in a dose-dependent manner.

2) qRT-PCR Analysis of CD70 mRNA Expression

For qRT-PCR, total RNA of samples was extracted using the RNeasy Kit (Qiagen). Complementary DNA synthesis was performed using the High Capacity cDNA Reverse Transcription Kit (Applied Biosystems). The sequences of used real-time primers are available upon request. For qRT-PCR analysis, synthesized cDNAs amplified with specific gene primers using SYBR® Green 2X PCR Master Mix (Applied Biosystems). Real-time PCR reactions were performed in triplicates including no-template controls using an ABI Prism 7500 Sequence Detection System (Applied Biosystems). Relative quantification of gene expression was normalized against a reference gene (Gapdh) and calculated as an exponent of 2 (2ΔCt).

Imatinib treatment of human BCR-ABL1+ CML KBM5 cells also resulted in a dose dependent increase in CD70 mRNA expressiDNA methyltransferase 1 (Dnmt1) mRNA expression on (FIG. 1, *c*), an upregulation of SP1 (FIG. 1, *d*) and a down regulation of Dnmt1 mRNA expression (FIG. 1, *e*). Similar results were obtained using different BCR-ABL1+ leukemia cell lines such as KBM5 (FIG. 14, A-E), SD-1 (FIG. 14, F-J) and K562 (FIG. 14, K-O) and by treatment with the second-generation TKI nilotinib (Novartis).

Example 2: Tyrosine Kinase Inhibitor (TKI) Treatment Increases CD70 Expression in FACS-Sorted CD34+ Stem/Progenitor Cells from Newly Diagnosed CML Patients Cultured Ex Vivo Peripheral blood samples and one BM aspirate from untreated, newly diagnosed CML patients at the Department of Hematology (n=6, age: 54.6±19.4 years) were obtained after written informed consent. All patients harbored a BCR-ABL1 translocation as tested by molecular analysis.

$1 \times 10^4$ fluorescence-activated cell sorting (FACS)-sorted CD34+ stem/progenitor cells from the blood of newly diagnosed CML patients (n=6, age: 54.6±19.4 years, see Table 3 below for clinical characteristics of the included patients) were cultured ex vivo in liquid culture medium for 7 days in the presence of vehicle or imatinib (1 µM). Samples were analyzed for protein and mRNA expression as described in Example 1. In line with the findings in Example 1, imatinib treatment increased CD70 protein expression (FIG. 1, *f*) and SP1 mRNA expression (FIG. 1, *g*) whereas Dnmt 1 (FIG. 1, *h*) and Dnmt3a mRNA expression (FIG. 1, *i*) were down-regulated.

TABLE 3[1]

| ID | Sex | Age | Blood leukocytes [×10⁹/l] | BM cellularity [%] | BM blasts [%] | BCR-ABL1 type | BCR-ABL1 mutation | BCR-ABL1 mRNA |
|---|---|---|---|---|---|---|---|---|
| 1 | F | 42 | 106.2 | 90% | <2% | b3a2 | n.d. | n.d |
| 2 | M | 58 | 242 | 100% | <2% | b2a2 | n.d. | n.d. |
| 3 | M | 84 | 39.5 | 95% | <5% | b3a2 | n.d. | n.d. |
| 4 | M | 16 | 354.7 | 100% | <5% | b2a2 | negative | 172 |
| 5 | F | 70 | 25.6 | 80% | 5% | b3a2 | negative | 132 |
| 6 | F | 77 | 87.1 | n.d. | n.d. | b3a2 | n.d. | 269 |

Blood leukocytes normal range: $3.5\text{-}10.5 \times 10^9/l$
BM cellularity normal range: (100-patient age)% ± 20%
BM blasts (defined as CD34+ and/or c-kit+) normal range: ≤5%
BCR-ABL1 mRNA is displayed as % expression of GAPDH
n.d. not determined

[1]Age, blood leukocyte counts, the percentage of BM cellularity, and the percentage of BM blasts at the time of diagnosis, as well as the type of BCR-ABL1 translocation, are shown. In two patients who responded insufficiently to imatinib treatment (patient 4: only minor cytogenetic response after 3 months; patient 5: no major molecular response after 13 months), BCR-ABL1 mutational analysis was performed. Neither of these patients harbored a BCR-ABL1 mutation, and treatment regimen was changed to dasatinib for both patients.

Example 3A: Tyrosine Kinase Inhibitor (TKI)-Mediated CD70 Up-Regulation is Dependent on BCR-ABL1 Inhibition To determine whether the mechanism of TKI-mediated CD70 induction is dependent on BCR-ABL1 inhibition or an off-target effect, the experiments described in Example 1 were repeated using the imatinib-resistant KBM5 cell line harbors the BCR-ABL$^{T315I}$ mutation (referred herein as KBM5r), a mutation that is found in ~20% of all clinically observed BCR-ABL1 mutations that confer resistance to all three TKIs currently used in clinics (imatinib, nilotinib and dasatinib) (Deininger Exp. Hematol. 35, 144-154 (2007)).

At the therapeutic concentration of 1 µM, which is associated with an optimal response in CML patients (Koren-Michowitz et al., Hematol. Oncol. 30, 200-205 (2012)), imatinib treatment did not increase the expression of CD70 protein (FIG. 8, *a* and *b*), CD70 (FIG. 8*c*) or SP1 (FIG. 8*d*) mRNAs nor decrease the expression of DNMT1 mRNA (FIG. 8*e*) in KBM5r cells.

FIG. 8 therefore shows that imatinib treatment of the KBM5r resistant cell line results in a nearly unchanged CD70 protein and mRNA expression. In contrast, SP1 and Dnmt1 mRNA expression responded inversely upon imatinib treatment of KBM5r cells as compared to KBM5 cells.

TKI-mediated CD70 induction was further investigated by culturing $1 \times 10^5$ imatinib-resistant KBM5r cells for 72 hours in the presence of vehicle or ponatinib (po) (Selleck Chemicals), a pan-BCR-ABL1 inhibitor that was developed to overcome BCR-ABL1$^{T315I}$ mutation-mediated resistance (O'Hare et al. Cancer Cell 16, 401-412 (2009) and that has proven effective in clinical trials (Cortes et al. N. Engl. J. Med. 367, 2075-2088 (2012). 1×10$^5$ imatinib-resistant KBM5r cells were cultured in the presence of vehicle or ponatinib (po) at the indicated concentrations for 72 h. Samples were analyzed for protein and mRNA expression as described in Example 1. FIG. 1, *j-n* shows that ponatinib treatment at the therapeutic concentration of 0.1 µM induced CD70 protein expression (see histogram in FIG. 1, *j* and mean fluorescence intensity (MFI) of CD70 expression by FACS in FIG. 1, *k*) and mRNA expression (FIG. 1, *l*), up-regulated SP1 (FIG. 1, *m*) and down-regulated Dnmt1 mRNA (FIG. 1, *n*) in KBM5r cells.

CD70 protein expression was already up-regulated after 16 hours of treatment (FIG. 1, *o*), at a time point where ponatinib did not induce substantial cell death (FIG. 1, *p*). This indicates that the observed increase in CD70 expression after TKI treatment is caused by an up regulation of the protein rather than selection of CD70-expressing cells.

Thus, BCR-ABL1 inhibition by TKIs specifically results in CD70 up-regulation by altering the expression of DNA methyltransferases and the transcription factor SP1.

Example 3B: Tyrosine Kinase Inhibitor (TKI)-Mediated CD70 Up-Regulation is Mediated by Sp1

To prove that the expression of CD70 after TKI treatment was mediated functionally by SP1, SP1 expression was knocked down in KBM5r cells using transduction-ready lentiviral particles that express a short hairpin SP1 (shSP1) (Santa Cruz Biotechnology Inc.).

Specifically, 5×10$^4$ KBM5r cells were transduced overnight at 37° C. and 5% C02 with 2×10$^5$ infectious units of shSP1 or the respective control lentiviral particles having scrambled RNA (Santa Cruz Biotechnology Inc.) in the presence of 5 µg/ml polybrene (Sigma-Aldrich) according to the manufacturer's instructions. After 18 hours, medium was removed, and cells were cultured in medium supplemented with 1 µg/ml puromycin to select for stable expression of shSP1 or scrambled RNA.

KBM5r cells (1×10$^5$) stably transduced with shSP1 (shSP1), or the respective control scrambled RNA lentiviral particles (scr), were then cultured for 72 hours in the presence of vehicle or ponatinib (po; 0.1 µM). Treated cells were tested for MFI of CD70 protein expression (FACS) (FIG. 1, *q*), CD70 (FIG. 1, *r*) and SP1 (FIG. 1 *s*) mRNA expression (qRT-PCR). As shown in FIG. 1, (q-s), the SP1 knockdown with shSP1 in KBM5r cells did not up-regulate CD70 in the presence of ponatinib when compared to scrambled control RNA-transfected cells. SP1 expression is therefore required for the TKI-mediated CD70 up regulation.

Example 3C: The Wnt Pathway is Required for TKI-Mediated BCR-ABL1 Inhibition and the Regulation of CD70, Sp1 and Dnmt1

To investigate whether the Wnt pathway represents a link between TKI-mediated BCR-ABL1 inhibition and the regulation of CD70, SP1, and DNMT1, TKI-treated KBM5r cells were cultured in the presence of lithium chloride or the specific Wnt activator R-Spondin 1.

In a first experiment, 1×10$^5$ KBM5r cells were cultured in the presence of vehicle, ponatinib (po, 0.1 µM), lithium chloride (li, 10 µM), or both in combination (po/li) for 24 h (FIG. 2, A-C). In a second experiment, 1×10$^5$ KBM5r cells were cultured in the presence of vehicle, ponatinib (po, 0.1 µM), R-Spondin 1 (R, 10 ng/ml), or both in combination (po/R) for 72 h (FIG. 2, D-E). In both experiments, reactivation of Wnt signaling by lithium chloride or R-Spondin 1 restored TKI-mediated changes in gene expression (FIG. 2, A-F).

SP1 and DNMTs are regulated by miR-29 (Liu et al. Cancer Cell 17, 333-347 (2010); Tan et al. Biochem. Biophys. Res. Commun. 438, 673-679 (2013)). In addition, miR-29 has been shown to modulate Wnt signaling in a positive feedback loop (Kapinas et al. J. Biol. Chem. 285, 25221-25231 (2010)). miR-29 expression was therefore analyzed in KBM5r cells treated with imatinib, nilotinib, and ponatinib.

MicroRNA expression was assayed by first extracting total RNA using the RNeasy Micro Kit (Qiagen) and subjecting it to cDNA synthesis using the High Capacity cDNA Reverse Transcription Kit (Applied Biosystems). MicroRNA concentrations were measured using TaqMan miRNA Assays for miR-29a, miR-29b, miR-29c, or RNU48 (Applied Biosystems), and qRT-PCR results were normalized to RNU48 expression. Inhibition of BCR-ABL$^{T315I}$ by ponatinib resulted in down-regulation of all three miR-29s, whereas imatinib and nilotinib did not affect miR-29s (FIG. 2, G-I).

To further probe the role of these microRNAs, 2'-O-Methyl modified anti-miRs complementary to three candidate miRs (hsa-miR-29a-3p, hsa-miR-29b-3p, and hsa-miR-29c-3p; Mission Lenti microRNA Inhibitor) and a 2'-O-Methyl modified scrambled RNA sequence (scr) were synthesized and purified by Sigma-Aldrich. 1×10$^5$ KBM5r cells were seeded into 24-well plates, and transfections were performed with 100 nM anti-miR oligonucleotide and Lipofectamine LTX (Life Technologies) according to the manufacturer's instructions. 48 h after transfection, cells were harvested and subjected to total RNA extraction and cDNA synthesis for qRT-PCR. Individual silencing of the three miR-29 family members with anti-miRs revealed that SP1 expression was increased after miR-29c silencing, whereas DNMT1 expression was suppressed after silencing of miR-29a and miR-29b (FIGS. 2, J and K).

Example 4: CD70 Up-Regulation Results from Reduced Methylation of the CD70 Methylation and an Increase in Sp1 Expression The down-regulation of Dnmt by TKI treatment indicated that the up-regulation of CD70 expression may be caused by a change in the DNA methylation of the CD70 promoter. The methylation profile of the SP1 transcription factor binding sites within the KBM5r cell CD70 promoter was analyzed by bisulfite sequencing after treatment of KBM5r cells with either a control, ponatinib (0.1 µM) or azacytidine (1 µM).

1) DNA Methylation Analysis of the CD70 Promoter.

Bisulfite conversion of the isolated DNA samples from both KBM5 and KBM5r cells were assessed using the Epitect® Bisulfite Kit (Qiagen) according to the manufacturer's protocol. The promoter region covering binding sites for important transcription factors were selectively amplified using the following primers: forward primer (−227~−205): 5'-GTTTTAGAAGAATGAGGTGGAG-3' (SEQ ID NO.: 9); reverse primer (+14~+35): 5'-TCAACCTAT-CAAAAAACCAAC-3' (SEQ ID NO.: 10). For the amplification of bisulfite-treated genomic DNA (gDNA), the following PCR conditions were used: 1×: 95° C. for 10 min; 40×: 95° C. for 30 s, 58° C. for 40 s, 72° C. for 1 min; 1×72° C. for 5 min. The PCR cocktail was: 3 µl of DNA (of at least 10 ng/μL DNA for a final concentration of 3 ng/μL per reaction) in a 25 μl total volume using 0.5 pmol of each primer, 200 μM dNTPs, 0.2 U Hot Start Taq DNA polymerase, 1.5 mM MgCl2 and the buffer supplied with the enzyme. The amplified promoter region were gel-purified and subjected for fluorescent Sanger sequencing. The relative quantification of the methylated allele (C) versus unmethylated allele (T) was assessed by the QSVAnalyser software. The ratio for methylated cytosine was used for the two-way hierarchical clustering analysis. The variable CpG fragments at the CD70 promoter were clustered based on pair-wise Euclidean distances and linkage algorithm for all of the 21 samples (7 independent replicates per condition). The procedure was performed using the double dendrogram function of the Gene Expression Statistical software (NCSS, Kaysville, Utah, USA).

Statistical analysis was performed using GraphPad Prism® 5.0 (GraphPad Software). Data are represented as mean±s.e.m. Data were analyzed using one-way ANOVA and Tukey's or Dunnett's multiple comparison test, two-way ANOVA and Bonferroni post-test or student's t-test (two-tailed). Significance of differences in Kaplan-Meier survival curves was determined using the log-rank test (two-tailed). $p<0.05$ was considered significant.

The results are shown in FIG. 2, L-N. FIG. 2, L shows the methylation status of the CD70 promoter at the SP1 transcription factor binding site of KBM5r cells upon treatment with vehicle, ponatinib (0.1 μM) or azacytidine (1 μM) as determined by bisulfite sequencing. FIG. 2, M shows a heat-map of relative quantification of methylated cytosines at five critical CpG sites in the CD70 promoter. FIG. 2, N shows a semi-quantitative analysis of DNA methylation for CpG1 and CpG2 at the SP1 binding site. One representative experiment out of three is shown in FIG. 2, L-N. Pooled data from three independent experiments are shown. Data are displayed as mean±s.e.m. *

Bisulfite sequencing revealed a nearly unmethylated CD70 promoter in vehicle-treated KBM5 cells (see FIG. 8, f) displaying considerable expression of CD70 as analyzed by FACS (see FIG. 1, a and b) and real-time RT-PCR (FIG. 1, c).

In contrast, the CD70 promoter was strongly methylated in vehicle-treated KBM5r cells (see FIG. 2, L) that hardly expressed any FACS-detectable CD70 protein (FIG. 8, a) or mRNA (FIG. 8, c). Consistent with the up-regulation of CD70 mRNA and protein expression, ponatinib treatment significantly reduced CD70 promoter DNA methylation in KBM5r cells, particularly at the SP1 binding site (FIG. 2, L-N). Control KBM5r cells cultured in the presence of the Dnmt inhibitor azacytidine, a de-methylating agent23, showed similar reductions in CD70 promoter methylation (FIG. 2, L-N).

In summary, these data indicate that TKI treatment and consecutive BCR-ABL1 inhibition in CML cells results in CD70 up-regulation by reducing its promoter methylation and increasing SP1 expression

Example 5: Co-Inhibition by CD70/CD27 and BCR-ABL1 Synergistically Eradicates SD-1 Leukemia Cells 1) Antibodies and Reagents for Treatment Murine anti-CD70 (clone FR70) was purchased from BioXCell and control IgG from rat serum (rat-IgG) was from Sigma. Human anti-CD27 (clone 1A4) and the corresponding isotype control (clone 15H6) were purchased from Beckman Coulter. Imatinib and nilotinib were kindly provided by Novartis.

2) Combined CD70/CD27 and BCR-ABL1 Inhibition Reduced Leukemic Cell Growth by Inhibiting Cell Proliferation and Enhancing Cell Death To assess the activity of the combination of TKIs with CD70 inhibition on the proliferation of BCR-ABL leukemic cells, $1\times10^5$ BCR-ABL1$^+$ SD-1 cells, that express both CD27 and CD70 (see FIG. 3, l), were cultured for 72 h in the presence of either vehicle (V: H2O+IgG), 10 μg/ml of anti-CD27 blocking mAb (A: H2O+anti-CD27; clone 15H6), 1 μM of imatinib (im: im+IgG) or 1 μM of nilotinib (ni: ni+IgG) alone or in combination with the anti-CD27 blocking mAb with a constant ratio.

To analyze cell proliferation in vitro using BrdU, BrdU was added to the in vitro culture for the last 4 h of incubation (10 μM) and BrdU staining was performed according to the manufacturer's instructions (BD Pharmingen BrdU Flow Kit). Cell numbers (FIG. 3, a and d), BrdU incorporation (FIG. 3, b and e) and cell viability (FIG. 3, c and f) were determined by trypan blue staining and FACS. Apoptotic and necrotic cells were identified as Annexin-V+ and Annexin-V+7-AAD+ cells, respectively. AnnexinV-Pacific-Blue and αBrdU-APC were purchased from BioLegend.

As previously reported (Schürch et al. J. Clin. Invest. 122, 624-638 (2012)), blocking the CD70/CD27 interaction reduced the growth of SD-1 cells by inhibiting cell proliferation (FIG. 3, a-b). In contrast, blocking CD27 signaling alone did not affect cell viability (FIG. 3, c). In line with its documented ability to induce apoptosis of BCR-ABL1$^+$ cells, (Belloc et al., Cancer Biol. Ther. 6, 912-919 (2007)), imatinib treatment resulted in cell death of SD-1 cells as analyzed by FACS (FIG. 3, c). Imatinib also reduced cell growth and proliferation of SD-1 cells to a similar extent as αCD27 mAb treatment (FIG. 3, a-b). Interestingly, compared to single treatments, anti-CD27 mAb/imatinib co-treatment significantly (P<0.001) reduced cell growth by inhibiting cell proliferation and enhancing cell death (FIG. 3, a-c). Similar results were obtained by treating SD-1 cells with anti-CD27 mAb and the second-generation TKI nilotinib (FIG. 3, d-f).

The activity of a CD27 mAb and imatinib or ponatinib, respectively on KBM5 and KBM5r cell proliferation was also assessed. $1\times10^5$ (FIG. 3, j) KBM5 cells or (FIG. 3, k) KBM5r cells were cultured for 72 h in the presence of either vehicle (V: H$_2$O+IgG), 10 μg/ml of αCD27 blocking mAb (A: H$_2$O+αCD27; clone 15H6), 1 μM of imatinib (im) or 0.1 μM of ponatinib (po) alone or both in combination (A/im; A/po). Cell numbers were determined by trypan blue staining after 72 h. The results show that BCR-ABL1 and CD70/CD27 co-inhibition reduces the expansion of both KBM5 and KBM5r CML cells in vitro (FIG. 3, j-k).

3) The Targeting of BCR-ABL1- and CD27-Signaling Results in the Synergistic Growth Inhibition of SD-1 Cells To investigate whether co-treatment resulted in synergistic activity or whether it just reflected additivity, a drug combination study according to the Chou-Talalay method was performed. The effects of drug treatments as a fraction of vehicle-treated cells were calculated $1\times10^5$ SD-1 cells were treated with a control, anti-CD27 or imatinib alone or in combination in a constant ratio. Cell numbers per well were counted after 72 h and the effect of drug treatment was calculated as a ratio of vehicle-treated cells (see FIG. 3. m-n and Table 4). The fraction affected ($F_a$), the half maximum inhibitory concentration ($IC_{50}$), the slope (m) and the correlation coefficient (r) for the single treatment as well as the $F_a$ and the confidence interval (CI) for the drug combination were determined using the CompuSyn© software (Chou and Martin ComboSyn, Inc.: Paramus, N.J. Sep. 2, 2007 (2007)). CI<1, synergy; CI=1, additivity; CI>1, antagonism.

Combination treatment showed synergistic growth inhibition at all concentrations tested (see FIG. 3, g and Table 4 below). FIG. 3, n shows an Isobologram analysis of FIG. 3, m using the CompuSyn© software at effective doses (ED) 50, 75 and 90.

TABLE 4

Growth inhibition of SD-1 cells treated with anti-CD27 or imatinib monotherapy, or a combination of both drugs

| αCD27 Dose [μg/ml] | $F_a$ | imatinib Dose [M] | $F_a$ | combination $F_a$ | CI |
|---|---|---|---|---|---|
| 0.15 | 0.001 | 0.02 | 0.001 | 0.067 | 0.219 |
| 0.29 | 0.033 | 0.04 | 0.040 | 0.189 | 0.164 |
| 0.59 | 0.118 | 0.08 | 0.149 | 0.270 | 0.222 |
| 1.18 | 0.186 | 0.16 | 0.201 | 0.351 | 0.324 |
| 2.35 | 0.271 | 0.32 | 0.243 | 0.459 | 0.444 |
| 4.70 | 0.372 | 0.64 | 0.351 | 0.594 | 0.561 |
| 9.41 | 0.457 | 1.28 | 0.432 | 0.716 | 0.708 |
| 18.81 | 0.559 | 2.55 | 0.527 | 0.824 | 0.845 |
| 37.63 | 0.677 | 5.10 | 0.689 | 0.898 | 0.989 |
| 75.26 | 0.745 | 10.20 | 0.791 | 0.959 | 0.867 |
| $IC_{50}$ | 1.275 | $IC_{50}$ | 9.407 | | |
| m | 1.196 | m | 1.183 | | |
| r | 0.838 | r | 0.834 | | |

Example 6: Combined CD70/CD27 and BCR-ABL1 Inhibition Synergistically Reduces Wnt Signaling and Eradicates Leukemia Cells In Vitro CD70/CD27 interaction on murine CML LSCs activates the Wnt signaling pathway (Schürch et al. J. Clin. Invest. 122, 624-638 (2012)). Also TKIs such as imatinib have been shown to reduce aberrant BCR-ABL1-induced Wnt signaling in CML cells (Coluccia et al. EMBO J. 26, 1456-1466 (2007)). In addition, CD27 signaling activates the WNT pathway in CML leukemic stem cells via TNFR-associated factor 2 (TRAF2) and the TRAF2- and NCK-interacting protein kinase (TNIK). Therefore, . . . to analyze if the synergistic effect on leukemic stem cell viability and proliferation of anti-CD27 mAb/imatinib co-treatment is mediated via WNT pathway inhibition, a lentiviral WNT signaling reporter assay was performed to analyze the expression of selected WNT target genes by real-time RT-PCR.

Lentiviral reporter assay. SD-1 cells were transfected with Tcf/Lef lentiviral particles expressing firefly-luciferase or the respective positive and negative control lentiviral particles (Cignal® Lenti Tcf/Lef reporter (luc) kit, SABiosciences) at an MOI of 10, in the presence of 8 mg/ml SureEntry™ transduction reagent (SABiosciences) according to the manufacturer's instructions. Stable cell lines were generated under puromycin selection (2.5 mg/ml, Santa Cruz Biotechnology). Luciferase activity was measured on an Infinite® 200 microplate reader (Tecan) using the Steady-Glo® Luciferase Assay System (Promega) according to the manufacturer's instructions.

αCD27 and imatinib single treatments similarly reduced Wnt signaling and Wnt target gene transcription. αCD27/imatinib co-treatment inhibited Wnt pathway activation significantly ($P<0.001$) stronger than each of the single compounds alone (FIG. 3, h-i). The expression of selected genes involved in stem cell regulation and differentiation was also assessed by qRT-PCR. $1\times10^5$ SD-1 cells were cultured in the presence of vehicle, αCD27 (10 μg/ml), imatinib (im, 1 μM), or αCD27/im in combination for 72 h. (FIG. 3, m-o). Data are displayed as fold expression (mean±s.e.m.) vs. vehicle-treated cells.

The expression of selected genes involved in stem cell regulation and differentiation was assessed (qRT-PCR). The data in FIG. 3, o shows that Notch, Hedgehog, and MAP (mitogen-activated protein) kinase pathways were unaffected or only minimally affected by the αCD27/imatinib treatment. PCR primers used are shown in Table 5 below.

TABLE 5

(SEQ ID NOs: 11-26, respectively, in order of appearance)

| Species | Gene name | SYBR Green primer seq. (5'→3') or Taqman probe ID | | Len | Tm | Amp (bp) |
|---|---|---|---|---|---|---|
| Human | CD70 | FW: | TGCTTTGGTCCCATTGGTC | 19 | 60. | 108 |
| | | RW: | TACGTCCCACCCAAGTGAC | 19 | 61. | |
| | DNMT1 | FW: | GTATCTAGCAAGGGTCACGG | 20 | 60. | 145 |
| | | RW: | TGTCCTCACATTCATCCACC | 20 | 59. | |
| | GAPDH | FW: | TCATTTCCTGGTATGACAACGA | 22 | 59. | 120 |
| | | RW: | CTTCCTCTTGTGCTCTTGCTG | 21 | 61. | |
| | SP1 | FW: | AGAGGCCATTTATGTGTACCTG | 22 | 60. | 104 |
| | | RW: | AGGCAAATTTCTTCTCACCTGTG | 23 | 61. | |
| Mouse | Cd70 | FW: | GTTGGTTTCATTGTAGCGGAC | 21 | 60. | 107 |
| | | RW: | CCTTCCGAGGAACTGTGAG | 19 | 59. | |
| | Dnmt1 | FW: | AGATTGAGACCACTGTTCCTCC | 22 | 61. | 115 |
| | | RW: | CTTGGCTTCGTCGTAACTCTC | 21 | 61. | |
| | Gapdh | FW: | AGAACATCATCCCTGCATCC | 20 | 69. | 159 |
| | | FW: | TCATCATACTTGGCAGGTTTCTC | 23 | 60. | |
| | Sp1 | FW: | AGTGAGGGAAGAGCCTCAG | 19 | 60. | 106 |
| | | FW: | AAGTGTGCTCGGAGATGTG | 19 | 60. | |
| | Cd27 | Probe ID: | Mm01189212_g1 | | | |
| | Gapdh | Probe ID: | Mm99999915_g1 | | | |
| | Myc | Probe ID: | Mm00487803_m1 | | | |
| | Runx1 | Probe ID: | Mm01213405_m1 | | | |
| | Tnik | Probe ID: | Mm01286430_m1 | | | |
| | Traf2 | Probe ID: | Mm00801978_m1 | | | |

Example 7: Combined CD70/CD27 and BCR-ABL1 Inhibition Promotes Cell Death and Inhibits Colony Formation of Human CD34+ CML Stem/Progenitor Cells In Vitro The functional role of increased CD27-signaling in response to imatinib-induced CD70 up-regulation was determined in FACS-sorted human CD34$^+$ CML stem/progenitor cells.

1) In Vitro Liquid Culture of Primary Human CD34+ CML Stem/Progenitor Cells $10^4$ FACS-purified CD34+ stem/progenitor cells from the peripheral blood and bone marrow of CML patients were cultured in duplicates in StemSpan SFEM medium (Stem Cell Technologies) supplemented with human cytokines (StemSpan CC100; Stem Cell Technologies) in the presence of vehicle (V: H2O+IgG), 10 μg/ml of anti-CD70 blocking mAb (A: H2O+anti-CD70; clone 41D12-D), 1 μM of imatinib (im: im+IgG) or both in combination (A/im: anti-CD70+imatinib) in 96-well plates at 37° C. and 5% C02.

2) Proliferation and Cell Viability of Cultured Human CD34+ CML Stem/Progenitor Cells 10 μM BrdU (BD) was added to culture for the last 4 h of incubation. Numbers of viable cells were determined by trypan blue staining and BrdU staining was performed according to the manufacturer's instructions (BrdU Flow kit; BD) after 7 d of culture. Apoptotic and necrotic cells were identified as Annexin-V$^+$ and Annexin-V$^+$7-AAD$^+$ cells, respectively. AnnexinV-Pacific-Blue and αBrdU-APC were purchased from BioLegend.

3) Colony Formation of Cultured Human CD34+ CML Stem/Progenitor Cells

To assess colony formation (see FIG. 4, *f*), duplicates of $4 \times 10^3$ FACS-sorted CD34+ CML stem/progenitor cells were cultured overnight in 96-well V-bottom plates in the presence of the compounds as described for (b-e) and were then transferred into methylcellulose containing the respective drugs. Colony forming capacity was determined after 14 days by inverted light microscopy. *p<0.05, p<0.01, *p<0.001 (one-way ANOVA).

4) Results

FIG. 4, *a* confirms the FACS-sorted CD34+ cells from blood or bone marrow (BM) of newly diagnosed CML patients express CD27 and CD70 mRNA (measured by qRT-PCR as described in Example 1).

The results further show that, in liquid cultures, single treatments with either a blocking human anti-CD70 mAb or imatinib inhibited growth and proliferation of CD34$^+$ CML stem/progenitor cells (FIG. 4, *b-c*). The human anti-CD70 mAb (clone 41D12-D) that specifically blocks the CD70/CD27 interaction was engineered by mutation to remove effector functions such as antibody-dependent cell-mediated or complement-mediated cytotoxicity and antibody-dependent cell-mediated phagocytosis. In line with the results using the blocking αCD27 mAb and SD-1 cells (FIG. 3, *a-f*), single anti-CD70 mAb treatment inhibited cell proliferation without affecting cell viability, whereas single imatinib treatment reduced cell proliferation and induced cell death (FIG. 4, *d-e*). Importantly, anti-CD70 mAb/imatinib co-treatment potently eradicated leukemia cells in liquid cultures by synergistically inhibiting cell proliferation and increasing cell death (FIG. 4, *b-e*). In addition, colony formation by CD34$^+$ CML stem/progenitor cells in semi-solid cultures was significantly impaired by co-treatment compared to single compound treatments (FIG. 4, *f*). Importantly, CD34$^+$ stem/progenitor cells from patients that underwent BM biopsy for other reasons than leukemia (healthy donors) were only marginally affected by anti-CD70 mAb or imatinib treatment in vitro (see FIG. 4, *g-k*).

Example 8: Anti-CD70 Mab/Imatinib Combination Therapy Synergistically Eradicates Human CD34+ CML Stem/Progenitor Cells in Xenografts In Vivo 1) Murine Xenograft CML Model $2 \times 10^6$ MACS-purified CD34$^+$ stem/progenitor cells (using anti-CD34 beads from Miltenyi Biotec) from the peripheral blood of a newly diagnosed CML patient (patient 4) were injected intravenously (i.v.) into previously sublethally irradiated (2.75 Gy) NSG mice (NOD/LtSz-scid IL2Rgnu$^{null}$), a murine CML xenograft model. (NSG) mice were kindly provided by J. Schwaller (Department of Biomedicine, University of Basel, Switzerland). Starting one week after transplantation, imatinib (50 mg/kg) was administered once daily by oral gavage. The anti-CD70 mAb (clone 41D12-D) (10 mg/kg) was administered intraperitoneally (i.p.) every $3^{rd}$ day. Sterile H2O and a control mAb specific for the F protein of respiratory syncytial virus (Pavilizumab, Synagis®) were used as mock-treatment. After 2 weeks of treatment, mice were euthanized and BM from femurs and tibias were analyzed by FACS for human cell engraftment using anti-human CD45, CD34, CD33, CD3 and CD19 antibodies. Representative dot plots are shown in FIG. 5, *b*. FIG. 5, *a* shows the study design.

Anti-CD3α-biotin, anti-CD19-biotin, anti-CD34-APC, anti-CD45-Pacific-Blue, anti-CD33-PE, Streptavidin-BD-HorizonV500 were purchased from BioLegend. Human anti-CD70 (clone 41D12-D) and a corresponding control mAb specific for the F protein of respiratory syncytial virus (Pavilizumab, Synagis®) were kindly provided by arGEN-X (Breda, The Netherlands).

FIG. 5 shows the frequencies (FIG. 5, *c*) and absolute numbers of human CD45$^+$CD33$^+$ CML myeloid cells (FIG. 5, *d*) as well as the absolute numbers of human CD45$^+$ CD34$^+$ CML stem/progenitor cells (FIG. 5, *e*) in the BM of NSG mice. Data are displayed as mean±s.e.m. *p<0.05, p<0.01, *p<0.001 (one-way ANOVA). 2) Results After two weeks of treatment, vehicle-treated NSG mice had a frequency of 11.4±0.7% of human CD45+CD33+ CML myeloid cells in the BM (FIG. 5, *b*). Single anti-CD70 mAb or imatinib treatment significantly reduced CD45+CD33+ cell frequencies and absolute numbers in the BM of NSG mice (FIG. 5, *b-d*). Anti-CD70 mAb/imatinib co-treatment further reduced CD45+CD33+ CML myeloid cells (FIG. 5, *b-d*). More importantly, anti-CD70 mAb/imatinib co-treatment completely eradicated the leukemia-initiating CD34+ CML stem/progenitor cells in the BM of 5 out of 6 co-treated NSG mice (FIG. 5, *e*), whereas neither imatinib nor anti-CD70 mAb treatment alone eliminated all the CD34+ CML cells.

The in vivo findings were validated using a previously described murine CML xenograft model (Zhang et al. Cancer Cell 17, 427-442 (2010); Wang et al. Cancer Cell 21, 266-281 (2012)) in non-obese diabetic (NOD)/LtSz-scid IL2Rgnull (NSG) mice (Schultz et al. Immunol. 174, 6477-6489 (2005)). MACS-sorted CD34$^+$ CML stem/progenitor cells ($2 \times 10^6$) from the blood of patients 3, 4, and 5 carrying different BCR-ABL1 translocations (see Table 1) were injected intravenously into sub-lethally irradiated (2.75 Gy) NSG mice.

After 7 days of engraftment, NSG mice were randomized to receive vehicle, imatinib, or αCD70 treatment alone or αCD70/imatinib co-treatment. Plasma concentrations of imatinib in xenografted NSG mice were determined by liquid chromatography-tandem mass spectrometry and found to be close to the published therapeutic concentration of 1 μM (FIG. 5, o). After 2 weeks of treatment, animals were sacrificed, and the BM was analyzed for human CD45+ CD33+ CML myeloid cells and CD45+ CD34+ CML stem/progenitor cells (FIG. 5, a-e). At that time point, vehicle-treated NSG mice had an average of 11.8±1.1% of human CD45+ CD33+ CML myeloid cells in the BM (FIG. 5, b). Single αCD70 or imatinib treatment reduced cell frequencies and absolute numbers of CD45+ CD33+ leukemia cells and leukemia-initiating CD34+ CML stem/progenitor cells (FIG. 5, c-e). αCD70/imatinib co-treatment further reduced CD45+ CD33+ CML myeloid cells (FIG. 5, c-d) and eradicated the leukemia-initiating CD34+ CML stem/progenitor cells in the BM of 9 out of 12 NSG mice (FIG. 5e). CD34+ CML stem/progenitor cells isolated ex vivo from xenografted vehicle-treated NSG mice expressed CD70 (FIG. 5, f and p) but only low levels of CD27 (FIG. 5, q and r). CD70 and CD27 were not expressed on more differentiated CD34− CML cells (FIG. 5, f and r). Imatinib treatment of xenografted NSG mice specifically increased CD70 expression on CD34+ CML stem/progenitor cells but not on CD34− CML cells (FIG. 5, f and g). In contrast, the expression of CD27 remained unchanged after TKI treatment (FIG. 5, r). In addition, imatinib treatment induced an up-regulation of SP1 and decreased the expression of DNMT1 and miR-29a, miR-29b, and miR-29c in CD34$^+$ CML stem/progenitor cells in vivo (FIG. 5, h-l).

To analyze if CD70 expression correlates with Wnt pathway activation in CML patients harboring the b3a2 or the b2a2 BCR-ABL1 translocation, expression data derived from a public repository for microarray data was used (accession number E-MEXP480; see web site for ArrayExpress of Functional Genomics Data at the EMBL European Bioinformatics Institute (EBI)). Independent of the BCR-ABL1 translocation, CD70 expression positively correlated with the expression of Wnt target genes (FIG. 5, m-n).

Example 9: TKI Treatment Increases CD70 Expression in Murine CML LSCs

Because human CD34$^+$ CML stem/progenitor cells do not engraft long-term in NSG mice, it is not possible to study survival in this xenotransplant model. Therefore, BM from donor BL/6 mice was transduced with BCR-ABL1-GFP and injected into sublethally irradiated (4.5 Gy) syngeneic recipients.

The retroviral vector pMSCV-p210BCR-ABL1-IRES-GFP and the packaging vector pIK6 were a gift from J. Schwaller (Department of Biomedicine, University of Basel, Switzerland).

Production of Retrovirus Particles and Titration

The retroviral vector pMSCV-p210BCR-ABL1-IRES-GFP and the packaging vector pIK6 were a gift from J. Schwaller (Department of Biomedicine, University of Basel, Switzerland). Human embryonic kidney (HEK) 293 cells were co-transfected with pMSCV-p210BCR-ABL1-IRES-GFP and pIK6 using SuperFect (Qiagen). 48 h and 72 h later, supernatants containing retroviral particles were harvested, filter-sterilized, and stored at −80° C. Retroviral titers were determined by infection of Ba/F3 cells using polybrene (Sigma) and FACS analysis for BCR-ABL1-GFP+ cells 48 h later.

Murine CML Model

Donor mice were treated with 150 mg/kg of 5-fluorouracil intraperitoneally (i.p.). Six days later, BM was harvested and transduced twice with BCR-ABL1-GFP retrovirus by spin infection. 1×10$^5$ cells were injected intravenously (i.v.) into the tail vein of sublethally irradiated (4.5 Gy) syngeneic recipients. Treatment of CML mice was started 15 days after transplantation. Imatinib (50 mg/kg) was administered once daily by oral gavage. Anti-CD70 mAb (clone FR70) (300 mg/injection) was administered i.p every 3$^{rd}$ day. Sterile H$_2$O and rat-IgG were used as control treatments. To detect residual LSC activity in surviving CML mice (90 days after primary transplantation), 1×10$^7$ whole BM (WBM) cells were injected i.v. into lethally irradiated (twice 6.5 Gy with 4 hours interval) recipient mice. To compare LSC activity in mice receiving imatinib monotherapy and vs. αCD70/imatinib combination therapy, primary CML mice were treated for ten days, were sacrificed and 3×10$^6$ WBM cells were injected i.v. into sublethally irradiated (4.5 Gy) recipient mice.

Results

The effects of imatinib single treatment on the expression of CD70 protein and CD70, Sp1, and Dnmt1 mRNA was studied in murine LSCs in vivo. Similar to murine hematopoietic stem cells (HSCs), murine LSCs reside in a BM cell population characterized by the lack of lineage markers and by the expression of stem cell antigen-1 (Sca-1) and c-kit [lin$^-$ Sca-1$^+$ c-kit$^{hi}$ cells (LSKs); see FIG. 6, m]. CML-bearing mice were treated with vehicle or imatinib, and CD70 expression in BCR-ABL1-GFP+ LSKs was analyzed. Consistent with the data obtained for KBM5 cells and human CD34$^+$ CML stem/progenitor cells in vitro, BCR-ABL1-GFP$^+$ LSKs from imatinib treated CML mice expressed higher amounts of CD70 protein and mRNA as compared to BCR-ABL1-GFP+ LSKs from vehicle treated mice (FIG. 6, a-c, and m). Moreover, imatinib treatment increased Sp1 and decreased Dnmt1 mRNA in BCR-ABL1-GFP+ LSKs (FIG. 6, d-e). CD70 up-regulation upon imatinib treatment was specific for BCR-ABL1-GFP+ LSKs (FIG. 6, m and n-w), and imatinib did not alter CD70 expression on BCR-ABL1-GFP+ Sca-1$^-$ leukemia progenitors (FIG. 6, n). Furthermore, CD70, Sp1, and Dnmt1 expression did not change in endogenous non-malignant GFP$^-$ LSKs upon imatinib treatment (FIG. 6, a, m, o-r). As previously demonstrated, the CD70/CD27 interaction on murine CML LSCs activates the Wnt signaling pathway via TNF receptor-associated factor 2 (TRAF2) and the TRAF2- and NCK-interacting protein kinase (TNIK). Although imatinib treatment did not affect CD27 expression on BCR-ABL1-GFP+ LSKs, Traf2 and Tnik were up-regulated at the mRNA level, whereas Wnt target genes such as Runx1 and Myc were down-regulated (FIG. 6s-6w). These results are in line with and further support the hypothesis that TKIs specifically alter the expression of CD70, SP1, and DNMT1 via BCR-ABL1 inhibition and increase the expression of CD27 downstream signaling molecules such as TRAF2 and TNIK.

FIG. 6, f shows a Kaplan-Meier survival curves of primary BL/6 CML mice. Pooled data from 2 independent experiments with n=11-15 mice per group are shown. FIG. 6, g shows the survival of lethally irradiated (2×6.5 Gy) secondary recipients (n=8) that received 1×10$^7$ whole BM (WBM) cells from co-treated primary CML mice (n=8) that were still alive 90 days after primary transplantation.

Primary BL/6 CML mice were treated with either imatinib alone or were co-treated as described above starting 15 days after transplantation. Ten days later, the number of BCR-ABL1-GFP$^+$ LSKs (FIG. 6, h), BCR-ABL1-GFP$^+$ LT-LSCs (FIG. 6, i) and BCR-ABL1-GFP$^+$ ST-LSCs (FIG. 6, j) in the BM were measured. Equal numbers of total lin$^-$ cells were plated in methylcellulose and BCR-ABL1-GFP$^+$ colonies were enumerated 7 days later by inverted fluorescence microscopy (FIG. 6, k).

In a second series of experiments, primary BL/6 CML mice were treated with either imatinib alone or in combination with anti-CD70 mAb as described above starting 15 days after transplantation. Ten days later, 3×10$^6$ WBM cells from imatinib or anti-CD70 mAb/imatinib treated animals were transplanted into sublethally irradiated (4.5 Gy) recipient mice (n=5-6 per group) and survival was monitored. The number of mice that succumbed to CML of total transplanted mice are shown in FIG. 6, f, g and l). Data are displayed as mean±s.e.m. *p<0.05, p<0.01, *p<0.001 (log-rank test, student's t-test).

Murine LSCs reside in a BM cell population characterized by the lack of lineage markers (lin$^-$) and by the expression of stem cell antigen 1 (Sca-1) and c-kit (LSKs). CML-bearing mice were either treated with vehicle or imatinib (50 mg/kg) daily by oral gavage starting 15 days after transplantation. Ten days later, mice were sacrificed and CD70 expression in BCR-ABL-GFP$^+$ LSKs was analyzed by FACS and real-time RT-PCR.

Consistent with the data obtained for KBM5 cells and human CD34$^+$ CML stem/progenitor cells in vitro, BCR-ABL1-GFP$^+$ LSKs from imatinib-treated CML mice expressed significantly higher levels of CD70 mRNA and protein as compared to BCR-ABL1-GFP$^+$ LSKs from vehicle-treated mice (see FIG. 10, a-c). Moreover, imatinib treatment increased SP1 mRNA expression and decreased Dnmt mRNA in BCR-ABL1-GFP$^+$ LSKs (FIG. 10, d-f). CD70, SP1 and Dnmt expression did not change in endogenous non-malignant GFP$^-$ LSKs upon imatinib treatment (FIG. 10, a and g-h). These results are in line with and further support the hypothesis that TKIs specifically alter the expression of CD70, SP1 and Dnmts via BCR-ABL1 inhibition.

Example 10: αCD70 Mab/Imatinib Combination Therapy Eliminates Murine CML LSCs In Vivo 1) Antibodies, Lineage Depletion and Flow Cytometry Anti-c-kit-PE-Cy7, anti-Sca-1-perinidin-chlorophyll-protein (PerCP)-Cy5.5 and anti-Gr1-PE were purchased from eBioscience. Armenian-hamster-IgG-PE, anti-c-kit-APC-Alexa750, anti-CD3α-biotin, anti-CD19-biotin, anti-Gr1-biotin, anti-Ter119-biotin, anti-CD34-APC, anti-CD45-Pacific-Blue, Streptavidin-BDHorizonV500 were purchased from BioLegend. 7-Aminoactinomycin D (7-AAD), αBrdU-APC (3D4), αCD70-PE (Ki-24) and the corresponding isotype control (MOPC21) were from BD Pharmingen.

Lineage depletion was performed with a cocktail of lineage-specific antibodies (anti-CD3-biotin, anti-CD19-biotin, anti-Gr1-biotin, anti-Ter119-biotin) using anti-biotin microbeads and MACS™ LS columns (Miltenyi Biotec). Samples were acquired on a BD LSRII and sorting procedures were conducted with a BD FACS Aria (BD Biosciences). Data were analyzed with FlowJo software (Treestar).

2) Leukemia Stem and Progenitor Cell Analysis

Leukemia stem and progenitor cell numbers in CML mice were analyzed by FACS. LSC sub-populations and leukemia progenitors in lin$^-$BCR-ABL1-GFP$^+$ BM cells were defined as follows: LT-LSCs (Sca-1$^+$c-kit$^{hi}$CD135$^-$CD48$^-$CD150$^+$); ST-LSCs (Sca-1$^+$c-kit$^{hi}$CD135$^-$CD48$^-$ CD150$^-$); leukemia multipotent progenitors (MPPs): MPP1s (Sca-1$^+$c-kit$^{hi}$CD135$^-$ CD48$^+$CD150$^+$); MPP2s (Sca-1$^+$c-kit$^{hi}$CD135$^-$CD48$^+$CD150$^-$); leukemia common myeloid progenitors (CMPs: Sca-1$^-$c-kit$^{hi}$CD127$^-$CD34$^+$FcgR$^-$) and leukemia granulocyte-macrophage progenitors (GMPs: Sca-1$^-$c-kit$^{hi}$CD127$^-$CD34$^+$FcgR$^+$).

3) Results

To analyze the effect of combining TKI treatment with CD70/CD27 inhibition on the survival of CML mice, fifteen days after transplantation, mice with comparable leukemia loads (49±5 Gr-1$^+$ BCR-ABL1-GFP$^+$ granulocytes/ml blood) were randomized and subjected to monotherapy with either vehicle, imatinib or a murine αCD70 blocking mAb (clone FR70) or combination therapy with αCD70 mAb/imatinib, and disease development and survival were monitored.

Monotherapy significantly delayed leukemia development and prolonged survival compared to the vehicle group; nevertheless, all animals eventually succumbed to CML. Strikingly, anti-CD70 mAb/imatinib combination therapy significantly improved survival of CML mice compared to monotherapy, and 60% of the animals receiving the combination therapy were alive up to 90 days after transplantation (FIG. 6, f). This suggested that CML was completely eradicated or at least effectively controlled long-term in these mice.

In order to investigate this issue, surviving mice were sacrificed and spleen weights and BM cell numbers were determined. In this experiment, only one out of 8 surviving mice receiving the combination treatment displayed a splenomegaly 90 days after transplantation, indicating the CML was still present at that time point (FIG. 11, a). Although all mice harbored residual BCR-ABL1-GFP$^+$ CML cells in the BM, only 3 of them with a high frequency of BCR-ABL1-GFP$^+$ BM cells were able to re-induce fatal CML upon secondary transplantation of 1×10$^7$ whole BM (WBM) cells into lethally irradiated (2×6.5 Gy) BL/6 recipients (FIG. 6, g). In contrast, secondary recipients receiving WBM cells from the other 5 donors that harbored few residual leukemia cells (4±2% BCR-ABL1-GFP$^+$ BM cells) survived up to 90 days without signs of leukemia, as analyzed by FACS of peripheral blood (FIG. 6, g). This indicates that anti-CD70 mAb/imatinib co-treatment targeted and eliminated the disease-initiating LSCs in a substantial fraction of the primary CML animals.

The BCR-ABL1-GFP$^+$ LSK cell population that contains the LSCs is heterogeneous and hierarchically organized and can be further sub-divided into long-term (LT-) LSCs, short-term (ST-) LSCs and leukemia multipotent progenitors (MPPs) using the markers CD150, CD135 and CD48. To analyze the impact of the combination treatment on these LSC sub-populations in more detail, especially on the disease-initiating LT-LSCs, CML mice harboring comparable leukemia loads (163±20 Gr-1$^+$ BCR-ABL1-GFP$^+$ granulocytes/ml blood) 15 days after transplantation were either treated with imatinib alone or with anti-CD70 mAb/imatinib combination therapy. Compared to imatinib treatment alone, anti-CD70 mAb/imatinib combination treatment resulted in significantly lower spleen weights and a lower leukemia load as indicated by lower numbers of BCR-ABL1-GFP$^+$ lin$^-$ leukemia cells and BCR-ABL1-GFP$^+$lin$^-$ c-kit$^{hi}$ leukemia progenitors in the BM (FIG. 11, c-f). Importantly, anti-CD70 mAb/imatinib combination therapy more efficiently reduced the BCR-ABL1-GFP$^+$ LSK cell population containing the disease-initiating LT-LSCs than imatinib treatment alone (FIG. 6, h-j and FIG. 11, g-h).

In addition, lin$^-$ BM cells from anti-CD70 mAb/imatinib treated CML animals formed significantly less BCR-ABL1-GFP$^+$ colonies than lin$^-$ cells from imatinib treated mice (FIG. 6, k). To further prove that the findings from FACS analysis and colony assays in vitro actually account for reduced numbers of LSCs in vivo, CML mice were either treated with imatinib alone or with anti-CD70 mAb/imatinib combination therapy starting 15 days after transplantation. Ten days later, mice were sacrificed and 3×10⁶ WBM cells were transplanted into sublethally irradiated (4.5 Gy) secondary recipients. Interestingly, recipients that received WBM cells from imatinib treated primary leukemia mice all succumbed to CML starting 25 days after secondary transplantation. In contrast, five out of 6 mice receiving WBM cells from mice that had been treated with the anti-CD70 mAb/imatinib combination therapy completely eliminated the disease and survived up to 90 days after secondary transplantation without signs of leukemia as analyzed by FACS of the blood (FIG. 6, *l*).

In summary, these data demonstrate that combination therapy using a TKI and a CD70/CD27 inhibitor selectively targets CML LSCs in vivo, particularly the disease-initiating LT-LSCs.

We claim:

1. A therapeutic combination comprising an anti-CD70 antibody and a BCR-ABL1 inhibitor, wherein the antibody comprises a heavy chain variable domain comprising the CDRH1, CDRH2, and CDRH3 amino acid sequences of the heavy chain variable domain amino acid sequence set forth in SEQ ID NO: 7; and a light chain variable domain comprising the CDRL1, CDRL2, and CDRL3 amino acid sequences of the light chain variable domain amino acid sequence set forth in SEQ ID NO: 8.

2. The therapeutic combination of claim 1, wherein the CDRH1, CDRH2, CDRH3, CDRL1, CDRL2, and CDRL3 regions comprise the amino acid sequences set forth in SEQ ID NOs: 1, 2, 3, 4, 5, and 6, respectively.

3. The therapeutic combination of claim 1, wherein the antibody comprises a heavy chain variable domain comprising the amino acid sequence set forth in SEQ ID NO: 7.

4. The therapeutic combination of claim 1, wherein the antibody comprises a light chain variable domain comprising the amino acid sequence set forth in SEQ ID NO: 8.

5. The therapeutic combination of claim 1, wherein the antibody comprises a heavy chain variable domain and a light chain variable domain comprising the amino acid sequences set forth in SEQ ID NOs: 7 and 8, respectively.

6. The therapeutic combination of claim 1, wherein the BCR-ABL1 inhibitor is selected from the group consisting of imatinib, nilotinib, dasatinib, bosutinib, ponatinib, bafetinib, saracatinib, tozasertib, and danusertib.

7. The therapeutic combination of claim 1, wherein the anti-CD70 antibody and BCR-ABL1 inhibitor are in the same formulation.

8. The therapeutic combination of claim 1, wherein the anti-CD70 antibody and BCR-ABL1 inhibitor are in separate formulations.

9. A kit comprising the therapeutic combination of claim 1, wherein the kit comprises a first container comprising the anti-CD70 antibody and a second container comprising the BCR-ABL1 inhibitor.

10. The kit of claim 9, further comprising instructions for using the therapeutic combination to treat a BCR-ABL1 related disorder.

* * * * *

SEQUENCE LISTING

```
<160> NUMBER OF SEQ ID NOS: 27

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Val Tyr Tyr Met Asn
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 2

Asp Ile Asn Asn Glu Gly Gly Thr Thr Tyr Tyr Ala Asp Ser Val Lys
1               5                   10                  15
Gly

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Asp Ala Gly Tyr Ser Asn His Val Pro Ile Phe Asp Ser
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Gly Leu Lys Ser Gly Ser Val Thr Ser Asp Asn Phe Pro Thr
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 5

Asn Thr Asn Thr Arg His Ser
1               5

<210> SEQ ID NO 6
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ala Leu Phe Ile Ser Asn Pro Ser Val Glu
1               5                   10

<210> SEQ ID NO 7
<211> LENGTH: 122
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Val Tyr
            20                  25                  30

Tyr Met Asn Trp Val Arg Gln Ala Pro Gly Lys Gly Leu Glu Trp Val
        35                  40                  45

Ser Asp Ile Asn Asn Glu Gly Gly Thr Thr Tyr Tyr Ala Asp Ser Val
    50                  55                  60

Lys Gly Arg Phe Thr Ile Ser Arg Asp Asn Ser Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Asp Ala Gly Tyr Ser Asn His Val Pro Ile Phe Asp Ser Trp
            100                 105                 110

Gly Gln Gly Thr Leu Val Thr Val Ser Ser
        115                 120

<210> SEQ ID NO 8
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 8

Gln Ala Val Val Thr Gln Glu Pro Ser Leu Thr Val Ser Pro Gly Gly
1               5                   10                  15

Thr Val Thr Leu Thr Cys Gly Leu Lys Ser Gly Ser Val Thr Ser Asp
            20                  25                  30

Asn Phe Pro Thr Trp Tyr Gln Gln Thr Pro Gly Gln Ala Pro Arg Leu
        35                  40                  45

Leu Ile Tyr Asn Thr Asn Thr Arg His Ser Gly Val Pro Asp Arg Phe
    50                  55                  60

```
Ser Gly Ser Ile Leu Gly Asn Lys Ala Ala Leu Thr Ile Thr Gly Ala
 65                  70                  75                  80

Gln Ala Asp Asp Glu Ala Glu Tyr Phe Cys Ala Leu Phe Ile Ser Asn
                 85                  90                  95

Pro Ser Val Glu Phe Gly Gly Gly Thr Gln Leu Thr Val Leu Gly
            100                 105                 110

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gttttagaag aatgaggtgg ag                                              22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
tcaacctatc aaaaaaccaa c                                               21

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgctttggtc ccattggtc                                                  19

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tacgtcccac ccaagtgac                                                  19

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gtatctagca agggtcacgg                                                 20

<210> SEQ ID NO 14
<211> LENGTH: 20
<212> TYPE: DNA
<213> ORGANISM: Artificial Sequence
```

```
<220> FEATURE:
<223> OTHER INFORMATION: Description of Artificial Sequence: Synthetic
      primer

<400> SEQUENCE: 14
tgtcctcaca ttcatccacc                                                   20

<210> SEQ ID NO 15
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
tcatttcctg gtatgacaac ga                                                22

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
cttcctcttg tgctcttgct g                                                 21

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
agaggccatt tatgtgtacc tg                                                22

<210> SEQ ID NO 18
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aggcaaattt cttctcacct gtg                                               23

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gttggtttca ttgtagcgga c                                                 21

<210> SEQ ID NO 20
<211> LENGTH: 19
<212> TYPE: DNA
<213> ORGANISM: Artificial Sequence
<220> FEATURE:
```

```
<223> OTHER INFORMATION: Description of Artificial Sequence: Synthetic
      primer

<400> SEQUENCE: 20
ccttccgagg aactgtgag                                                   19

<210> SEQ ID NO 21
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
agattgagac cactgttcct cc                                               22

<210> SEQ ID NO 22
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cttggcttcg tcgtaactct c                                                21

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
agaacatcat ccctgcatcc                                                  20

<210> SEQ ID NO 24
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcatcatact tggcaggttt ctc                                              23

<210> SEQ ID NO 25
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
agtgagggaa gagcctcag                                                   19

<210> SEQ ID NO 26
<211> LENGTH: 19
<212> TYPE: DNA
<213> ORGANISM: Artificial Sequence
<220> FEATURE:
<223> OTHER INFORMATION: Description of Artificial Sequence: Synthetic
```

```
          primer

<400> SEQUENCE: 26
aagtgtgctc ggagatgtg                                                      19

<210> SEQ ID NO 27
<211> LENGTH: 14
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 27
gaggtyggyg ggga                                                           14
```